United States Patent
Wehner et al.

(10) Patent No.: US 6,867,208 B2
(45) Date of Patent: Mar. 15, 2005

(54) VITRONECTIN RECEPTOR ANTAGONISTS, THEIR PREPARATION AND THEIR USE

(75) Inventors: Volkmar Wehner, Sandberg (DE); Hans Ulrich Stilz, Frankfurt (DE); Anuschirwan Peyman, Kelkheim (DE); Jochen Knolle, Kriftel (DE); Jean-Marie Ruxer, Issy les Moulineaux (FR); Denis Carniato, Marcoussis (FR); Jean-Michel Lefrancois, Livry Gargan (FR); Thomas Richard Gadek, Oakland, CA (US); Robert McDowell, San Francisco, CA (US)

(73) Assignees: Hoechst Aktiengesellschaft, Frankfurt am Main (DE); Genentech, Inc., South San Francisco, CA (US)

( * ) Notice: Subject to any disclaimer, the term of this patent is extended or adjusted under 35 U.S.C. 154(b) by 231 days.

(21) Appl. No.: 10/142,975

(22) Filed: May 13, 2002

(65) Prior Publication Data
US 2003/0027807 A1 Feb. 6, 2003

Related U.S. Application Data

(62) Division of application No. 09/777,011, filed on Feb. 6, 2001, now Pat. No. 6,387,895, which is a continuation of application No. 09/412,331, filed on Oct. 5, 1999, now Pat. No. 6,207,663, which is a division of application No. 08/995,521, filed on Dec. 22, 1997, now Pat. No. 6,011,045.

(30) Foreign Application Priority Data
Dec. 20, 1996 (DE) .......................................... 196 53 647

(51) Int. Cl.$^7$ ..................... A61K 31/437; C07D 471/04

(52) U.S. Cl. .................... 514/249; 514/265; 514/262.1; 514/264.1; 514/266.21; 514/300; 514/303; 514/383; 514/387; 540/460; 540/502; 544/253; 544/256; 544/279; 544/283; 544/284; 544/333; 546/119; 546/120; 546/121; 548/262.2; 548/303.1

(58) Field of Search ................................ 540/460, 502; 544/253, 256, 279, 283, 284, 333; 546/119, 120, 121; 548/262.2, 303.1; 514/249, 265, 262.1, 264.1, 266.21, 300, 303, 383, 387

(56) References Cited

FOREIGN PATENT DOCUMENTS

| | | |
|---|---|---|
| EP | 03/1993 | 3/1993 |
| EP | 741 133 | 11/1996 |
| WO | WO 93/00095 | 1/1993 |
| WO | WO 94/14776 | 7/1994 |
| WO | WO 95/18111 | 7/1995 |
| WO | WO 97/01540 | 1/1997 |
| WO | WO 97/24119 | 7/1997 |
| WO | WO 97/24122 | 7/1997 |
| WO | WO 97/24124 | 7/1997 |

*Primary Examiner*—Richard L. Raymond
(74) *Attorney, Agent, or Firm*—Foley & Lardner LLP

(57) ABSTRACT

The present invention relates to compounds of the formula I $$A-B-D-E-F-G \qquad (I)$$

in which A, B, D, E, F and G have the meanings given in the patent claims, to their preparation and to their use as medicaments. The compounds of the invention are used as vitronectin receptor antagonists and as inhibitors of bone resorption.

13 Claims, No Drawings

VITRONECTIN RECEPTOR ANTAGONISTS, THEIR PREPARATION AND THEIR USE

This application is a division of application Ser. No. 09/777,011, filed Feb. 6, 2001, now U.S. Pat. No. 6,387,895, which is a continuation of application Ser. No. 09/412,331, filed Oct. 5, 1999, now U.S Pat. No. 6,207,663, which is a division of application Ser. No. 08/995,521, filed Dec. 22, 1997, now U.S. Pat. No. 6,011,045.

The present invention relates to compounds of the formula I

A—B—D—E—F—G  (I)

in which A, B, D, E, F and G have the meanings given below, their physiologically tolerated salts and pharmaceutical preparations comprising these compounds, and to their preparation and use as vitronectin receptor antagonists for the treatment and prophylaxis of diseases which are based on the interaction between vitronectin receptors and their ligands in cell-cell or cell-matrix interaction processes, for example inflammations, cancer, tumor metastasis, cardiovascular disorders such as arteriosclerosis or restenosis, retinopathies and nephropathies, and diseases which are based on an undesirable degree of bone resorption, for example osteoporosis.

Human bones are subject to a continuous, dynamic process of reconstruction involving bone resorption and bone synthesis. These processes are regulated by cell types which are specialized for these purposes. While bone synthesis is based on the deposition of bone matrix by osteoblasts, bone resorption is based on the degradation of bone matrix by osteoclasts. Most bone disorders are based on an imbalance in the equilibrium between bone formation and bone resorption.

Osteoporosis is characterized by a loss of bone matrix. Activated osteoclasts are multinuclear cells which have a diameter of up to 400 μm and which demolish bone matrix. Activated osteoclasts become attached to the surface of the bone matrix and secrete proteolytic enzymes and acids into the so-called sealing zone, i.e. the region between their cell membrane and the bone matrix. The acid environment and the proteases degrade the bone.

Studies have shown that the attachment of osteoclasts to bone is regulated by integrin receptors on the surface of the osteoclast cells.

Integrins are a superfamily of receptors which includes, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the surface of a number of cells such as endothelial cells, cells of the smooth musculature of the blood vessels, osteoclasts and tumor cells. The vitronectin receptor $\alpha_v\beta_3$ which is expressed on the osteoclast membrane regulates the process of attachment to bone and bone resorption and consequently contributes to osteoporosis. In this connection, $\alpha_v\beta_3$ binds to bone matrix proteins, such as osteopontin, bone siloprotein and thrombospontin, which contain the tripeptide motif Arg-Gly-Asp (or RGD).

As vitronectin receptor antagonists, the novel compounds of the formula I inhibit bone resorption by osteoclasts. Bone disorders against which the novel compounds can be employed are, in particular, osteoporosis, hypercalcaemia, osteopenia, e.g. caused by metastases, dental disorders, hyperparathyroidism, periarticular erosions in rheumatoid arthritis, and Paget's disease. In addition, the compounds of the formula I may be employed for the alleviation, avoidance or therapy of bone disorders which are caused by glucocorticoid, steroid or corticosteroid therapy or by a lack of sex hormone(s). All these disorders are characterized by a loss of bone, due to an imbalance between bone synthesis and bone degradation.

Horton and coworkers describe RGD peptides and an anti-vitronectin receptor antibody (23C6) which inhibit tooth breakdown by osteoclasts and the migration of osteoclasts (Horton et al.; Exp. Cell. Res. 1991, 195, 368). In J. Cell Biol. 1990, 111, 1713, Sato et al. report that echistatin, an RGD peptide from snake venom, is a potent inhibitor of bone resorption in a tissue culture and an inhibitor of the attachment of osteoclasts to the bone. Fischer et al. (Endocrinology, 1993, 132, 1411) showed that echistatin also inhibits bone resorption in vivo in the rat.

The vitronectin receptor $\alpha_v\beta_3$ on human cells of the smooth blood vessel musculature of the aorta stimulates the migration of these cells into the neointima, thereby leading finally to artereosclerosis and restenosis following angioplasty (Brown et al., Cardiovascular Res. 1994, 28, 1815).

Brooks et al. (Cell 1994, 79, 1157) show that antibodies against $\alpha_v\beta_3$ or $\alpha_v\beta_3$ antagonists are able to shrink tumors by inducing the apoptosis of blood vessel cells during angiogenesis. Cheresh et al. (Science 1995, 270, 1500) describe anti-$\alpha_v\beta_3$ antibodies or $\alpha_v\beta_3$ antagonists which inhibit bFGF-induced angiogenesis processes in the rat eye, a property which could be therapeutically useful in the treatment of retinopathies.

Patent application WO 94/12181 describes substituted aromatic or nonaromatic ring systems, and WO 94/08577 describes substituted heterocycles, which are fibrinogen receptor antagonists and inhibitors of platelet aggregation. EP-A-0 528 586 and EP-A-0 528 587 disclose aminoalkyl-substituted or heterocyclyl-substituted phenylalanine derivatives, and WO 95/32710 discloses aryl derivatives, which are inhibitors of bone resorption due to osteoclasts. WO 96/00574 and WO 96/26190 describe benzodiazepines which are vitronectin receptor antagonists and integrin receptor antagonists, respectively. WO 96/00730 describes fibrinogen receptor antagonists templates, in particular benzodiazepines which are linked to a nitrogen-carrying 5-membered ring, which are vitronectin receptor antagonists. German patent applications P 19629816.4, P 19629817.2 and P 19610919.1 and also EP-A-0 796 855 describe substituted aromatic ring systems or 5-membered ring heterocycles which are vitronectin receptor antagonists.

The present invention relates to compounds of the formula I

A—B—D—E—F—G  (I)

in which:

A=A₁ or A₂, with

A₁=R²R³N—C(=NR²)NR²C(O)—, R²R³N—C(=NR²)NR²C(S)—, R²R³N—C(=NR²)NR²—S(O)—,

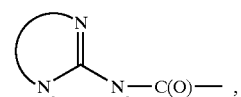 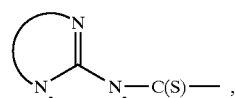

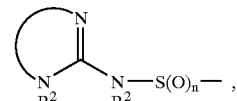

and A₂ =

-continued

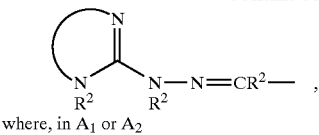

where, in $A_1$ or $A_2$

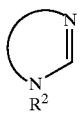

is a 5-membered to 10-membered monocyclic or polycyclic, aromatic or nonaromatic ring system which contains the grouping

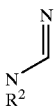

and, in addition, can contain from 1 to 4 heteroatoms from the group N, O and S, and, where appropriate, can be substituted, once or more than once, by $R^{12}$, $R^{13}$, $R^{14}$ or $R^{15}$;

B is a direct linkage, $(C_1–C_8)$-alkanediyl, $—CR^2=CR^3—$, $(C_5–C_{10})$-arylene, $(C_3–C_3)$-cycloalkylene, $—C\equiv C—$, which can in each case be substituted, once or twice, by $(C_1–C_8)$-alkyl (such as, for example, methyl-phenyl-methyl-, ethyl-CH=CH—, etc.);

D is a direct linkage, $(C_1–C_8)$-alkanediyl, $(C_5–C_{10})$-arylene, $—O—$, $—NR^2—$, $—CO—NR^2—$, $—NR—CO—$, $—NR^2—C(O)—NR^2—$, $—NR^2—C(S)—NR^2—$, $—OC(O)—$, $—C(O)O—$, $—CO—$, $—CS—$, $—S(O)—$, $—S(O)_2—$, $—S(O)_2—NR^2—$, $—S(O)—NR^2—$, $—NR^2—S(O)—$, $—NR^2—S(O)_2—$, $—S—$, $—CR^2=CR^3—$, $—C\equiv C—$, $—NR^2—N=CR^2—$, $—N=CR^2$, $—R^2C=N—$, $—CH(OH)—$, which can in each case be substituted, once or twice, by $(C_1–C_8)$-alkyl, $—CR^2=CR^2—$ or $(C_5–C_6)$-aryl, such as, for example, methyl-phenyl-CH=CH—, ethyl-O—, etc., with it being possible, if B is a direct linkage, for D also to be a direct linkage or a radical as defined under D, which radical is substituted once or twice, as described under D, and is linked to B by way of one of these substituents.

E a) is a template from the series of fibrinogen receptor antagonists, which template is taken from the following patent applications, patent documents or literature references:

Adir et Compagnie
FR 928004, Jun. 30, 1992, Fauchere, J. L., et al.
EP 0578535, Jun. 29, 1993, Fauchere, J. L., et al.
CA 2128560, Jan. 24, 1995, Godfroid, J. J., et al.
Asahi Breweries, Ltd.
JP 05239030, Sep. 17, 1993.
Asahi Glass
WO 90/02751, Ohba, M. et al., Sep. 8, 1989.
WO 90/115950, Mar. 22, 1990, Ohba, M., et al.
EP 0406428, Jan. 9, 1991.
WO 92/09627, Isoai, A. et al., Nov. 29, 1991.
Chiron
WO 93/07169, (Der 93-134382/16), Mar. 15, 1993, Devlin, J. J., et al.
Ciba Geigy
EP 0452210, (Der 91-305246/42) Apr. 5, 1990.
EP 0452257, Mar. 26, 1991, Allen, M. C., et al.
COR Therapeutics
WO 90/15620, Jun. 15, 1990.
EP 0477295, Apr. 1, 1992: Scarborough, R. M., et al.
WO 92/08472, May 29, 1992, Scarborough, R. M., et al.
WO 93/223356, Apr. 27, 1993, Swift, R. L., et al.
EP 0557442, Sep. 1, 1993, Scarborough, R. M., et al.
Scarborough, R. M.; Rose, J. W.; Hsu, M. A.; Phillips, D. R.; Fried, V. A.; Campbell, A. M.; Nunnizzi, L.; Charo, I. F., Barbourin, A GPIIb-IIIa-Specific Integrin Antagonist from the Venom of Sistrurus M. Barbouri, J. Biol. Chem, 266, 9359, 1991.
Daiichi Pharm Co Ltd.
JP 05078344-A, (Der 93-140339/17), Mar. 30, 1993.
DuPont Merck
WO 93/07170, Apr. 15, 1993.
WO 94/11398, May 26, 1994, Wells, G. J., et al. IL 109237, Jul. 31, 1994.
WO 94/22909, (Der 94-333113/41) Oct. 13, 1994: DeGrado W. F., et al.
WO 94/22910, (Der 94-333114/41) Oct. 13, 1994: DeGrado W. F., et al.
WO 94/22494, (Der 94-332838/41) Oct. 13, 1994: DeGrado W. F., et al.
EP 625164, Nov. 23, 1994: Degrado, W. F., et al.
WO 95/14682, Jun. 1, 1995, Wityak, J., et al.
WO 95/14683, Jun. 1, 1995, Wityak, J., et al.
WO 95/18111, Jul. 6, 1995, DeGrado, W. F., et al.
WO 95/23811, Sep. 8, 1995, DeGrado, W. F., et al.
Mousa, S. A.; Bozarth, J. M.; Forsythe, M. S.; Jackson, S. M., Leamy, A.;
Diemer, M. M.; Kapil, R. P.; Knabb, R. M.; Mayo, M. C.; Pierce, S. K.; al., e., Antiplatelet and Antithrombotic Efficacy of DMP 728, a Novel Platelet GPIIb/IIIa Receptor Antagonist, Circulation, 89, 3, 1994.
Jackson, S.; DeGrado, W.; Dwivedi, A.; Parthasarathy, A.; Higley, A.; Krywko, J.; Rockwell, A.; Markwalder, J.; Wells, G.; Wexler, R.; Mousa, S.; Harlow, R., Template-Constrained Cyclic Peptides: Design of High-Affinity Ligands for GPIIb/IIIa, J. Amer. Chem. Soc., 116, 3220, 1994.
E. Merck
EP 0608759, Jan. 19, 1994, Gante, J., et al.
EP 0623615, Apr. 19, 1994, Raddatz, P., et al.
EP 0645376, Sep. 15, 1994, Gante, J., et al.
EP 0668278, Feb. 14, 1995, Juraszyk, H., et al.
EP 0697408, Aug. 10, 1995, Juraszyk, H., et al.
DE 4310643, (Der 94-311172/39), Oct. 6, 1994, Jonczyk, A., et al.
WO 9404093, Oct. 27, 1994, Jonczyk, A., et al.
EP 0632053, Jan. 4, 1995, Jonczyk, A., et al.
EP 576898, Jan. 5, 1994, Jonczyk, A., et al.
EP 0608759 A, Aug. 3, 1994, Gaute, J. P., et al.
HU 9400249, May 30, 1994, Gante, J., et al.
Ellem Ind Farma Spa
GB 2207922, Aug. 3, 1988.
Farmitalia Carlo Erba SRL
EP 611765 (Der 94-265375/33), Aug. 24, 1994, Cozzi, P., et al.
Fuji Photo Film
JP 04208296-A (Der. 92-303598/38), Nov. 30, 1990.
JP 04213311-A (Der. 92-305482/38), Nov. 27, 1990.
JP 04217693-A (Der. 92-312284/38), Oct. 23, 1990.
JP 04221394-A (Der. 92-313678/38), Oct. 26, 1990.
JP 04221395-A (Der. 92-313679/38), Oct. 26, 1990.
JP 04221396-A (Der. 92-313680/38), Oct. 26, 1990.

JP 04221397-A (Der. 92-313681/38), Dec. 20, 1990.
EP 0482649 A2, Apr. 29, 1992, Kojima, M., et al.
EP 0488258A2, Jun. 3, 1992, Komazawa, H., et al.
EP 0503301-A2, Feb. 14, 1991, Kitaguchi, H., et al.
JP 05222092, May 21, 1993, Nishikawa, N., et al.
JP 06239885, (Der 94-313705/39), Aug. 30, 1993, Nishikawa, N., et al.
WO 9324448, (Der 93-405663/50), Dec. 9, 1993, Nishikawa, N., et al.
JP 06228189, (Der 94-299801/37), Aug. 16, 1994.
EP 0619118, (Der 94-311647/39), Oct. 12, 1994, Nishikawa, N., et al.
Fujisawa
EP 0513675, May 8, 1992, N. Umekita, et al.
WO 9409030-A1, Apr. 28, 1994, Takasugi, H., et al.
EP 0513675, (Der 92-383589/47).
WO 9500502, Jan. 5, 1995, Oku, T., et al.
WO 95/08536, Mar. 30, 1995, Ohkubo, M., et al.
FR 144633: Thromb Haem. 69, 706, 1993.
Cox, D.; Aoki, T.; Seki, J.; Motoyama, Y.; Yoshida, K., Pentamidine: A Specific Nonpeptide GPIIb/IIIa Antagonist, Thromb. Haem., 69, 707, 1993.
Genentech
WO 90/15072 (Der 91007159).
WO 91/01331 (Der 91058116), Jul. 5, 1990, P. L. Barker, et al.
WO 91/04247, Sep. 24, 1990, T. R. Webb.
WO 91/11458 (Der 91252610), Jan. 28, 1991, P. L. Barker, et al.
WO 92/07870, Oct. 24, 1991 J. P. Burnier, et al.
WO 92/17492, Oct. 15, 1992, Burnier, J. P., et al.
U.S. Pat. No. 5,250,679, Oct. 5, 1993, Blackburn, B. K., et al.
U.S. Pat. No. 5,403,836, Apr. 4, 1995, Blackburn, B. K., et al.
U.S. Pat. No. 5,565,449 Oct. 15, 1996, Blackburn, B. K., et al.
CA 2106314, Oct. 6, 1992, Burnier, J. P., et al.
WO 93/08174, Oct. 15, 1991, B. K. Blackburn, et al.
CA 2106314, Oct. 6, 1992, Burnier, J. P., et al.
EP 0555328, Aug. 18, 1993, J. P. Burnier, et al.
WO 95/04057, Feb. 9, 1995, Blackburn, B. K., et al.
Scarborough, R. M., Naughton, M. A., Teng, W., Rose, J. W., Phillips, D. R., Nannizzi, L., Arfsten, A., Campbell, A. M., and Charo, I. F., J. Biol. Chem. 268, 1066, 1993.
Dennis, M. S.; Henzel, W. J.; Pitti, R. M.; T., L. M.; Napier, M. A.; Deisher, T. A.; Bunting, S.; Lazarus, R., Platelet Glycoprotein IIb-IIIa Protein Antagonists from Snake Venoms: Evidence for a Family of Platelet-Aggregation Inhibitors, Proc. Natl. Acad. Sci. USA, 87, 2471, 1989.
Barker, P. L.; Bullens, S.; Bunting, S., Burdick, D. J.; Chan, K. S.; Deisher, T.; Eigenbrot, C.; Gadek, T. R.; Gantzos, R.; Lipari, M. T.; Muir, C. D.; Napier, M. A.; Pitti, R. M.; Padua, A.; Quan, C.; Stanley, M.; Struble, M.; Tom, J. Y. K.; Burnier, J., P., Cyclic RGD Peptide Analogues as Antiplatelet Antithrombotics, J. Med. Chem., 35, 2040, 1992.
McDowell,. R. S.; Gadek, T. R., Structural Studies of Potent Constrained RGD Peptides, J. Amer. Chem Soc., 114, 9245, 1992.
Glaxo
EP 0537980, Oct. 13, 1992, B. Porter, et al.
EP 0542363, Nov. 10, 1992, Porter, B., et al.
WO 93/10091, May 27, 1993, Porter, B., et al.
WO 93/14077, Jul. 22, 1993, Porter, B., et al.
WO93/22303, Jan. 11, 1993, Middlemiss, D., et al.
WO 93/14077, Jan. 15, 1993, B. Porter, et al.
EP 0609282 A1, Aug. 10, 1994, Porter, B., et al.
EP 0612313, Aug. 31, 1994, Porter, B., et al.
EP 903911769, Apr. 20, 1994, Middlemiss, D., et al.
EP 0637304 A1, Feb. 8, 1995, Middlemiss, D., et al.
Hann, M. M.; Carter, B.; Kitchin, J.; Ward, P.; Pipe, A.; Broomhead, J.; Horuby, E.; Forster, M.; Perry, C., An Investigation of the Bioactive Conformation of ARG-GLY-ASP containing Cyclic Peptides and Snake Venom Peptides which Inhibit Human Platelet Aggregation, In Molecular Recognition: Chemical and Biochemical Problems II, S. M. Roberts, Ed., The Royal Society of Chemistry, Cambridge, 1992.
Ross, B. C. Nonpeptide Fibrinogen Receptor Antagonists, (SAR leading to the discovery of GR 144053), In Seventh RSC-SCI Medicinal Chemistry Symposium, The Royal Society of Chemistry Fine Chemicals and Medicinals Group and SCI Fine Chemicals Group, Churchill College, Cambridge, 1993, L20.
Pike, N. B.; Foster, M. R.; Hornby, E. J.; Lumley, P., Effect of the Fibrinogen Receptor Antagonist GR144053 Upon Platelet Aggregation Ex Vivo Following Intravenous and Oral Administration to the Marmoset and Cynomologous Monkey, Thromb. Haem., 69, 1071, 1993.
Hoffmann-La Roche
AU 9344935, (Der 94-118783/15), Mar. 10, 1994.
EP 0592791, Apr. 20, 1994, Bannwarth. W., et al.
Kogyo Gijutsuin
JP 06179696, Jun. 28, 1994, Maruyama, S., et al.
Kyowa Hakko Kogyo KK
JP 05078244-A, Mar. 30, 1993.
Laboratoire Chauvin
WO 9401456, Jan. 20, 1994, Regnouf, D. V. J., et al.
La Jolla Cancer Res. Fndn
WO 9500544, Jan. 5, 1994, Pierschbacher, M. D., et al.
U.S. Pat. No. 079,441, Jan. 5, 1994, Pierschbacher, M. D., et al.
Lilly/COR
EP 0635492, Jan. 25, 1995, Fisher, M. J., Happ, A. M., Jakubowski, J. A. Kinnick, M. D., Kline, A. D., Morin, Jr., J. M., Sall, M. A., Vasileff, R. T.
EP 0655439, Nov. 9, 1994, Denney, M. L., et al.
Medical University of South Carolina
EP 587770, Mar. 23, 1994, Halushka, P. V., Spicer, K. M.
Merck
EP 0368486 (Der 90-149427/20), Nov. 10, 1988.
EP 0382451 (Der 90248531).
EP 0382538 (Der 90248420).
EP 0410537, Jul. 23, 1990, R. F. Nutt, et al.
EP 0410539, Jul. 25, 1990, R. F. Nutt, et al.
EP 0410540, Jul. 25, 1990, R. F. Nutt, et al.
EP 0410541, Jul. 25, 1990, R. F. Nutt, et al.
EP 0410767, Jul. 26, 1990, R. F. Nutt, et al.
EP 0411833, Jul. 26, 1990, R. F. Nutt, et al.
EP 0422937, Oct. 11, 1990, R. F. Nutt, et al.
EP 0422938, Oct. 11, 1990, R. F. Nutt, et al.
EP 0487238, Oct. 13. 1991, T. M. Connolly, et al.
EP 0437367 (Der 91209968), M. Sato, et al.
WO 9409029, Apr. 28, 1994, Nutt, R. F. and Veber, D. F.
EP 618225, (Der 94-304404/38) Oct. 5, 1994.
EP 0479481, Sep. 25, 1991, M. E. Duggan, et al.
EP 0478362, Sep. 27, 1991 M. E. Duggan, et al.
EP 0512831, May 7, 1992, Duggan, M. E., et al.
EP 0540334, Oct. 29, 1992, G. D. Hartman, et al.
U.S. Pat. No. 5,264,420-A, Nov. 23, 1993.
U.S. Pat. No. 5,272,158, Dec. 21, 1993, Hartmann G. D., et al.
U.S. Pat. No. 5,281,585, Jan. 25, 1994, Ihle, N., et al.

GB 945317 A, Mar. 17, 1994 (Priority US.. No. 34042A, Mar. 22, 1993).
GB 2271567 A, Apr. 20, 1994, Hartman, G. D., et al.
WO 9408962, Apr. 28, 1994, Hartmann, G. D., et al.
WO 9409029, (Der 94-151241/18) Apr. 28, 1994, Hartman, G. D., et al.
U.S. Pat. No. 5,321,034, Jun. 14, 1994, Duggan, M. E., et al.
U.S. Pat. No. 5,334,596, Aug. 2, 1994, Hartman, G. D., et al.
U.S. Pat. No. 5,328,900, Jul. 12, 1994, Klein, S. I., et al.
U.S. Pat. No. 5,332,726, Jul. 26, 1994, Klein, S. I., et al.
U.S. Pat. No. 5,451,578, Sep. 19, 1995, Claremon, D. A., et al.
U.S. Pat. No. 5,455,243, Oct. 3, 1995, Duggan, M. E., et al.
WO 9418981, (Der 94-293975/36) Sep. 1, 1994, Claremon, D. A., et al.
GB 2276384, (Der 94-287743/36) Sep. 28, 1994, Claremon, D. A., Liverton, N.
WO 9422825, Oct. 13, 1994, Claremon, D. A., Liverton, N. J.
WO 9504531, Feb. 16, 1995, Hartman, G. D., et al.
WO 95/17397, Jun. 29, 1995, Hartmann, G. D., et al.
Nutt, R. F.; Brady, S. F.; Colton, C. D.; Sisko, J. T.; Ciccarone, T. M.; Levy, M. R.; Duggan, M. E.; Imagire, I. S.; Gould, R. J.; Anderson, P. S.; Veber, D. F., Development of Novel, Highly Selective Fibrinogen Receptor Antagonists as Potentially Useful Antithrombotic Agents, In Peptides, Chemistry and Biology, Proc. 12th Amer. Peptide Symp., J. A. Smith and J. E. Rivier, Ed., ESCOM, Leiden, 1992; 914.
Hartman, G. D.; Egbertson, M. S.; Halszenko, W.; Laswell, W. L.; Duggan, M. E.; Smith, R. L.; Naylor, A. M.; Manno, P. D.; Lynch, R. J.; Zhang, G.; Chang, C. T. C.; Gould, R. J., Non-peptide Fibrinogen Receptor Antagonists. 1. Discovery and Design of Exosite Inhibitors, J. Med. Chem., 35, 4640, 1992.
Gould, R. J.; Barrett, S.; Ellis, J. D.; Holahan, M. A.; Stranieri, M. T.; Theoharides, A. D.; Lynch, J. J.; Friedman, P. A.; Duggan, M. E.; Ihle, N. C.; Anderson, P. S.; Hartman, G. D., Characterization of L-703,014, A Novel Fibrinogen Receptor Antagonist, Following Oral Administration to Dogs, Thromb. Haem., 69, 539, 1993.
Merrell Dow
WO 93/24520, May 14, 1993, Harbeson, S. L., et al.
WO 9324520, Dec. 9, 1993, Harbeson, Bitonti, J., A.
WO 9429349, Dec. 22, 1994, Harbeson, Bitonti, J., A.
Nippon Steel Corp
WO 9405696, Mar. 17, 1993, Sato, Y., et al.
EP 628571, Dec. 14, 1994, Sato, Y., et al.
WO 9501371, Jan. 12, 1995, Sato, Y., et al.
ONO Pharmaceuticals
JP 05286922 (Der 93-383035/48)
Roche
EP 038,362, Feb. 19, 1990, M. Muller, et al.
EP 0372486, Jun. 13, 1990, Allig, L., et al.
EP 0381033, Jul. 8, 1990, Allig, L., et al.
EP 0384362, Aug. 29, 1990, Allig, L., et al.
EP 0445796, Sep. 11, 1991, Allig, L., et al.
EP 0505868, Sep. 30, 1992, Allig, L., et al.
U.S. Pat. No. 5,273,982-A, (Der 94-006713/01) Dec. 28, 1993.
U.S. Pat. No. 5,430,024, Jul. 4, 1995, Allig, L., et al.
EP 0468231, Jul. 2, 1991, Ackermann, J., et al.
EP 0656348, Nov. 26, 1994, Allig, L., et al.
Allig, L.; Edenhofer, A.; Hadvary, P.; Hurzeler, M.; Knopp, D.; Muller, M.; Steiner, B.; Trzeciak, A.; Weller, T., Low Molecular Weight, Non-peptide Fibrinogen Receptor Antagonists, J. Med. Chem. 35, 4393, 1992.
Rhone-Poulenc Rorer
U.S. Pat. No. 4,952,562, Sep. 29, 1989, S. I. Klein, et al.
U.S. Pat. No. 5,064,814, (Der 91-353169/48) Apr. 5, 1990.
WO 9104746, Sep. 25, 1990, S. I. Klein, et al.
WO 91/05562, Oct. 10, 1989, S. I. Klein, et al.
WO 91/07976, (Der 91-192965) Nov. 28, 1990, S. I. Klein, et al.
WO 91/04746, S. I. Klein, et al.
WO 92/18117, Apr. 11, 1991, S. I. Klein, et al.
U.S. Pat. No. 5,086,069, (Der 92-064426/08) Apr. 2, 1992.
WO 92/17196, Mar. 30, 1992, S. I. Klein, et al.
U.S. Pat. No. 5,328,900, (Der 94-221950/27) Jul. 12, 1992.
U.S. Pat. No. 5,332,726, (Der 94-241043/29) Jul. 26, 1994.
WO 93/11759, Dec. 7, 1992, S. I. Klein, et al.
EP 0577775, Jan. 12, 1994, Klein, S. I., et al.
WO 95/10295, Apr. 20, 1995, Klein, S. I., et al.
CA 2107088, Sep. 29, 1992, Klein, S. I., et al.
Sandoz
EP 0560730, Mar. 8, 1993, G. Kottirisch and R. Metternich.
G. Kottirisch, et al. Biorg. Med. Chem. Lett 3, 1675–1680, 1993.
Schering AG
EP 530937, Mar. 10, 1993, Noeski-Jungblut, C., et al.
Searle/Monsanto
EP 0319506, (Der 89-3195506) Dec. 2, 1988, S. P. Adams, et al.
EP 0462,960, Jun. 19. 1991, Tjoeng, F. S., et al.
U.S. Pat. No. 4,857,508, S. P. Adams, et al.
EP 0502536, (Der 92-301855) Mar. 3, 1991, R. B. Garland, et al.
EP 0319506, Dec. 2, 1988, S. P. Adams, et al.
U.S. Pat. No. 4,992,463, Aug. 18, 1989.
U.S. Pat. No. 5,037,808, Apr. 23, 1990.
EP 0454651 A2, Oct. 30, 1991, Tjoeng, F. S., et al.
U.S. Pat. No. 4,879,313, Jul. 20, 1988.
WO 93/12074, Nov. 19, 1991, N. Abood, et al.
WO 93/12103, Dec. 11, 1991, P. R. Bovy, et al.
U.S. Pat. No. 5,091,396, Feb. 25, 1992, Tjoeng, F. S., et al.
WO 92/15607, Mar. 5, 1992, Garland, R. B., et al.
WO 93/07867, Apr. 29, 1993, P. R. Bovy, et al.
U.S. Pat. No. 888,686, May 22, 1992, Bovy, P. R., et al.
CA 2099994, Sep. 7, 1992, Garland, R. B., et al.
EP 0513810, May 15, 1992, Garland, R. B., et al.
U.S. Pat. No. 5,254,573, Oct. 19, 1993, Bovy, P. R., et al.
EP 0539343, Oct. 14, 1992, P. R. Bovy, et al.
WO 93/12074, Nov. 27, 1992, N. A. Abood, et. al.
WO 93/12103, Dec. 11, 1992, P. R. Bovy, et al.
EP 0539343, Apr. 28, 1993, Bovy, P. R., et al.
EP 0542708, May 19, 1993, Bovy. P. R., et al.
WO 94/00424, Jan. 6, 1994, Abood, N. A., et al.
WO 93/16038, Aug. 16, 1993, Miyano. M., et al.
WO 93US7975, Aug. 17, 1993, Zablocki, J. A., Tjoeng, F. S.
WO 93/18058, Sep. 16, 1993, Bovy, P. R., et al.
U.S. Pat. No. 5,254,573, Oct. 19, 1993, Bovy, P. R., et al.
U.S. Pat. No. 5,272,162, Dec. 21, 1993, Tjoeng, F. S., et al.
EP 0574545, Dec. 22, 1993, Garland, R. B., et al.
WO 9401396, Jan. 20, 1994, Tjoeng, F. S., et al.
WO 9405694, (Der 94-101119/12) Mar. 17, 1994, Zablocki, et al.
U.S. Pat. No. 5,314,902, May 24, 1994, Adams, S. P., et al.
WO 9418162, Aug. 18, 1994, Adams, S. P., et al.
WO 9419341, Sep. 1, 1994, Tjoeng, F. S., et al.
U.S. Pat. No. 5,344,837, (Der 94-285503/35), Sep. 6, 1994, Zablocki, J. A., et al.
EP 614360, Sep. 14, 1994, Bovy, P. R., et al.
WO 9420457, (Der 94-302907/37), Sep. 15, 1994, Tjoeng, F. S., et al.

WO 9421602, (Der 94-316876/39), Sep. 29, 1994, Tjoeng, F. S., et al.
WO 9422820, Oct. 13, 1994, Abood, N. A., et al.
EP 630366, Dec. 28, 1994, Bovy, P. R., et al.
U.S. Pat. No. 5,378,727, Jan. 3, 1995, Bovy, P. R., et al.
WO 95/06038, Mar. 2, 1995, Bovy P. R., et al.
WO 93/08164, Apr. 29, 1993, Bovy, P. R., et al.
K. F. Fok, et al., Int. J. Peptide Prot. Res., 38, 124–130, 1991, SAR of RGDY analogs.
J. A. Zablocki, et al. J. Med. Chem. 35, 4914–4917, 1992, SAR summary of guanidinoalkanoyl-Asp-Phe analogs.
Tjoeng, F. S.; Fok, K. F.; Zupec, M. E.; Garland, R. B.; Miyano, M.; Panzer-Knodle, S.; King, L. W.; Taite, B. B.; Nicholson, N. S.; Feigen, L. P.; Adams, S. P., Peptide Mimetics of the RGD Sequence, In Peptides, Chem. and Biol. Proc. 12th Amer. Peptide Symp., J. A. Smith and J. E. Rivier, Ed., ESCOM, Leiden, 1992; 752.
Nicholson, N.; Taite, B.; Panzer-Knodle, S.; Salyers, A.; Haas, N.; Szalony, J.; Zablocki, J.; Feigen, L.; Glenn, K.; Keller, B.; Broschat, K.; Herin, M.; Jacqmin, P.; Iesne, M., An Orally Active Glycoprotein IIb/IIIa Antagonist-SC-54684, Thromb. Haem, 69, 975, 1993.
Smithkline Beecham Corporation
WO 91/07429, May 30, 1991, Ali, F., et al.
WO 92/07568, May 14, 1992, Callahan, J. F., et al.
WO 92/13552, Aug. 20, 1992, Ali, F., et al.
WO 93/00095, Jan. 7, 1993, Bondinell, W. E., et al.
WO 93/09133, May 13, 1993, Callahan, J. F., et al.
WO 94/12478, Jun. 9, 1994, Keenan, R. M. C., et al.
WO 94/14775, Jul. 7, 1994, Bondinell, W. E., et al.
WO 94/22440, Oct. 13, 1994, Callahan, J. F., et al.
WO 94/14776, Jul. 7, 1994, Bondinell, W. E., et al.
WO 94/15913, Jul. 21, 1994, Samanen, J.
WO 94/29273, Dec. 22, 1994, Samanen, J.
WO 95/18619, Jul. 13, 1995, Bondinell, W. E., et al.
WO 96/06087, Feb. 29, 1996, Kwon, C., et al.
WO 96/00730, Jan. 11, 1996, Ali, F., et al.
Sumitomo Pharm. Co. Ltd
WO 9501336, Jun. 6, 1994, Ikeda, Y., et al.
Sumitomo Seiyaku KK
JP 06025290, (Der 94-077374/10), Feb. 1, 1994.
Taisho Pharm. (Teijin, Ltd)
JP 05230009, (Der 93-317431/40), Feb. 24, 1992.
JP 9235479, Feb. 24, 1992.
WO 94/17804, Aug. 18, 1994, Mizushima, Y.
EP 0634171, Jan. 18, 1995, Nizushima, M.
Takeda
EP 0529858, Apr. 3, 1993, H. Sugihara, et al.
EP 0606881, Jul. 20, 1994.
EP 0614664, Sep. 14, 1994, Miyake, A., et al.
Tanabe
WO 89/07609, T. J. Lobl, et al.
WO 92/00995, Jul. 9, 1991, T. J. Lobl, et al.
WO 93/08823, Nov. 6, 1991, T. C. McKenzie.
CA 2087021, Jan. 10, 1991, Lobl, T. J., et al.
WO 92/08464, Nov. 15, 1991, T. C. McKenzie, et al.
Telios/La Jolla Cancer Research
U.S. Pat. No. 4,578,079, Nov. 22, 1983, E. Ruoslahti, and M. Pierschbacher.
U.S. Pat. No. 4,614,517, Jun. 17, 1985, E. Ruoslahti, and M. Pierschbacher.
U.S. Pat. No. 4,792,525, Jun. 17, 1985, E. Ruoslahti, and M. Pierschbacher.
U.S. Pat. No. 4,879,237, (Der 90-154405/20) May 24, 1985.
WO 91/15515, (Der 91-325173/44) Apr. 6, 1990.
U.S. Pat. No. 5,041,380, 1991, E. Ruoslahti, and M. Pierschbacher.
WO 95/00544 Jan. 5, 1995, Craig, W. S., et. al.
Cheng, S.; Craig, W. S.; Mullen, D.; Tschopp, J. F.; Dixon, D.; Pierschbacher, M. F., Design and Synthesis of Novel Cyclic RGD-Containing Peptides as highly Potent and Selective Integrin $\alpha_{IIb}\beta_3$ Antagonists, J Medicin. Chem. 37, 1, 1994.
Collen, D.; Lu, H. R.; Stassen, J.-M.; Vreys, I.; Yasuda, T.; Bunting, S.; Gold, H. K., Antithrombotic Effects and Bleeding Time Prolongation with Synthetic Platelet GPIIb/IIIa Inhibitors in Animal Models of Platelet-Mediated Thrombosis, Thrombosis and Haemostasis, 71, 95, 1994.
Temple U.
WO 9409036, (Der 94-151248/18), Apr. 28, 1994.
Terumo KK
JP 6279389, Oct. 4, 1994, Obama, H., et al.
Karl Thomae/Boehringer Ingelheim
EP 0483667, May 6, 1992, Himmelsbach, F., et al.
EP 0496378, Jan. 22, 1992, Himmelsbach, F., et al.
EP 0503548, Sep. 16, 1992, Himmelsbach, F., et al.
AU A-86926/91, May 7, 1992, Himmelsbach, F., et al.
EP 0528369, Feb. 24, 1993, Austel, V., et al.
EP 0537696, Apr. 21, 1993, Linz, G., et al.
DE 4124942, Jan. 28, 1993, Himmelsbach, F., et al.
DE 4129603, Mar. 11, 1993, Pieper, H., et al.
EP 0547517 A1, (Der 93-198544) Jun. 23, 1993, Soyka, R., et al.
EP 0567966, Nov. 3, 1993, Himmelsbach, F., et al.
EP 0567967, Nov. 3, 1993, Weisenberger, J., et al.
EP 0567968, Nov. 3, 1993, Linz, G., et al.
EP 0574808, Jun. 11, 1993, Pieper, H., et al.
Der 93-406657/51, Austel, V., et al.
EP 587134, (Der 94-085077/11) Mar. 16, 1994, Himmelsbach, F., et al.
EP 589874, Apr. 6, 1994, Grell, W., et al.
(P534005), DE 4234295, Apr. 14, 1994, Pieper, H., et al.
EP 0592949, Apr. 20, 1994, Pieper, H. D., et al.
EP 0596326, May 11, 1994, Maier, R., et al.
DE 4241632, Jun. 15, 1994, Himmelsbach, F., et al.
EP 0525629, Jul. 22, 1992, Himmelsbach, F., et al.
EP 0531883, Sep. 3, 1992, Austel, V., et al.
EP 0604800 A, Jul. 6, 1994, Himmelsbach, F., et al.
DE 4302051, (Der 94-235999/29) Jul. 28, 1994.
EP 0608858 A, Aug. 3, 1994, Linz, G. D., et al.
DE 4304650, (Der 94-256165/32), Aug. 18, 1994, Austel, V., et al.
EP 611660, Aug. 24, 1994, Austel, V., et al.
EP 0612741, Feb. 21, 1994, Himmelsbach, F., et al.
DE 4305388, (Der 94-264904/33), Aug. 25, 1994, Himmelsbach, F., et al.
EP 612741, (Der 94-265886/33), Aug. 31, 1994, Himmelsbach, F., et al.
EP 0639575 A, Feb. 22, 1995, Linz, G., et al.
DE 4324580, Jan. 26, 1995, Linz, G., et al.
EP 0638553, Feb. 15, 1995, Himmelsbach, F., et al.
WO 95/24405, Sep. 14, 1995, Himmelsbach, F., et al.
WO 96/02514, Feb. 1, 1996, Himmelsbach, F., et al.
WO 96/02504, Feb. 1, 1996, Himmelsbach F., et al.
DE 4427838, Feb. 8, 1996, Himmelsbach, F., et al.
WO 96/05194, Feb. 22, 1996, Himmelsbach, F., et al.
DE 4431868, Mar. 14, 1996, Pieper, H., et al.
DE 4429079, Feb. 22, 1996, Himmelsbach, F., et al.
F. Himmelsbach, V. Austel, G. Kruger, H. Pieper, H. Weisenberger, T. H. Muller, and W. G. Eisert, in XIIth Int. Symp. on Med. Chem. Basel, Book of Abstracts, 47, 1992.
V. Austel, W. Eisert, F. Himmelsbach, G. Kruger, G. Linz, T. Muller, H. Pieper, and J. Weisenberger, Natl. Mtg. Amer. Chem. Soc. Book of Abstracts, Denver, Div. Med. Chem., 1993.

Muller, T. H.; Schurer, H.; Waldmann, L.; Bauer, E.; Himmelsbach, F.; Binder, K., Orally Activity of BIBU 104, a Prodrug of the Non-peptide Fibrinogen Receptor Antagonist BIBU 52, in Mice and Monkeys, Thromb. Haem., 69, 975, 1993.
Univ. California
WO 94/14848, Jul. 7, 1994, Zanetti, M.
Univ. New York
WO 94/00144, Jun. 29, 1993, Ojima, I., et al.
Yeda Res. and Dev. Co.
WO 93/09795, (Der 93-182236/22), Lido, O., et al.
Zeneca
WO 9422834, Oct. 13, 1994, Wayne, M. G., et al.
WO 9422835, Oct. 13, 1994, Wayne, M. G., et al.
EP 632016, Jan. 4, 1995, Brewster, A. G., et al.
EP 632019, Jan. 4, 1995, Brown, G., Shute, R. E.
EP 632020, Jan. 4, 1995, Brown, G., Shute, R. E.
WO 95/00472, Jan. 5, 1995, Brewster, A. G., et al.
or b) is a template which is defined analogously to the templates from the series of fibrinogen receptor antagonists and which is taken from the following patent applications:

Smithkline Beecham Corp.
WO 96/00574, Jan. 11, 1996, Cousins, R. D., et al.
Fujisawa Pharmaceutical Co.
WO 95/29907, Nov. 9, 1995, Kawai, Y., et al.
Eli Lilly
U.S. Pat. No. 5,488,058, Jan. 30, 1996, Palkowitz, A. D., et al.
U.S. Pat. No. 5,484,798, Jan. 16, 1996, Bryant, H. U., et al.; or also is one of those templates which can be derived structurally from the templates which are described in the above patent applications, patent documents and publications;

F is defined like D;

G is

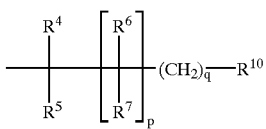

$R^2$ and $R^3$ are, independently of each other, H, $(C_1-C_{10})$-alkyl, which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $R^8OC(O)R^9$, $R^8R^8NC(O)R^9$ or $R^8C(O)R^9$;

$R^4$, $R^5$, $R^6$ and $R^7$ are, independently of each other, H, fluorine, OH, $(C_1-C_8)$-alkyl, $(C_3-C_{14})$-cycloalkyl, $(C_3-C_{14})$-cycloalkyl-$(C_1-C_8)$-alkyl, or $R^8OR^9$, $R^8SR^9$, $R^8CO_2R^9$, $R^8OC(O)R^9$, $R^8-(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is H, $(C_1-C_8)$-alkyl, $(C_3-C_{14})$-cycloalkyl, $(C_3-C_{14})$-cycloalkyl-$(C_1-C_8)$-alkyl, $(C_5-C_{14})$-aryl or $(C_5-C_{14})$-aryl-$(C_1-C_8)$-alkyl, where the alkyl radicals can be substituted, once or more than once, by fluorine;

$R^9$ is a direct linkage or $(C_1-C_8)$-alkanediyl;

$R^{10}$ is $C(O)R^{11}$, $C(S)R^{11}$, $S(O)_nR^{11}$, $P(O)(R^{11})_n$ or a four-membered to eight-membered, saturated or unsaturated heterocycle which contains 1, 2, 3 or 4 heteroatoms from the group N, O and S, such as tetrazolyl, imidazolyl, pyrazolyl, oxazolyl or thiadiazolyl;

$R^{11}$ is OH, $(C_1-C_8)$-alkoxy, $(C_5-C_{14})$-aryl-$(C_1-C_8)$-alkoxy, $(C_5-C_{14})$-aryloxy, $(C_1-C_8)$-alkylcarbonyloxy-$(C_1-C_4)$-alkoxy, $(C_5-C_{14})$-aryl-$(C_1-C_8)$-alkylcarbonyloxy-$(C_1-C_6)$-alkoxy, $NH_2$, mono- or di-$((C_1-C_8)$-alkyl)-amino, $(C_5-C_{14})$-aryl-$(C_1-C_8)$-alkylamino, $(C_1-C_8)$-dialkylaminocarbonylmethyloxy, $(C_5-C_{14})$-aryl-$(C_1-C_8)$-dialkylaminocarbonylmethyloxy or $(C_5-C_{14})$-arylamino or the radical of an L-amino acid or D-amino acid;

$R^{12}$, $R^{13}$, $R^{14}$ and $R^{15}$ are, independently of each other, H, $(C_1-C_{10})$-alkyl which is optionally substituted, once or more than once, by fluorine, $(C_3-C_{12})$-cycloalkyl, $(C_3-C_{12})$-cycloalkyl-$(C_1-C_8)$-alkyl, $(C_5-C_{14})$-aryl, $(C_5-C_{14})$-aryl-$(C_1-C_8)$-alkyl, $H_2N$, $R^8ONR^9$, $R^9OR^9$, $R^8OC(O)R^9$, $R^8R^8NR^9$, $R^8-(C_5-C_{14})$-aryl-$R^9$, $HO-(C_1-C_8)$-alkyl-$N(R^2)R^9$, $R^8N(R^2)C(O)R^9$, $R^8C(O)N(R^2)R^9$, $R^8C(O)R^9$, $R^2R^3N-C(=NR^2)-NR^2$, $R^2R^3N-C(=NR)$, $=O$, or $=S$;

where two adjacent substituents from $R^{12}$ to $R^{15}$ can also together be $-OCH_2O-$, $-OCH_2CH_2O-$ or $-OC(CH_3)O-$;

n is 1 or 2;

p and q are, independently of each other, 0 or 1;

in all their stereoisomeric forms and mixtures thereof in all proportions, and their physiologically tolerated salts with compounds being excepted in which E a) is a 6-membered aromatic ring system which can contain up to 4 N atoms and which can be substituted by from 1 to 4 identical or different arbitrary substituents, or b) is 4-methyl-3-oxo-2,3,4,5-tetrahydro-1-H-1,4-benzodiazepine.

A template from the series of fibrinogen receptor antagonists is understood to mean the central part of the molecular structure (of a fibrinogen receptor antagonist) to which, in the case of the fibrinogen receptor antagonists, a basic group and an acidic group are linked by way of spacers, with the basic and/or acidic group being present in protected form (prodrug) where appropriate.

In the fibrinogen receptor antagonists, the basic group is generally an N-containing group, such as amidine or guanidine, while the acidic group is generally a carboxyl function, with it being possible for the basic group and the acidic group to be present in each case in protected form.

A fibrinogen receptor antagonist is an active compound which inhibits the binding of fibrinogen to the blood platelet receptor GPIIbIIIa.

A fibrinogen receptor antagonist comprises a central part (template) to which a basic group and an acidic group are linked by way of spacers, with the basic group and/or acidic group being present in protected form (prodrug), where appropriate.

Alkyl radicals may be straight-chain or branched. This also applies if they carry substituents or appear as the substituents of other radicals, for example in alkoxy, alkoxycarbonyl or aralkyl radicals. Examples of suitable $(C_1-C_{10})$-alkyl radicals are: methyl, ethyl, propyl, butyl, pentyl, hexyl, heptyl, octyl, decyl, isopropyl, isopentyl, neopentyl, isohexyl, 3-methylpentyl, 2,3,5-trimethylhexyl, sec-butyl and tert-pentyl. Preferred alkyl radicals are methyl, ethyl, propyl, isopropyl, butyl, isobutyl, sec-butyl and tert-butyl.

Alkenyl and alkynyl radicals may also be straight-chain or branched. Examples of alkenyl radicals are vinyl, 1-propenyl, allyl, butenyl and 3-methyl-2-butenyl, while examples of alkynyl radicals are ethynyl, 1-propynyl or propargyl.

Cycloalkyl radicals may be monocyclic or polycyclic, e.g. bicyclic or tricyclic. Examples of monocyclic cycloalkyl radicals are cyclopropyl, cyclobutyl, cyclopentyl, cyclohexyl, cycloheptyl, cyclooctyl and cyclododecyl which, however, can also be substituted by, for example, $(C_1-C_4)$-alkyl. 4-Methylcyclohexyl and 2,3-dimethylcyclopentyl may be mentioned as examples of substituted cycloalkyl radicals.

Cyclodecane and cyclododecane are examples of parent substances of the monocyclic $(C_{10}-C_{14})$-cycloalkyl radicals in $R^4$, $R^5$, $R^6$ and $R^7$.

Bicyclic and tricyclic cycloalkyl radicals may be unsubstituted or substituted, in any suitable position, by one or more oxo groups and/or one or more identical or different $(C_1-C_4)$-alkyl groups, e.g. methyl groups or isopropyl groups, preferably methyl groups. The free bond of the bicyclic or tricyclic radical can be located in any position in the molecule; the radical can consequently be bonded via a bridgehead atom or via an atom in a bridge. The free bond can also be located in any stereochemical position, for example in an exo position or an endo position.

An example of a bicyclic ring system is decalin (decahydronaphthalene), while an example of a system substituted by an oxo group is 2-decanone.

Examples of parent substances of bicyclic ring systems are norbornane (=bicyclo[2.2.1]heptane), bicyclo[2.2.2]octane and bicyclo[3.2.1]octane. An example of a system which is substituted by an oxo group is camphor (=1,7,7-trimethyl-2-oxobicyclo[2.2.1]heptane).

Examples of parent substances of tricyclic systems are twistane (=tricyclo[4.4.0.0$^{3,8}$]decane, adamantane (=tricyclo[3.3.1.1$^{3,7}$]decane), noradamantane (=tricyclo[3.3.1.0$^{3,7}$]nonane), tricyclo[2.2.1.0$^{2,6}$]heptane, tricyclo[5.3.2.0$^{4,9}$]dodecane, tricyclo[5.4.0.0$^{2,9}$]undecane or tricyclo[5.5.1.0$^{3,11}$]tridecane.

Examples of parent substances of tricyclic $(C_{10}-C_{14})$-cycloalkyl radicals in $R^4$, $R^5$, $R^6$ and $R^7$ are twistane (=tricyclo[4.4.0.0$^{3,8}$]decane, adamantane (=tricyclo[3.3.1.1$^{3,7}$]nonane), tricyclo[5.3.2.0$^{4,9}$]dodecane, tricyclo[5.4.0.0$^{2,9}$]undecane or tricyclo[5.5.1.0$^{3,11}$]tridecane.

Halogen is fluorine, chlorine, bromine or iodine.

Examples of 6-membered aromatic ring systems are phenyl, pyridyl, pyridazinyl, pyrimidinyl, pyrazinyl, 1,3,5-triazinyl, 1,2,4-triazinyl, 1,2,3-triazinyl and tetrazinyl.

Aryl is, for example, phenyl, naphthyl, biphenylyl, anthryl or fluoroenyl, with 1-naphthyl, 2-naphthyl and, in particular, phenyl being preferred. Aryl radicals, in particular phenyl radicals, may be substituted, once or more than once, preferably once, twice or three times, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, —OCH$_2$CH$_2$O—, —OC(CH$_3$)$_2$O—, cyano, hydroxycarbonyl, aminocarbonyl, $(C_1-C_4)$-alkoxycarbonyl, phenyl, phenoxy, benzyl, benzyloxy, (R$^{17}$O)$_2$P(O), (R$^{17}$O)$_2$P(O)—O— or tetrazolyl, where R$^{17}$ is H, $(C_1-C_{10})$-alkyl, $(C_6-C_{14})$-aryl or $(C_6-C_{14})$-aryl-$(C_1-C_8)$-alkyl.

In monosubstituted phenyl radicals, the substituent can be located in the 2, 3 or 4 position, with the 3 and 4 positions being preferred. If phenyl is substituted twice, the substituents can be in the 1, 2 or 1, 3 or 1, 4 positions relative to each other. The two substituents in phenyl radicals which are substituted twice are preferably arranged in the 3 and 4 positions, based on the linkage site.

Aryl groups can also be monocyclic or polycyclic aromatic ring systems in which from 1 to 5 carbon atoms can be replaced by from 1 to 5 heteroatoms, such as 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or β-carbolinyl, or a benzo-fused, cyclopenta-, cyclohexa- or cyclohepta-fused derivative of these radicals. These heterocycles can be substituted by the same substituents as the abovementioned carbocyclic aryl systems.

Of these aryl groups, preference is given to monocyclic or bicyclic aromatic ring systems which have from 1 to 3 heteroatoms from the group N, O and S and which can be substituted by from 1 to 3 substituents selected from the group consisting of $(C_1-C_6)$-alkyl, $(C_1-C_6)$-alkoxy, F, Cl, NO$_2$, NH$_2$, CF$_3$, OH, $(C_1-C_4)$-alkoxycarbonyl, phenyl, phenoxy, benzyloxy or benzyl.

In this context, particular preference is given to monocyclic or bicyclic aromatic 5-membered to 10-membered ring systems which have from 1 to 3 heteroatoms from the group N, O and S and which can be substituted by from 1 to 2 substituents from the group consisting of $(C_1-C_4)$-alkyl, $(C_1-C_4)$-alkoxy, phenyl, phenoxy, benzyl or benzyloxy.

L- or D-amino acids can be natural or unnatural amino acids. α-Amino acids are preferred. The following may be mentioned by way of example (cf. Houben-Weyl, Methoden der organischen Chemie [Methods of Organic Chemistry], Volume XV/1 and 2, Georg Thieme Verlag, Stuttgart, 1974):

Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hpro, hser, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (chg), cyclohexylalanine (Cha), 2-thienylalanine (Thia), 2,2-diphenylaminoacetic acid, 2-(p-tolyl)-2-phenylaminoacetic acid and 2-(p-chlorophenyl)aminoacetic acid; and also:

pyrrolidine-2-carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]decane-3-carboxylic acid; spiro(bicyclo-[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid;

tetrahydrothiazole-4-carboxylic acid; isoxazolidine-3-carboxylic acid; pyrazolidine-3-carboxylic acid and hydroxypyrrolidine-2-carboxylic acid, all of which can optionally be substituted (see the following formulae):

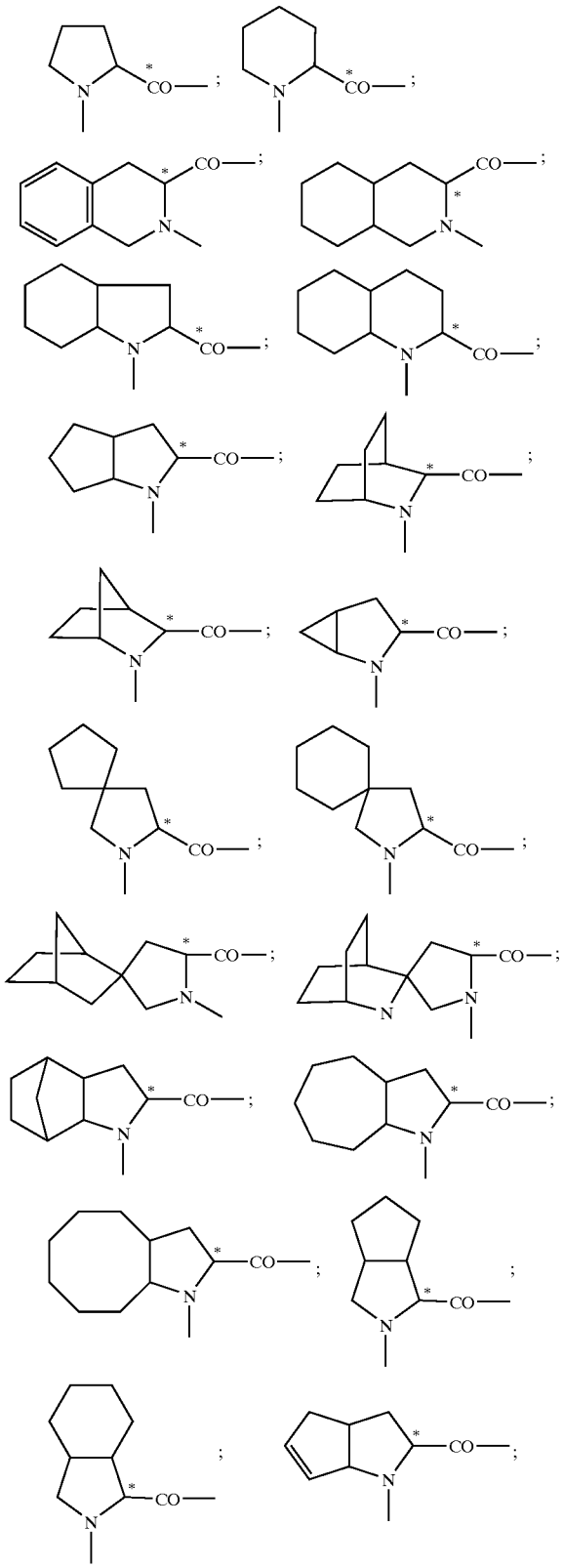

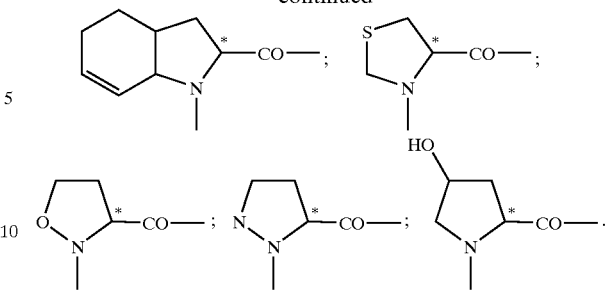

The heterocycles on which the abovementioned radicals are based are disclosed, for example, in U.S. Pat. Nos. 4,344,949; 4,374,847; 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

In addition, the amino acids can also be present as esters or amides, such as methyl esters, ethyl esters, isopropyl esters, isobutyl esters, tert-butyl esters, benzyl esters, unsubstituted amide, ethylamide, semicarbazide or ω-amino-$(C_2-C_8)$-alkylamide.

Functional groups in the amino acids may be present in protected form. Suitable protecting groups, such as urethane protecting groups, carboxyl protecting groups and side-chain protecting groups, are described in Hubbuch, Kontakte (Merck) 1979, No. 3, pages 14 to 23 and in Büllesbach, Kontakte (Merck) 1980, No. 1, pages 23 to 35. Those which may, in particular, be mentioned are: Aloc, Pyoc, Fmoc, Tcboc, Z, Boc, Ddz, Bpoc, Adoc, Msc, Moc, $Z(NO_2)$, $Z(Hal_n)$, Bobz, Iboc, Adpoc, Mboc, Acm, tert-butyl, OBzl, ONbzl, OMbzl, Bzl, Mob, Pic, Trt.

Physiologically tolerated salts of the compounds of the formula I are, in particular, pharmaceutically utilizable or nontoxic salts. Such salts are formed, for example, from compounds of the formula I which contain acidic groups, e.g. carboxyl, with alkali metals or alkaline earth metals, such as Na, K, Mg and Ca, and also with physiologically tolerated organic amines, such as triethylamine, ethanolamine or tris-(2-hydroxyethyl)amine. Compounds of the formula I which contain basic groups, e.g. an amino group, an amidino group or a guanidino group, form salts with inorganic acids, such as hydrochloric acid, sulfuric acid or phosphoric acid, and with organic carboxylic acids or sulfonic acids, such as acetic acid, citric acid, benzoic acid, maleic acid, fumaric acid, tartaric acid, lactic acid, methanesulfonic acid or p-toluenesulfonic acid.

The novel compounds of the formula I may contain optically active carbon atoms, which, independently of each other, can have R or S configurations, and they consequently may be present in the form of pure enantiomers or pure diastereomers or in the form of enantiomeric mixtures or diastereomeric mixtures. The present invention relates both to pure enantiomers and enantiomeric mixtures in all proportions and to diastereomers and diastereomeric mixtures in all proportions.

The novel compounds of the formula I may be present, independently of each other, as E/Z isomeric mixtures. The present invention relates both to pure E and Z isomers and to E/Z isomeric mixtures. Diastereomers, including E/Z isomers, can be separated into the individual isomers by means of chromatography. Racemates can be separated into the two enantiomers either by means of chromatography on chiral phases or by means of racemate resolution. The present invention moreover includes all solvates of compounds of the formulae I and Ia, for example hydrates or adducts with alcohols, and also derivatives of the compounds of the formulae I and Ia, for example esters, prodrugs and metabolites, which act like the compounds of the formulae I and Ia.

In addition to this, the novel compounds of the formula I may contain mobile hydrogen atoms, that is they may be present in different tautomeric forms. The present invention also relates to all these tautomers.

Preference is given to compounds of the formula I which are selective vitronectin receptor antagonists, particularly in relation to the fibrinogen receptor, i.e. which are stronger inhibitors of the vitronectin receptor than of the fibrinogen receptor.

Preference is given, in particular, to compounds of the formula I which are selective vitronectin receptor antagonists and in which the distance between $R^{10}$ and the first N atom in $A_1$ is from 12 to 13, and in $A_2$ from 11 to 12, covalent bonds along the shortest route between these atoms, as depicted below, by way of example, for $A_1 =$
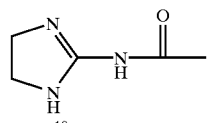
and $R^{10} = COOH$:
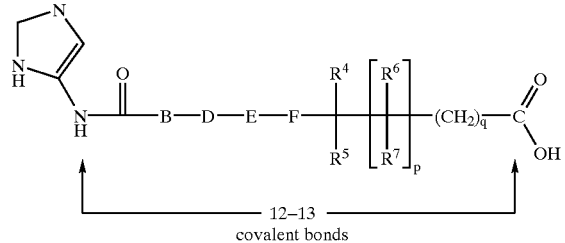

Preference is also given to compounds of the formula I in which at least one radical from the group $R^4$, $R^5$, $R^6$ and $R^7$ is a lipophilic radical.

Examples of lipophilic radicals in the group $R^4$, $R^5$, $R^6$ and $R^7$ are neopentyl, cyclohexyl, adamantyl, cyclohexyl-$(C_1-C_8)$-alkyl, adamantyl-$(C_1-C_8)$-alkyl, phenyl, naphthyl, phenyl-$(C_1-C_8)$-alkyl, naphthyl-$(C_1-C_8)$-alkyl, cyclohexylmethylcarbonylamino, 1-adamantylmethyloxycarbonylamino or benzyloxycarbonylamino, or, generally, radicals in which $R^8$ is, for example, neopentyl, cyclohexyl, adamantyl, cyclohexyl-$(C_1-C_8)$-alkyl, adamantyl-$(C_1-C_8)$-alkyl, phenyl, naphthyl, phenyl-$(C_1-C_8)$-alkyl or naphthyl-$(C_1-C_8)$-alkyl.

Preference is furthermore given to compounds of the formula I in which:

$A = A_1$ or $A_2$, with $A_1 = R^2R^3N-C(=NR^2)NR^2C(O)-$ or

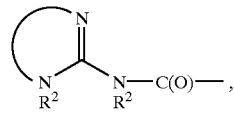

and $A_2 =$
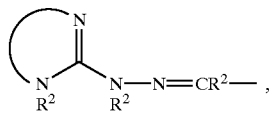

where, in $A_1$ or $A_2$

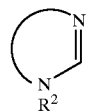

is a 5-membered to 10-membered monocyclic or polycyclic, aromatic or nonaromatic ring system which contains the grouping

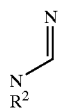

and, in addition, can contain from 1 to 4 heteroatoms from the group N, O and S and, where appropriate, can be substituted, once or more than once, by $R^{12}$, $R^{13}$, $R^{14}$ and $R^{15}$;

B is a direct linkage, —NH—, —O—, $(C_1-C_6)$-alkanediyl, $(C_5-C_8)$-arylene, $(C_5-C_6)$-cycloalkylene, —$CR^2=CR^3$—, —C≡C—, which can in each case be substituted, once or twice, by $(C_1-C_6)$-alkyl;

D is a direct linkage, $(C_1-C_8)$-alkanediyl, $(C_5-C_{10})$-arylene, —O—, —$NR^2$—, —CO—$NR^2$—, —$NR^2$—CO—, —$NR^2$—C(O)—$NR^2$—, —$NR^2$—C(S)—$NR^2$—, —OC(O)—, —C(O)O—, —CO—, —$S(O)_2$—, —$S(O)_2$—$NR^2$—, —$NR^2$—$S(O)_2$—, —S—, —$CR^2=CR^3$—, —C≡C—, —N=$CR^2$—, —$R^2C$=N—, which can in each case be substituted, once or twice, by $(C_1-C_8)$-alkyl, —$CR^2=CR^3$— or $(C_5-C_6)$-aryl, with it being possible, if B is a direct linkage, for D also to be a direct linkage or a radical as defined under D, which radical is substituted once or twice, as described under D, and is linked to B by way of one of these substituents;

E is a template from the fibrinogen receptor antagonist group, which template is taken from:

WO 93/08174, Oct. 15, 1991, Blackburn, B. K., et al.
U.S. Pat. No. 5,250,679, Oct. 5, 1993, Blackburn, B. K., et al.
U.S. Pat. No. 5,403,836, Apr. 4, 1995, Blackburn, B. K., et al.
WO 95/04057, Feb. 9, 1995, Blackburn, B. K., et al.
EP 0 655 439, Nov. 9, 1994, Denney, M. L., et al.
WO 94/18981, Sep. 1, 1994, Claremon, D. A., et al.
WO 94/08962, Apr. 28, 1994, Harmann, G. D., et al.
EP 0 668 278, Feb. 14, 1995, Juraszyk, H., et al.
WO 94/12478, Jun. 9, 1994, Keenan, B. Mc. C., et al.
EP 0 531 883, Sep. 3, 1992, Austel, V., et al.

F is defined like D;

G is

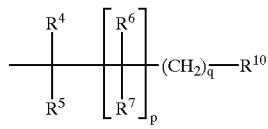

R² and R³ are, independently of each other, H, $(C_1-C_{10})$-alkyl, which is optionally substituted, once or more than once, by fluorine, $(C_3-C_8)$-cycloalkyl, $(C_3-C_8)$-cycloalkyl-$(C_1-C_6)$-alkyl, $(C_5-C_{12})$-aryl, $(C_5-C_{12})$-aryl-$(C_1-C_6)$-alkyl, $R^8OC(O)R^9$, $R^8R^8NC(O)R^9$ or $R^8C(O)R^9$;

$R^4$, $R^5$, $R^6$ and $R^7$ are, independently of each other, H, fluorine, OH, $(C_1-C_8)$-alkyl, $(C_5-C_{14})$-cycloalkyl, $(C_5-C_{14})$-cycloalkyl-$(C_1-C_8)$-alkyl, or $R^8OR^9$, $R^8SR^9$, $R^8CO_2R^9$, $R^8OC(O)R^9$, $R^8$—$(C_5-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$ or $R^8N(R^2)S(O)_nR^9$;

$R^8$ is H, $(C_1-C_6)$-alkyl, $(C_5-C_{14})$-cycloalkyl, $(C_5-C_{14})$-cycloalkyl-$(C_1-C_6)$-alkyl, $(C_5-C_{12})$-aryl or $(C_5-C_{12})$-aryl-$(C_1-C_6)$-alkyl, where the alkyl radicals can be substituted, once or more than once, by fluorine;

$R^9$ is a direct linkage or $(C_1-C_6)$-alkanediyl;

$R^{10}$ is $C(O)R^{11}$, $C(S)R^{11}$, $S(O)_nR^{11}$, $P(O)(R^{11})_n$ or a four-membered to eight-membered, saturated or unsaturated heterocycle which contains 1, 2, 3 or 4 heteroatoms from the group N, O and S;

$R^{11}$ is OH, $(C_1-C_6)$-alkoxy, $(C_5-C_{12})$-aryl-$(C_1-C_6)$-alkoxy, $(C_5-C_{12})$-aryloxy, $(C_1-C_6)$-alkylcarbonyloxy-$(C_1-C_4)$-alkoxy, $(C_5-C_{12})$-aryl-$(C_1-C_6)$-alkylcarbonyloxy-$(C_1-C_6)$-alkoxy, $NH_2$, mono- or di-$((C_1-C_6)$-alkyl)-amino, $(C_5-C_{12})$-aryl-$(C_1-C_6)$-alkylamino, $(C_1-C_6)$-dialkylaminocarbonylmethyloxy;

$R^{12}$, $R^{13}$, $R^{14}$ and $R^{15}$ are, independently of each other, H, $(C_1-C_8)$-alkyl which is optionally substituted, once or more than once, by fluorine, $(C_3-C_8)$-cycloalkyl, $(C_3-C_8)$-cycloalkyl-$(C_1-C_6)$-alkyl, $(C_5-C_{12})$-aryl, $(C_5-C_{12})$-aryl-$(C_1-C_6)$-alkyl, $H_2N$, $R^8ONR^9$, $R^8OR^9$, $R^8OC(O)R^9$, $R^8$—$(C_5-C_{12})$-aryl-$R^9$, $R^8R^8NR^9$, HO—$(C_1-C_8)$-alkyl-$N(R^2)R^9$, $R^8N(R^2)C(O)R^9$, $R^8C(O)N(R^2)R^9$, $R^8C(O)R^9$, $R^2R^3N$—$C(=NR^2)$, $R^2R^3N$—$C(=NR^2)$—$NR^2$, =O or =S; where two adjacent substituents from $R^{12}$ to $R^{15}$ can also together be —$OCH_2O$—, —$OCH_2CH_2O$— or —$OC(CH_3)_2O$—;

n is 1 or 2;

p and q are, independently of each other, 0 or 1;

in all their stereoisomeric forms and mixtures thereof in all proportions, and their physiologically tolerated salts.

Particular preference is given to compounds of the formula I in which:

A=$A_1$ or $A_2$, with $A_1$ =

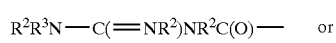

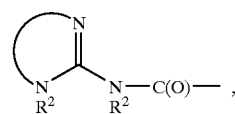

and $A_2$ =

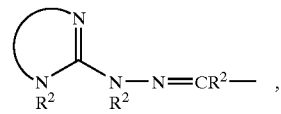

where, in $A_1$ or $A_2$ the radical

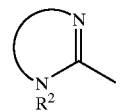

is a radical from the group

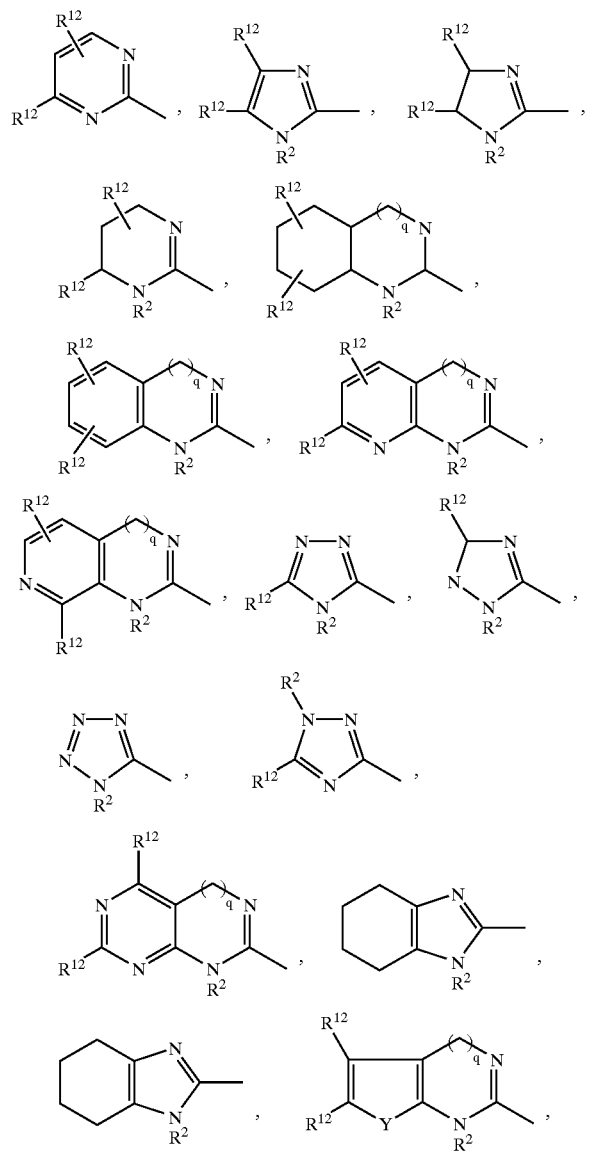

-continued

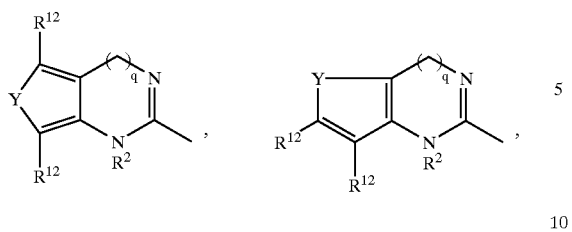

where $Y=NR^2$, O or S;

B is a direct linkage, $(C_1-C_6)$-alkanediyl, $(C_5-C_6)$-arylene, $-CR^2=CR^3-$, which can in each case be substituted, once or twice, by $(C_1-C_6)$-alkyl;

D is a direct linkage, $(C_1-C_6)$-alkanediyl, $(C_5-C_6)$-arylene, $-O-$, $-NR^2-$, $-NR^2-CO-$, $-NR^2-C(O)-NR^2-$, $-NR^2-C(S)-NR^2-$, $-OC(O)-$, $-CO-$, $-S(O)_2-NR^2-$, $-NR^2-S(O)-$, $-NR^2-S(O)_2-$ or $-CR^2=CR^3-$ which can in each case be substituted, once or twice, by $(C_1-C_6)$-alkyl, $-CH=CH-$ or phenyl; with it being possible, if B is a direct linkage, for D also to be a direct linkage or a radical as defined under D, which radical is substituted once or twice, as described under D, and is linked to B by way of one of these substituents;

E a) is a template from WO 93/08174, U.S. Pat. No. 5,250,679, 5,403,836 or 5,565,449, specifically:

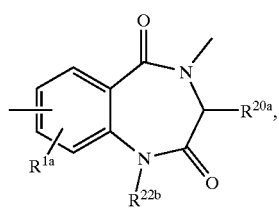

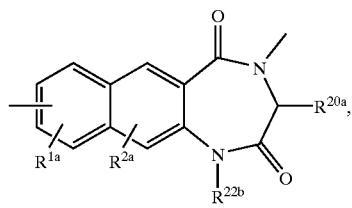

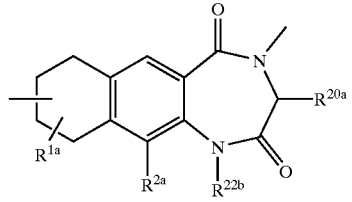

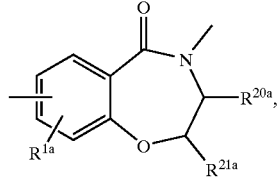

-continued

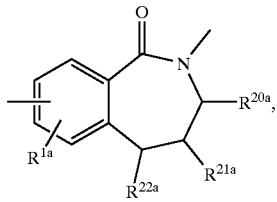

where $R^{1a}$, $R^{2a}$, $R^{20a}$, $R^{21a}$ and $R^{22a}$ are defined like $R^1$, $R^2$, $R^{20}$, $R^{21}$ and $R^{22}$ in U.S. Pat. No. 5,403,836, column 249, lines 9–22; and column 252, line 66 to column 253, line 68, and consequently:

$R^{1a}$ and $R^{2a}$ are, independently of each other, from one to three groups from the series consisting of hydrogen, halogen, cyano, carboxamido, carbamoyloxy, formyloxy, formyl, azido, nitro, ureido, thioureido, hydroxyl, mercapto or sulfonamido, or an optionally substituted radical from the group consisting of $C_1-C_{12}$-alkyl, $C_2-C_{12}$-alkenyl, $C_3-C_{12}$-alkynyl, $C_3-C_{12}$-cycloalkyl, $C_6-C_{14}$-aryl, $C_6-C_{10}$-aryl-$C_1-C_8$-alkyl, $C_1-C_{12}$-alkyloxy, $C_6-C_{14}$-aryloxy and $C_1-C_{12}$-acylamino, where the substituents are a radical from the group consisting of halogen, cyano, azido, nitro, hydroxyl, mercapto, sulfonamido, ureido, thioureido, carboxamido, carbamoyloxy, formyloxy, formyl, $C_1-C_4$-alkoxy, phenyl and phenoxy;

$R^{20a}$ is hydrogen, halogen (fluorine, chlorine, bromine or iodine), $C_1-C_4$-alkoxy, $C_1-C_4$-alkyl, phenyl, benzyl or halogen-$C_1-C_4$-alkyl, $R^{21a}$ and $R^{22a}$ are, independently of each other,
1. hydrogen
2. $(C_1-C_{12})$-alkyl
3. $(C_6-C_{14})$-aryl,
4. $(C_3-C_{14})$-cycloalkyl,
5. $(C_1-C_{12})$-alkyl-$(C_6-C_{14})$-aryl,
6. $(C_1-C_{12})$-alkyl-$(C_3-C_{14})$-cycloalkyl, where the radicals defined under 2. to 6. can be substituted by one or more radicals from the group consisting of halogen (fluorine, chlorine, bromine or iodine); nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; $COR^{24a}$ or $CONR^{25}R^{26}$; where $R^{24a}$ is a radical from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy, such as acetylaminoethoxy, nicotinoylaminoethoxy, succinamidoethoxy or pivaloylethoxy; or $C_6-C_{12}$-aryl-$C_1-C_8$-alkoxy, where the aryl group can be optionally substituted by from one to three radicals selected from the group consisting of nitro, halogen, $C_1-C_4$-alkoxy, amino, hydroxyl, hydroxy-$C_2-C_8$-alkoxy or dihydroxy-$C_3-C_8$-alkoxy;

$R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or $R^{25}$ and $R^{26}$ together form a trimethylene, tetramethylene, pentamethylene or 3-oxopentamethylene radical;

7. $Q^2$—$L^3$, where
   $Q^2$ is hydrogen or $Q^1$; and
   $L^3$ is a chemical bond, $L^1$ or $L^2$;
     $Q^1$ is a substituted or unsubstituted, positively charged, nitrogen-containing radical,
     $L^1$ is a divalent radical which contains from 3 to 9 methylene groups, where from one to all the methylene groups can be replaced with one or more alkene groups, alkyne groups, aryl groups or functional groups containing heteroatoms from the group consisting of N, O or S, and
     $L^2$ is an optionally substituted, divalent radical; where preferred radicals for $Q^1$, $L^1$ and $L^2$ are those radicals as described in U.S. Pat. No. 5,403,836 in column 249, line 27 to column 251, line 6 ($Q^1$), column 251, line 7 to column 252, line 18 ($L^1$) and column 252, lines 19–45 ($L^2$);

and $R^{22b}$ is defined like $R^{22}$ in U.S. Pat. No. 5,565,449, column 296, line 38 to column 297, line 38, and is:
1. hydrogen
2. $(C_1-C_{12})$-alkyl
3. $(C_6-C_{14})$-aryl,
4. $(C_3-C_{14})$-cycloalkyl,
5. $(C_1-C_{12})$-alkyl-$(C_6-C_{14})$-aryl,
6. $(C_1-C_{12})$-alkyl-$(C_3-C_{14})$-cycloalkyl, where the radicals defined under 2. to 6. can be substituted by one or more radicals from the group consisting of halogen (fluorine, chlorine, bromine or iodine); nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; $COR^{24a}$ or $CONR^{25}R^{26}$; where
   $R^{24a}$ is a radical from the group consisting of $C_1-C_8$-alkoxy; $C_3-C_{12}$-alkenoxy; $C_6-C_{12}$-aryloxy; di-(($C_1-C_8$)-alkyl)-amino-$C_1-C_8$-alkoxy; acylamino-$C_1-C_8$-alkoxy, such as acetylaminoethoxy, nicotinoylaminoethoxy, succinamidoethoxy or pivaloylethoxy; or $C_6-C_{12}$-aryl-$C_1-C_8$-alkoxy, where the aryl group can optionally be substituted by from one to three radicals selected from the group consisting of nitro, halogen, $C_1-C_4$-alkoxy, amino, hydroxyl, hydroxy-$C_2-C_8$-alkoxy or dihydroxy-$C_3-C_8$-alkoxy;
   $R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or
   $R^{25}$ and $R^{26}$ together form a trimethylene, tetramethylene, pentamethylene or 3-oxopentamethylene radical;
7. $Q^2$—$L^3$, where
   $Q^2$ is hydrogen or $Q^1$; and
   $L^3$ is a chemical bond, $L^1$ or $L^2$;
     $Q^1$ is a substituted or unsubstituted, positively charged, nitrogen-containing radical,
     $L^1$ is a divalent radical which contains from 3 to 9 methylene groups, where from one to all the methylene groups can be replaced with one or more alkene radicals, alkyne radicals, aryl radicals or functional groups containing heteroatoms from the group consisting of N, O or S, and
     $L^2$ is an optionally substituted, divalent radical; where preferred radicals for $Q^1$, $L^1$ and $L^2$ are those radicals as described in U.S. Pat. No. 5,403,836 in column 289, line 9 to column 293, line 17 ($Q^1$), column 293, line 18 to column 295, line 28 ($L^1$) and column 295, line 29 to column 296, line 11 ($L^2$);

or b) is a template from WO 95/04057, specifically:

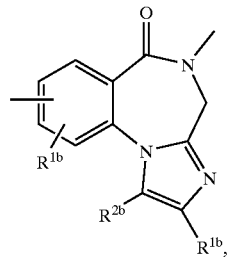
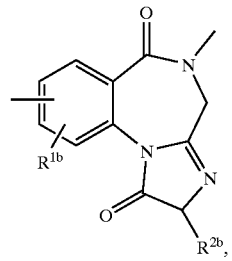
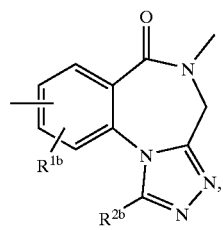
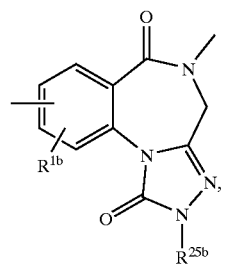
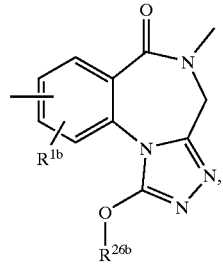
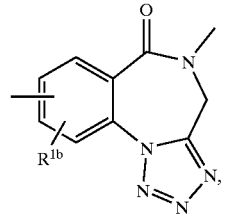
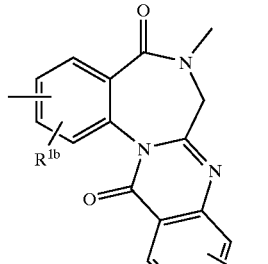
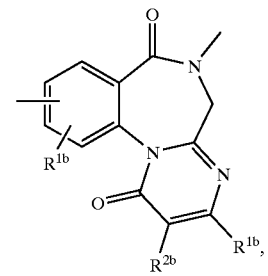
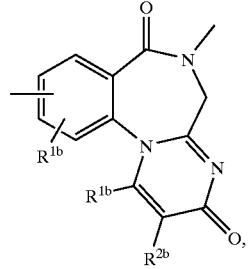
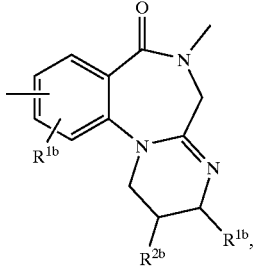

-continued

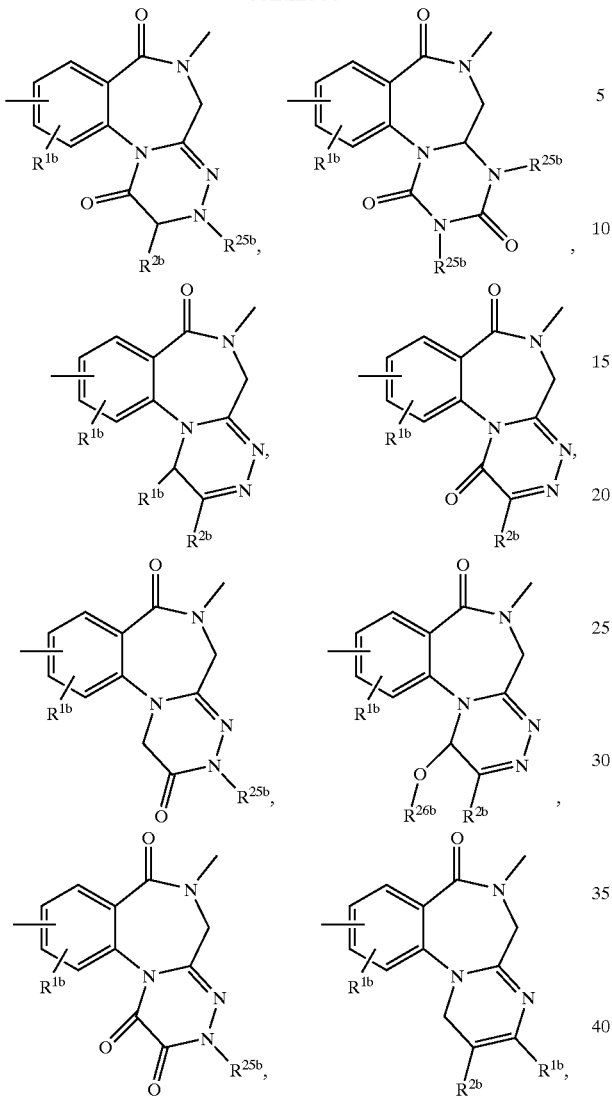

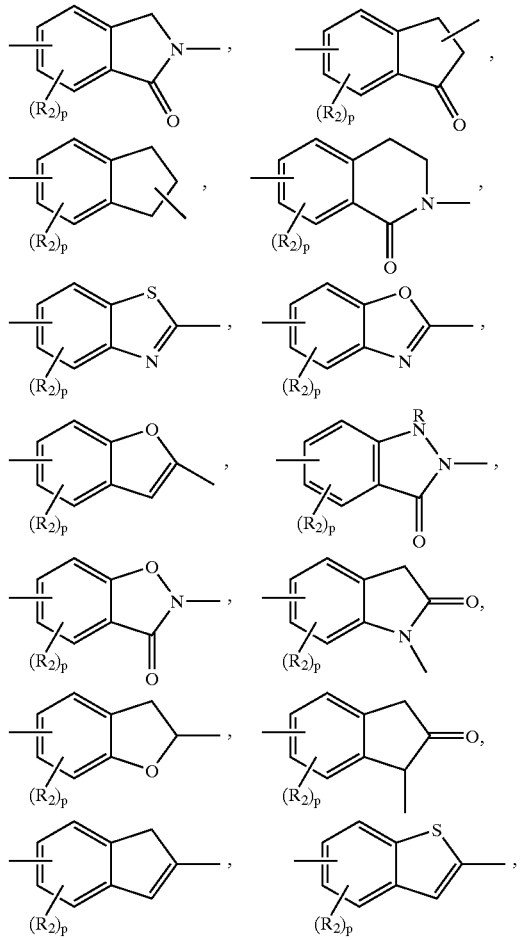

where $R^{1b}$ and $R^{2b}$ are defined like $R^1$ and $R^2$ in U.S. Pat. No. 5,403,836, column 249, lines 9–22; and are: $R^{1b}$ and $R^{2b}$ are, independently of each other, from one to three groups from the series consisting of hydrogen, halogen, cyano, carboxamido, carbamoyloxy, formyloxy, formyl, azido, nitro, ureido, thioureido, hydroxyl, mercapto or sulfonamido, or an optionally substituted radical from the group consisting of $C_1$–$C_{12}$-alkyl, $C_2$–$C_{12}$-alkenyl, $C_3$–$C_{12}$-alkynyl, $C_3$–$C_{12}$-cycloalkyl, $C_6$–$C_{14}$-aryl, $C_6$–$C_{10}$-aryl-$C_1$–$C_8$-alkyl, $C_1$–$C_{12}$-alkyloxy, $C_6$–$C_{14}$-aryloxy and $C_1$–$C_{12}$-acylamino, where the substituents are a radical from the group consisting of halogen, cyano, azido, nitro, hydroxyl, mercapto, sulfonamido, ureido, thioureido, carboxamido, carbamoyloxy, formyloxy, formyl, $C_1$–$C_4$-alkoxy, phenyl and phenoxy; and $R^{25b}$ and $R^{26b}$ are defined like $R^{25}$ and $R^{26}$ in U.S. Pat. No. 5,565,449 and:

$R^{25b}$ and $R^{26b}$ are, independently of each other, hydrogen, $C_1$–$C_{10}$-alkyl, $C_3$–$C_{10}$-alkenyl, $C_6$–$C_{14}$-aryl or $C_1$–$C_6$-alkyl-$C_6$–$C_{10}$-aryl, or $R^{25b}$ and $R^{26b}$ together form a trimethylene, tetramethylene, pentamethylene or 3-oxopentamethylene radical;

or c) is a template from EP-A 0 655 439, specifically where $(R_2)_p$ is bonded to one or more carbon atoms of the 6-membered ring and is, independently of each other, a radical from the group consisting of H, alkyl, halogen-substituted alkyl, hydroxyalkyl, alkenyl, alkynyl, cycloalkyl, aryl, aryloxy, aralkyl, hydroxyl, alkoxy, aralkoxy, carbamyl, amino, substituted amino, acyl, cyano, halogen, nitro and sulfo;

R is $(C_1$–$C_4)$-alkyl p is an integer from 1 to 3, or d) is a template from WO 94/12478, specifically

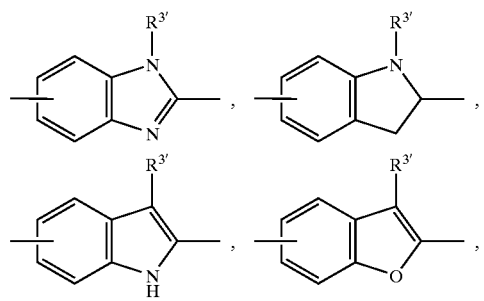

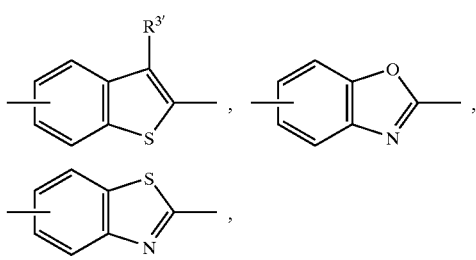

where R³' is hydrogen, (C₁–C₆)-alkyl or aryl-C₁–C₆-alkyl, or e) is a template from WO94/18981, specifically

1.

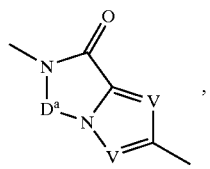

in which
V is CR^{7a} or N, and
D^a is CH₂, CH₂—CH₂, CH₂C(R^{7a})₂CH₂ or

2.

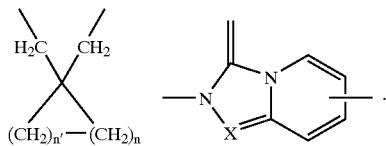

in which
X is CR^{3a} or N, where
R^{3a} is CN, C(O)N(R^{7a})R^{8a},

3.

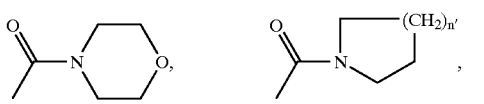

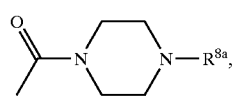

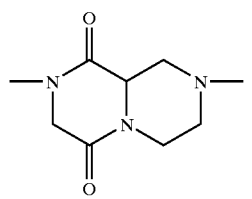
and

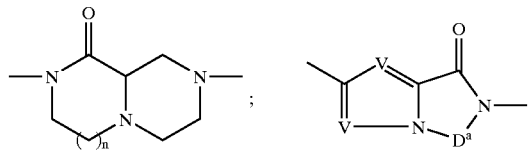

in which
V is CR^{7a} or N, and
D^a is CH₂, CH₂—CH₂, CH₂C(R^{7a})₂CH₂ or

4.

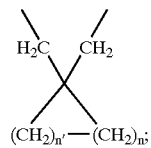
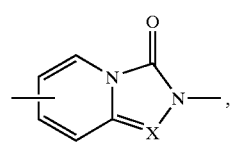

in which
X is CR^{3a} or N, in which
R^{3a} is CN, C(O)N(R^{7a})R^{8a},

5.

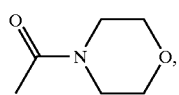
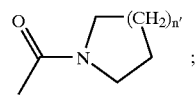

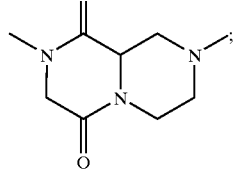

6.

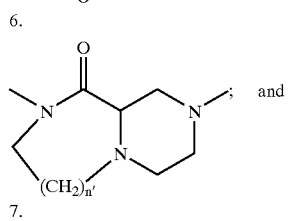
and

7.

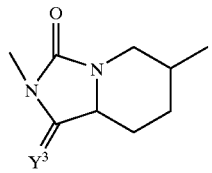

where
Y³ is O or H₂, and
R^{7a} is hydrogen; C₁–C₄-alkyl which is optionally substituted by OH or (C₁–C₄)-alkoxy; C₂–C₆-alkenyl which is optionally substituted by (C₁–C₄)-alkoxy; or OH (C₁–C₄)-alkylaryl; or aryl which is optionally substituted by identical or different radicals from the group consisting of halogen, (C₁–C₄)-alkoxy, hydroxyl or (C₁–C₄)-alkyl,
R^{8a} is hydrogen or C₁–C₄-alkyl,
n is an integer from 0 to 7, and
n' is an integer from 0 to 3;
or f) is a template from EP-A 0531 883, specifically

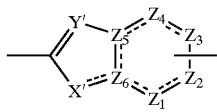

where:

X' is an oxygen, sulfur or nitrogen atom or an —NR$^{2b}$— group, where

R$^{2b}$ is a hydrogen atom, a straight-chain or branched alkyl group having from 1 to 15 carbon atoms, a straight-chain or branched alkenyl or alkynyl group having in each case from 3 to 10 carbon atoms, where the double bond or triple bond cannot connect directly to the nitrogen atom, a cycloalkyl or cycloalkylalkyl group having in each case from 3 to 7 carbon atoms in the cycloalkyl moiety, an aryl group, an alkyl group having from 2 to 6 carbon atoms which is substituted, from the β position to the nitrogen atom of the —NR$^{2b}$— group onwards, by an R$^{3b}$O—, (R$^{3b}$)$_2$N—, R$^{4b}$CO—NR$^{3b}$—, alkylsulfonyl-NR$^{3b}$—, arylsulfonyl-NR$^{3b}$, alkylsulfenyl, alkylsulfinyl, alkylsulfonyl or R$^{5b}$ group, or an alkyl group having from 1 to 6 carbon atoms which is substituted by one or two aryl groups, R$^{6b}$OCO—, (R$^{3b}$)$_2$NCO—, R$^{5b}$—CO—, R$^{3b}$O—CO-alkylene-NR$_3$—CO—, (R$^{3b}$)$_2$N—CO-alkylene-NR$^{3b}$—CO— or R$^{5b}$CO-alkylene-NR$^{3b}$—CO— group, in which R$^{3b}$ and R$^{5b}$ are defined as indicated below and R$^{6b}$ is a hydrogen atom, an alkyl group having from 1 to 6 carbon atoms, a cycloalkyl group having from 5 to 7 carbon atoms or an aralkyl group, Y' is an NO-group, a nitrogen atom or a methine group which is optionally substituted by an alkyl group, Z$_1$, Z$_2$, Z$_3$ und Z$_4$, which can be identical or different, are methine groups, carbon atoms, imino groups or nitrogen atoms, where at least one of the radicals Z$_1$ to Z$_4$ has to contain a carbon atom, and one or two methine groups which are adjacent to a nitrogen atom can in each case be replaced by carbonyl groups, Z$_5$ and Z$_6$ are in each case a carbon atom, or else one of the radicals Z$_5$ or Z$_6$ is a nitrogen atom and the other of the radicals Z$_5$ or Z$_6$ is a carbon atom, R$^{3b}$ is a hydrogen atom, an alkyl group having from 1 to 6 carbon atoms, or an aryl, aralkyl, carboxyalkyl or alkoxycarbonylalkyl group, R$^{4b}$ is a hydrogen atom, an alkyl or alkoxy group having in each case from 1 to 6 carbon atoms, or an aryl or aralkyl group having from 1 to 6 carbon atoms in the alkyl moiety, and R$^{5b}$ is an azetidino, pyrrolidino, hexamethylenimino or heptamethylenimino group or a piperidino group in which the methylene group in the 4 position can be replaced by an oxygen atom, by a sulfenyl, sulfinyl or sulfonyl group, or by an imino group which is substituted by an R$_3$, R$_4$CO—, alkylsulfonyl or arylsulfonyl group, where R$_3$ and R$_4$ are defined as mentioned above;

F is a direct linkage, (C$_1$–C$_6$)-alkanediyl, —O—, —CO—NR$^2$—, —NR$^2$—CO—, —NR$^2$—C(O)NR$^2$—, —OC(O)—, —C(O)O—, —CO—, —S(O)$_2$—, —S(O)$_2$NR$^2$—, —NR$^2$—S(O)$_2$—, —CR$^2$=CR$^3$—, —C≡C— which can in each case be substituted, once or twice, by (C$_1$–C$_6$)-alkyl;

G is 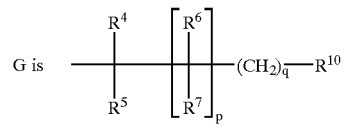

R$^2$ and R$^3$ are, independently of each other, H, (C$_1$–C$_6$)-alkyl which is optionally substituted, once or more than once, by fluorine, (C$_5$–C$_6$)-cycloalkyl, (C$_5$–C$_6$)-cycloalkyl-(C$_1$–C$_4$)-alkyl, (C$_5$–C$_{10}$)-aryl, (C$_5$–C$_{10}$)-aryl-(C$_1$–C$_4$)-alkyl, R$^8$OC(O)R$^9$, R$^8$R$^8$NC(O)R$^9$ or R$^8$C(O)R$^9$;

R$^4$, R$^5$, R$^6$ and R$^7$ are, independently of each other, H, fluorine, OH, (C$_1$–C$_6$)-alkyl, (C$_5$–C$_{14}$)-cycloalkyl, (C$_5$–C$_{14}$)-cycloalkyl-(C$_1$–C$_6$)-alkyl, or R$^8$OR$^9$, R$^8$CO$_2$R$^9$, R$^8$OC(O)R$^9$, R$^8$—(C$_5$–C$_{10}$)-aryl-R$^9$, R$^8$NHR$^9$, R$^8$R$^8$NR$^9$, R$^8$NHC(O)OR$^9$, R$^8$S(O)$_n$NHR$^9$, R$^8$OC(O)NHR$^9$, R$^8$C(O)NHR$^9$, R$^8$C(O)R$^9$, R$^8$NHC(O)NHR$^9$, R$^8$NHS(O)$_n$NHR$^9$, R$^8$NHC(O)R$^9$ or R$^8$NHS(O)$_n$R$^9$, where at least one radical from the group R$^4$, R$^5$, R$^6$ and R$^7$ is a lipophilic radical, such as benzyloxycarbonylamino, cyclohexylmethylcarbonylamino etc.;

R$^8$ is H, (C$_1$–C$_6$)-alkyl, (C$_5$–C$_{14}$)-cycloalkyl, (C$_5$–C$_{14}$)-cycloalkyl-(C$_1$–C$_4$)-alkyl, (C$_5$–C$_{10}$)-aryl or (C$_5$–C$_{10}$)-aryl-(C$_1$–C$_4$)-alkyl, where the alkyl radicals can be substituted by from 1 to 6 fluorine atoms;

R$^9$ is a direct linkage or (C$_1$–C$_6$)-alkanediyl;

R$^{10}$ is C(O)R$^{11}$;

R$^{11}$ is OH, (C$_1$–C$_6$)-alkoxy, (C$_5$–C$_{10}$)-aryl-(C$_1$–C$_6$)-alkoxy, (C$_5$–C$_{10}$)-aryloxy, (C$_1$–C$_6$)-alkylcarbonyloxy-(C$_1$–C$_4$)-alkoxy, (C$_5$–C$_{10}$)-aryl-(C$_1$–C$_4$)-alkylcarbonyloxy-(C$_1$–C$_4$)-alkoxy, NH$_2$ or mono- or di-(C$_1$–C$_6$-alkyl)-amino;

R$^{12}$ is H, (C$_1$–C$_6$)-alkyl which is optionally substituted, once or more than once, by fluorine, (C$_3$–C$_6$)-cycloalkyl, (C$_3$–C$_6$)-cycloalkyl-(C$_1$–C$_4$)-alkyl, (C$_5$–C$_{10}$)-aryl, (C$_5$–C$_{10}$)-aryl-(C$_1$–C$_4$)-alkyl, H$_2$N, R$^8$OR$^9$, R$^8$OC(O)R$^9$, R$^8$—(C$_5$–C$_{10}$)-aryl-R$^9$, R$^8$R$^8$NR$^9$, R$^8$NHC(O)R$^9$, R$^8$C(O)NHR$^9$, H$_2$N—C(=NH)—, H$_2$N—C(=NH)—NH— or =O; where two adjacent substituents R$^{12}$ can together also be —OCH$_2$O— or —OCH$_2$CH$_2$O—;

n is 1 or 2; and p and q are, independently of each other, 0 or 1;

in all their stereoisomeric forms and mixtures thereof in all proportions, and their physiologically tolerated salts.

Very particular preference is given to compounds of the formula I in which:

A=A$_1$ or A$_2$, with

A$_1$ = R$^2$R$^3$N—C(=NR$^2$)NR$^2$C(O)—, or

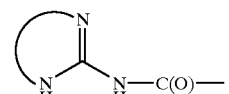

and A$_2$ = 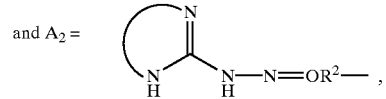

where, in $A_1$ or $A_2$ the radical

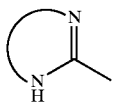

is a radical from the group

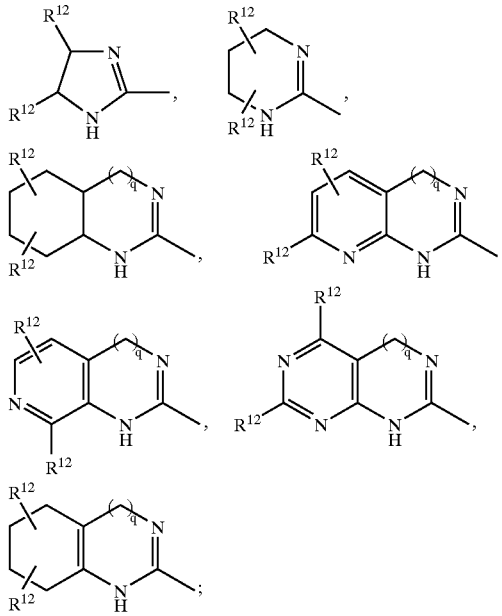

B is $(C_1-C_4)$-alkanediyl, phenylene, pyridinediyl, thiophenediyl, furandiyl or $-CR^2=CR^3-$, which can in each case be substituted, once or twice, by $(C_1-C_4)$-alkyl, D is a direct linkage, $(C_1-C_4)$-alkanediyl, $-O-$, $-NR^2-$, $-NR^2CO-$, $-C(O)-NR^2-$, $-NR^2-C(O)-NR^2-$, $-C(O)-$ or $-CR^2=CR^3-$, which can in each case be substituted, once or twice, by $(C_1-C_4)$-alkyl.

E a) is a template from WO 93/08174, U.S. Pat. No. 5,250,679, 5,403,836 or 5,565,449, specifically:

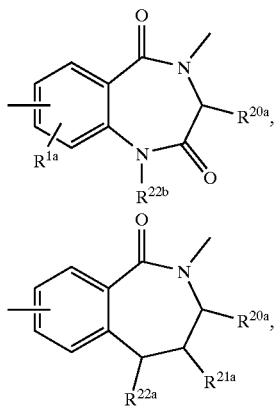

where $R^{1a}$, $R^{20a}$, $R^{21a}$, $R^{22a}$ and $R^{22b}$ are in this case:

$R^{1a}$ is, independently of each other, from one to three groups from the series consisting of hydrogen and halogen (fluorine, chlorine, bromine or iodine);

$R^{20a}$ is hydrogen;

$R^{21a}$ and $R^{22a}$ are, independently of each other,
1. hydrogen
2. $(C_1-C_6)$-alkyl
3. $(C_6-C_{12})$-aryl,
4. $(C_6-C_{12})$-cycloalkyl,
5. $(C_1-C_6)$-alkyl-$(C_6-C_{12})$-aryl,
6. $(C_1-C_6)$-alkyl-$(C_6-C_{12})$-cycloalkyl, where the radicals defined under 2. to 6. can be substituted by one or more radicals from the group consisting of fluorine, chlorine, hydroxyl, hydroxamate, sulfonamide, $(C_1-C_6)$-alkyl, $(C_6-C_{12})$-aryl, benzyl or $(C_6-C_{12})$-cycloalkyl;

$R^{22b}$ is
1. hydrogen
2. $(C_1-C_{12})$-alkyl
3. $(C_6-C_{14})$-aryl,
4. $(C_3-C_{14})$-cycloalkyl,
5. $(C_1-C_{12})$-alkyl-$(C_6-C_{14})$-aryl,
6. $(C_1-C_{12})$-alkyl-$(C_3-C_{14})$-cycloalkyl, where the radicals defined under 2. to 6. can be substituted by one or more radicals from the group consisting of halogen (fluorine, chlorine, bromine or iodine); nitro; hydroxyl; carboxyl; tetrazole; hydroxamate; sulfonamide; trifluoroimide; phosphonate; $C_1-C_6$-alkyl; $C_6-C_{14}$-aryl; benzyl; $C_3-C_{14}$-cycloalkyl; $COR^{24a}$ or $CONR^{25}R^{26}$; where $R^{24a}$ is a radical from the group consisting of $C_1-C_8$-alkoxy; $C_3-C_{12}$-alkenoxy; $C_6-C_{12}$-aryloxy; di-$C_1-C_8$-alkylamino-$C_1-C_8$-alkoxy; acylamino-$C_1-C_8$-alkoxy, such as acetylaminoethoxy, nicotinoylaminoethoxy, succinamidoethoxy or pivaloylethoxy; or $C_6-C_{12}$-aryl-$C_1-C_8$-alkoxy, where the aryl group can be optionally substituted by from one to three radicals selected from the group consisting of nitro, halogen, $C_1-C_4$-alkoxy, amino, hydroxyl, hydroxy-$C_2-C_8$-alkoxy and dihydroxy-$C_3-C_8$-alkoxy;

$R^{25}$ and $R^{26}$ are, independently of each other, hydrogen, $C_1-C_{10}$-alkyl, $C_3-C_{10}$-alkenyl, $C_6-C_{14}$-aryl or $C_1-C_6$-alkyl-$C_6-C_{10}$-aryl, or $R^{25}$ and $R^{26}$ together form a trimethylene, tetramethylene, pentamethylene or 3-oxopentamethylene radical;

7. $Q^2-L^3$, where
$Q^2$ is hydrogen or $Q^1$; and
$L^3$ is a chemical bond or $L^1$;
$Q^1$ is an amino, amidino, aminoalkylenimino, iminoalkylenamino or guanidino group, preferably an amidino group;
$L^1$ is $C_6-C_{14}$-aryl-$C_2-C_4$-alkynylene; $C_6-C_{14}$-aryl-$C_1-C_3$-alkylene; $C_6-C_{14}$-aryl-$C_1-C_3$-alkyloxyene or $-R^{14c}-CO-NR^{6c}R^{15c}$, where $R^{6c}$ is hydrogen, $C_1-C_4$-alkoxy, $C_1-C_4$-alkyl or halogen-$C_1-C_4$-alkyl;

$R^{14c}$ is a chemical bond, $C_1-C_8$-alkylene, $C_3-C_7$-cycloalkylene, $C_2-C_5$-alkenylene, $C_3-C_5$-alkynylene, $C_6-C_{10}$-arylene, $C_1-C_3$-alkyl-$C_6-C_{12}$-arylene, $C_1-C_2$-alkyl-$C_6-C_{10}$-aryl-$C_1-C_2$-alkylene, $C_6-C_{10}$-aryl-$C_1-C_2$-alkylene or $C_6-C_{10}$-aryloxy-$C_1-C_2$-alkylene, and $R^{15c}$ is a chemical bond, $C_1-C_4$-alkylene, $C_2-C_4$-alkenylene, $C_2-C_4$-alkynylene, $C_6-C_{10}$-arylene or $C_1-C_3$-alkyl-$C_6-C_{12}$-arylene;

or b) is a template from WO 95/04057, specifically:

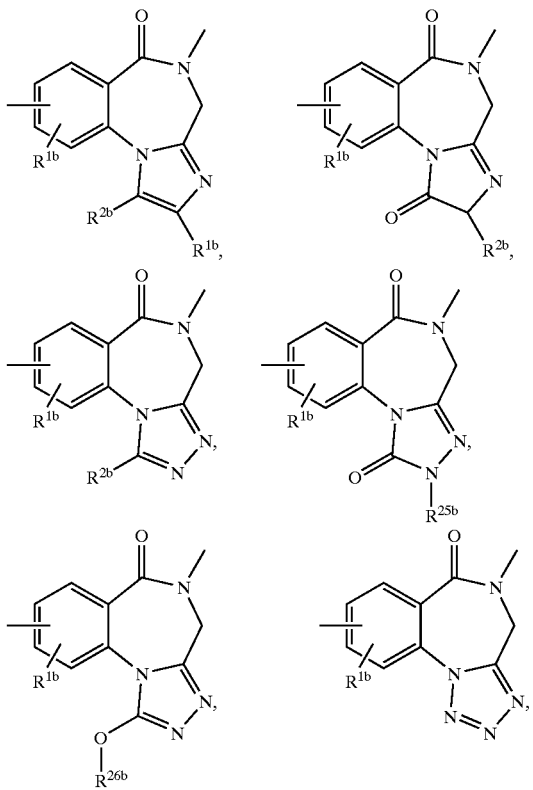

where $R^{1b}$, $R^{2b}$, $R^{25b}$ and $R^{26b}$ are in this case:

$R^{1b}$ and $R^{2b}$ are, independently of each other, from one to three groups from the series consisting of hydrogen and halogen (fluorine, chlorine, bromine or iodine); and $R^{25b}$ and $R^{26b}$ are, independently of each other hydrogen, $C_1$–$C_{10}$-alkyl, $C_3$–$C_{10}$-alkenyl, $C_6$–$C_{14}$-aryl or $C_1$–$C_6$-alkyl-$C_6$–$C_{10}$-aryl, or $R^{25b}$ and $R^{26b}$ together form a trimethylene, tetramethylene, pentamethylene or 3-oxopentamethylene radical;

or c) is a template from EP 0 655 439, specifically:

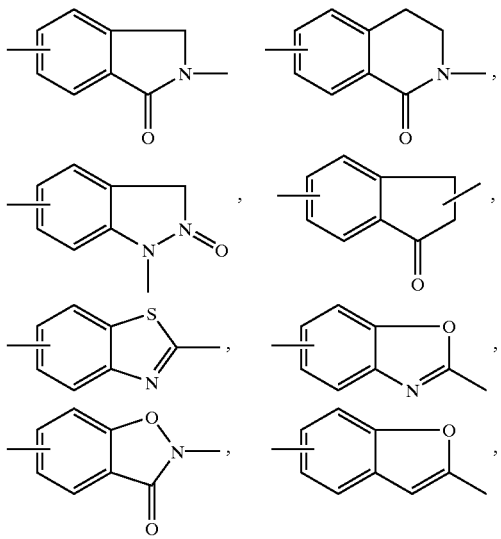

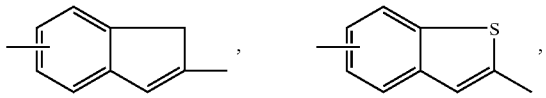

or d) is a template from WO 94/12478, specifically:

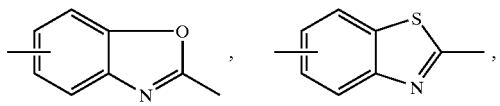

or e) is a template from WO 94/18981, specifically:

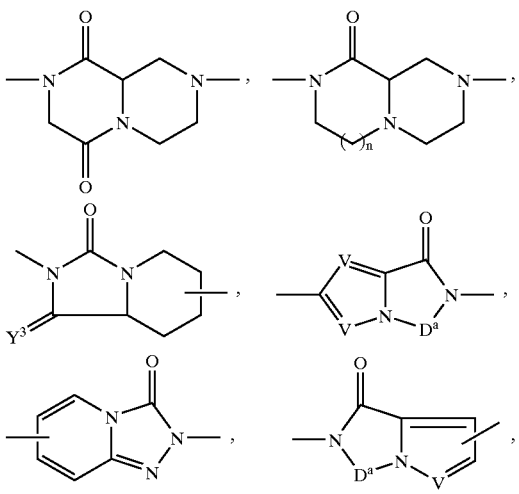

where $Y^3$, V and $D^a$ are defined as described above;
or f) is a template from EP 0 531 883, specifically:

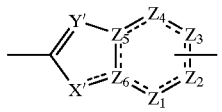

where:

X' is an oxygen, sulfur or nitrogen atom or an —$NR^{2b}$— group, where $R^{2b}$ is a hydrogen atom, a straight-chain or branched alkyl group having from 1 to 15 carbon atoms, a straight-chain or branched alkenyl or alkynyl group having in each case from 3 to 10 carbon atoms, where the double bond or triple bond cannot connect directly to the nitrogen atom, a cycloalkyl or cycloalkylalkyl group having in each case from 3 to 7 carbon atoms in the cycloalkyl moiety, an aryl group, an alkyl group having from 2 to 6 carbon atoms which is substituted, from the β position to the nitrogen atom of the —$NR^{2b}$— group onwards, by an $R^{3b}O$—, $(R^{3b})_2N$—, $R^{4b}CO$—$NR^{3b}$—, alkylsulfonyl-$NR^{3b}$—, arylsulfonyl-$NR^{3b}$—, alkylsulfenyl, alkylsulfinyl, alkylsulfonyl or $R^{5b}$ group, or an alkyl group having from 1 to 6 carbon atoms which is substituted by one or two aryl groups, $R^{6b}OCO$—, $(R^{3b})_2NCO$—, $R^{5b}$—CO—, $R^{3b}O$—CO-alkylene-$NR^{3b}$—CO—, $(R^{3b})_2N$—CO-alkylene-$NR^{3b}$—CO— or $R^{5b}CO$-alkylene-$NR^{3b}$—

CO— group, in which $R^{3b}$ and $R^{5b}$ are defined as indicated below and $R^{6b}$ is a hydrogen atom, an alkyl group having from 1 to 6 carbon atoms, a cycloalkyl group having from 5 to 7 carbon atoms or an aralkyl group, Y' is an NO-group, a nitrogen atom or a methine group which is optionally substituted by an alkyl group, $Z^1$, $Z_2$, $Z_3$ and $Z_4$, which can be identical or different, are methine groups, carbon atoms, imino groups or nitrogen atoms, where at least one of the radicals $Z_1$ to $Z_4$ has to contain a carbon atom, and one or two methine groups which are adjacent to a nitrogen atom can in each case be replaced by carbonyl groups, $Z_5$ and $Z_6$ are in each case a carbon atom, or else one of the radicals $Z_5$ or $Z_6$ is a nitrogen atom and the other of the radicals $Z_5$ or $Z_6$ is a carbon atom, $R^{3b}$ is a hydrogen atom, an alkyl group having from 1 to 6 carbon atoms, or an aryl, aralkyl, carboxyalkyl or alkoxycarbonylalkyl group, $R^{4b}$ is a hydrogen atom, an alkyl or alkoxy group having in each case from 1 to 6 carbon atoms, or an aryl or aralkyl group having from 1 to 6 carbon atoms in the alkyl moiety, and $R^{5b}$ is an azetidino, pyrrolidino, hexamethylenimino or heptamethylenimino group or a piperidino group in which the methyl group in the 4 position can be replaced by an oxygen atom, by a sulfenyl, sulfinyl or sulfonyl group, or by an imino group which is substituted by an $R^{3b}$, $R^{4b}$CO—, alkylsulfonyl or arylsulfonyl group, where $R^{3b}$ and $R^{4b}$ are defined as mentioned above;

F is a direct linkage, $(C_1-C_6)$-alkanediyl, —O—, —CO—NR$^2$—, —NR$^2$—CO—, —N—R$^2$—C(O)—NR$^2$—, —S(O)$_2$—NR$^2$, —NR$^2$—S(O)$_2$—, —CR=CR$^3$—, or —C≡C— which can in each case be substituted, once or twice, by $(C_1-C_4)$-alkyl;

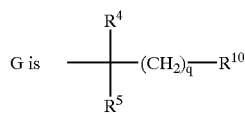

$R^2$ and $R^3$ are, independently of each other, H, $(C_1-C_4)$-alkyl, trifluoromethyl, pentafluoroethyl, $(C_5-C_6)$-cycloalkyl, $(C_5-C_6)$-cycloalkyl-$(C_1-C_4)$-alkyl, phenyl or benzyl;

$R^4$ is $(C_{10}-C_{14})$-cycloalkyl, $(C_{10}-C_{14})$-cycloalkyl-$(C_1-C_4)$-alkyl, or $R^{16}OR^9$, $R^{16}HNR^9$, $R^{16}NHC(O)OR^9$, $R^{16}S(O)_nNHR^9$, $R^{16}OC(O)NHR^9$, $R^{16}C(O)NHR^9$, $R^{16}C(O)R^9$, $R^{16}NHC(O)R^9$ or $R^{16}NHS(O)_nR^9$;

$R^5$ is H, $(C_1-C_6)$-alkyl, $(C_5-C_6)$-cycloalkyl, $(C_5-C_6)$-cycloalkyl-$(C_1-C_4)$-alkyl, trifluoromethyl, pentafluoroethyl, phenyl or benzyl;

$R^8$ is H, $(C_1-C_4)$-alkyl, $(C_5-C_6)$-cycloalkyl, $(C_5-C_6)$-cycloalkyl-$(C_1-C_2)$-alkyl, phenyl, benzyl, trifluoromethyl or pentafluoroethyl;

$R^9$ is a direct linkage or $(C_1-C_4)$-alkanediyl;

$R^{10}$ is $C(O)R^{11}$;

$R^{11}$ is OH, $(C_1-C_6)$-alkoxy, phenoxy, benzyloxy, $(C_1-C_4)$-alkylcarbonyloxy-$(C_1-C_4)$-alkoxy, NH$_2$ or mono- or di-$(C_1-C_6$-alkyl)amino;

$R^{12}$ is H, $(C_1-C_4)$-alkyl, trifluoromethyl, pentafluoroethyl, $(C_5-C_6)$-cycloalkyl, $(C_5-C_6)$-cycloalkyl-$(C_1-C_2)$-alkyl, $(C_5-C_6)$-aryl, $(C_5-C_6)$-aryl-$(C_1-C_2)$-alkyl, H$_2$N, $R^8R^8NR^9$, $R^8NHC(O)R^9$, H$_2$N—C(=NH) or H$_2$N—C(=NH)—NH—; where two adjacent substituents $R^{12}$ can together also be —OCH$_2$O— or —OCH$_2$CH$_2$O—;

$R^{16}$ is $(C_{10}-C_{14})$-cycloalkyl or $(C_{10}-C_{14})$-cycloalkyl-$(C_1-C_4)$-alkyl which can optionally be substituted, once or twice, by $(C_1-C_4)$-alkyl, trifluoromethyl, phenyl, benzyl, $(C_1-C_4)$-alkoxy, phenoxy, benzyloxy, =O or mono- or di-$((C_1-C_4)$-alkyl)-amino, where the cycloalkyl radicals are preferably 1-adamantyl or 2-adamantyl, which can be substituted as described above;

n is 1 or 2; and q is 0 or 1;

in all their stereoisomeric forms and mixtures thereof in all proportions, and their physiologically tolerated salts.

Preference is also given to compounds of the formula I, in which A, B, D, F and G are defined as above for the very particularly preferred compounds of the formula I and E is a template from WO 95/04057, EP 0655 439, WO 94/18981, WO 94/08962, EP 0668 278, WO 94/12478 or EP 0531 883, with the latter preferably being defined as above for the particularly preferred compounds of the formula I, and particularly preferably being defined as above for the very particularly preferred compounds of the formula I.

Another part of the subject-matter of the present invention is that a fibrinogen receptor antagonist, which is known per se, can be converted into a selective vitronectin receptor antagonist by replacing the basic group (together with spacer) of a fibrinogen receptor antagonist with A—B—D, which is defined as in formula I, with the distance between $R^{10}$ and the first N atom in $A_1$ being from 12 to 13, and in $A_2$ from 11 to 12, covalent bonds along the shortest route between these atoms.

In general, compounds of the formula I can be prepared, for example during the course of a convergent synthesis, by linking two or more fragments which can be derived retrosynthetically from the formula I. When preparing the compounds of the formula I, it can, in a general manner, be necessary, during the course of the synthesis, to use a protecting group strategy which is suited to the synthesis problem to temporarily block functional groups which could lead to undesirable reactions or side reactions in the particular synthesis step, as is known to the skilled person. The method of fragment linking is not restricted to the following examples but is generally applicable to syntheses of the compounds of the formula I.

For example, compounds of the formula I of the type

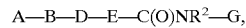

in which F=C(O)NR$^2$, can be prepared by condensing a compound of the formula II

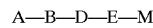         II, where M is hydroxycarbonyl, $(C_1-C_6)$-alkoxycarbonyl or activated carboxylic derivatives, such as acid chlorides, active esters or mixed anhydrides, with HNR$^2$—G.

In order to condense two fragments with the formation of an amide bond, use is advantageously made of the coupling methods, which are known per se, of peptide chemistry (see, for example, Houben-Weyl, Methoden der Organischen Chemie [Methods of Organic Chemistry], Volumes 15/1 and 15/2, Georg Thieme Verlag, Stuttgart, 1974). For this, it is, as a rule, necessary for non-reacting amino groups which are present to be protected with reversible protecting groups during the condensation. The same applies to carboxyl groups which are not involved in the reaction, which carboxyl groups are preferably employed as $(C_1–C_6)$-alkyl, benzyl or tert-butyl esters. There is no necessity to protect amino groups if the amino groups to be generated are still present as nitro or cyano groups and are only formed by means of hydrogenation after the coupling has taken place. After the coupling has taken place, the protecting groups which are present are eliminated in a suitable manner. For example, $NO_2$ groups (guanidino protection), benzyloxycarbonyl groups and benzyl esters can be removed by hydrogenation. The protecting groups of the tert-butyl type are eliminated under acid conditions, while the 9-fluorenylmethyloxycarbonyl radical is removed using secondary amines.

Compounds of the formula I in which $R^{10}=SO_2R^{11}$ are prepared, for example, by oxidizing compounds of the formula I in which $R^{10}=SH$ using methods which are known from the literature (cf. Houben-Weyl, Methoden der Organischen Chemie, Vol. E12/2, Georg Thieme Verlag, Stuttgart 1985, pp. 1058ff) to give compounds of the formula I in which $R^{10}=SO_3H$, from which the compounds of the formula I in which $R^{10}=SO_2R^{11}$ ($R^{11} \neq OH$) are then prepared directly or by way of corresponding sulfonyl halides by means of esterification or formation of an amide bond. Oxidation-sensitive groups in the molecule, such as amino, amidino or guanidino groups, are, if necessary, protected with suitable protecting groups before performing the oxidation.

Compounds of the formula I in which $R^{10}=S(O)R^{11}$ are prepared, for example, by converting compounds of the formula I in which $R^{10}=SH$ into the corresponding sulfide ($R^{10}=S^\ominus$) and then oxidizing with meta-chloroperbenzoic acid to give the sulfinic acids ($R^{10}=SO_2H$) (cf. Houben-Weyl, Methoden der Organischen Chemie, Vol. E11/1, Georg Thieme Verlag, Stuttgart 1985, pp. 618f), from which the corresponding sulfinic acid esters or amides, $R^{10}=S(O)R^{11}(R^{11}\neq OH)$, can be prepared using methods which are known from the literature. In a general manner, other methods known from the literature can also be used to prepare compounds of the formula I in which $R^{10}=S(O)_nR^{11}$ (n=1 or 2) (cf. Houben-Weyl, Methoden der Organischen Chemie, Vol. E11/1, Georg Thieme Verlag, Stuttgart 1985, pp. 618ff or Vol. E11/2, Stuttgart 1985, pp. 1055ff).

Compounds of the formula I in which $R^{10}=P(O)(R^{11})_n$ (n=1 or 2) are synthesized, using methods which are known from the literature (cf. Houben-Weyl, Methoden der Organischen Chemie, Vols. E1 and E2, Georg Thieme Verlag, Stuttgart 1982), from suitable precursors, with it being necessary to match the selected synthesis method to the target molecule.

Compounds of the formula I in which $R^{10}=C(S)R^{11}$ can be prepared using methods known from the literature (cf. Houben-Weyl, Methoden der Organischen Chemie, Vols. E5/1 and E5/2, Georg Thieme Verlag, Stuttgart 1985).

Compounds of the formula I in which $R^{10}=S(O)_nR^{11}$ (n=1 or 2), $P(O)(R^{11})_n$ (n=1 or 2) or $C(S)R^{11}$ may, of course, also be prepared by means of fragment linking, as described above, which approach is, for example, advisable when, for example, a (commercially available) aminosulfonic acid, aminosulfinic acid, aminophosphonic acid or aminophosphinic acid, or derivatives derived therefrom, such as esters or amides, are present in F—G of the formula I.

Compounds of the formula I in which $A=A_1=R^2R^3N-C(=NR^2)-NR^2-C(O)-$ or cyclic acylguanidines of the type

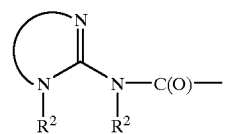

can be prepared, for example, by reacting a compound of the formula III $$Q(O)C-B-D-E-F-G \qquad \text{III}$$

in which Q is a leaving group which can readily be substituted nucleophilically, with the corresponding guanidine (derivative) of the type

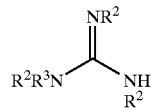

or the cyclic guanidine (derivative) of the type

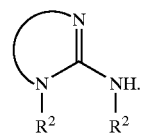

The activated acid derivatives of the formula III, in which Q is an alkoxy, preferably a methoxy, group, a phenoxy group, a phenylthio, methylthio or 2-pyridylthio group, or a nitrogen heterocycle, preferably 1-imidazolyl, are advantageously obtained, in a manner known per se, from the carboxylic acids (Q=OH) on which they are based or the carboxylic acid chorides (Q=Cl). The latter are in turn obtained, in a manner known per se, from the corresponding carboxylic acids (Q=OH), for example by means of reacting with thionyl chloride.

In addition to the carbonyl chlorides (Q=Cl), other activated acid derivatives of the Q(O)C-type can also be prepared, in a manner known per se, directly from the corresponding carboxylic acids (Q=OH), such as the methyl esters (Q=OCH$_3$) by treating with gaseous HCl in methanol, the imidazolides (Q=1-imidazolyl) by treating with carbonyldiimidazole [cf. Staab, Angew. Chem. Int. Ed. Engl. 1, 351–367 (1962)], and the mixed anhydrides (Q=C$_2$H$_5$OC(O)O or TosO) using Cl—COOC$_2$H$_5$ or tosyl chloride in the presence of triethylamine in an inert solvent. The carboxylic acids can also be activated with dicyclohexylcarbodiimide (DCCI) or with O-[(cyano(ethoxycarbonyl)methylen)amino]-1,1,3,3-tetramethyluronium tetrafluoroborate ("TOTU") [Weiss and Krommer, Chemiker-Zeitung 98, 817 (1974)] and other activation reagents which are customary in peptide chemistry. A number of suitable methods for preparing activated carboxylic acid derivatives of the formula II are given, with citation of source literature, in J. March, Advanced Organic Chemistry, Third Edition (John Wiley & Sons, 1985), p. 350.

An activated carboxylic acid derivative of the formula III is reacted with the relevant guanidine (derivative) in a manner known per se in a protic or aprotic, polar but inert organic solvent. In this context, methanol, isopropanol or tetrahydrofuran (THF), at temperatures of from 20° C. up to the boiling temperature of these solvents, have proved to be of value when the methyl esters (Q=OMe) are reacted with the relevant guanidines. Most reactions of compounds of the formula III with salt-free guanidines are advantageously carried out in aprotic inert solvents such as THF, dimethoxyethane and dioxane. However, when a base (such as NaOH) is employed, water can also be used as solvent when compounds of the formula III are reacted with guanidines. When Q=Cl, the reaction is advantageously carried out in the presence of an added acid-capturing agent, for example in the form of excess guanidine (derivative), in order to bind the hydrohalic acid.

Compounds of the formula I, in which $A=A_1=R^1R^2N-C(=NR^2)-NR^2-C(S)-$ or

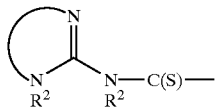

can be prepared as described for the synthesis of corresponding open-chain or cyclic acylguanidine (derivatives) by reacting a compound of the formula XI

in which Q is defined as above, with the corresponding guanidine (derivative) of the type

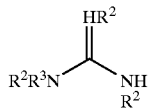

or with the cyclic guanidine (derivative) of the type

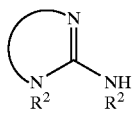

as described above.

Compounds of the formula I, in which $A=A_1$ is a sulfonylguanidine or sulfoxylguanidine of the type $R^2R^3N-C(=NR^2)-NR^2-S(O)_n-$ (n=1 or 2) or

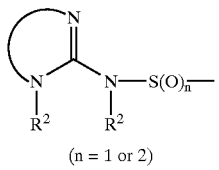

(n = 1 or 2)

are prepared, using methods which are known from the literature, by reacting $R^2R^3N-C(=NR^3)NR^2H$ or

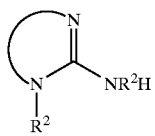

with sulfinic acid derivatives or sulfonic acid derivatives of the formula IV

in which Q is, e.g., Cl or $NH_2$, in analogy with S. Birtwell et al., J. Chem. Soc. (1946) 491 or Houben Weyl, Methoden der Organischen Chemie, Vol. E4, Georg Thieme Verlag, Stuttgart 1983; pp. 620 ff.

Compounds of the formula I in which F is $-R^2N-C(O)-NR^2-$ or $-R^2N-C(S)-NR^2-$ are prepared, for example, by reacting a compound of the formula VII

with an isocyanate OCN-G or isothiocyanate SCN-G using methods which are known from the literature.

Compounds of the formula I in which F is $-C(O)NR^2-$, $-SO_2NR^2-$ or $-C(O)O-$ can be obtained, for example, by reacting

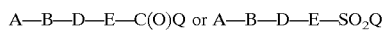

(Q is a leaving group which can readily be substituted nucleophilically, such as OH, Cl, OMe etc.) with $HR^2N-G$ or HO-G using methods known from the literature.

Compounds of the formula I, in which $A=A_2=$

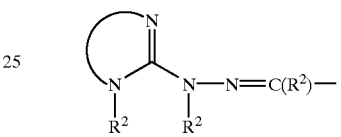

are prepared, for example, by condensing

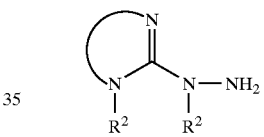

with ketones or aldehydes of the type $O=C(R^2)-$ or corresponding acetals or ketals using customary methods known from the literature, for example in analogy with N. Desideri et al., Arch. Pharm. 325 (1992) 773–777, A. Alves et al., Eur. J. Med. Chem. Chim. Ther. 21 (1986) 297–304, D. Heber et al., Pharmazie 50 (1995) 663–667, T. P. Wunz et al., J. Med. Chem. 30 (1987) 1313–1321, K.-H. Buchheit et al., J. Med. Chem. 38 (1995), 2331–2338.

The above guanyl hydrazones may result as E/Z isomeric mixtures, which can be resolved using customary chromatographic methods.

Compounds of the formula I, in which D is $-C\equiv C-$ can be prepared, for example, by reacting a compound of the formula IX

in which X=I or Br, with a compound of the type $A-B-C\equiv-CH$ in a palladium-catalyzed reaction, for example as described in A. Arcadi et al., Tetrahedron Lett. 1993, 34, 2813 or E. C. Taylor et al., J. Org. Chem. 1990, 55, 3222.

In an analogous manner, compounds of the formula I in which F is $-C\equiv C-$ can be prepared, for example, by linking compounds of the formula X

in which X is I or Br, with a compound of the type $HC\equiv C-G$ in a palladium-catalyzed reaction.

The fibrinogen receptor antagonist template E is synthesized as described in the relevant patents, patent applications or publications, with functional groups being incorporated into the template, or being attached to the template, during synthesis of the template or afterwards, preferably during synthesis of the template, which groups permit the subsequent linking-on of A—B—D and F—G by means of fragment linking, as described below, by way of example, for a template from WO 94/18981:

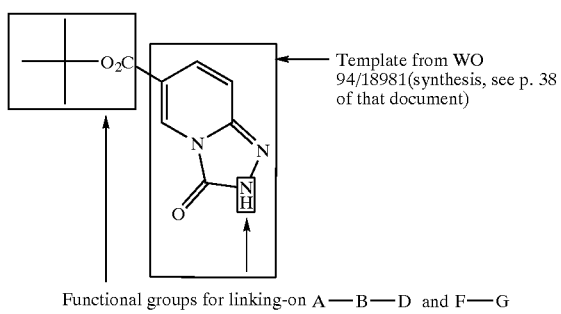

Functional groups for linking-on A—B—D and F—G

Example of the Linking-on of A—B—D and F—G

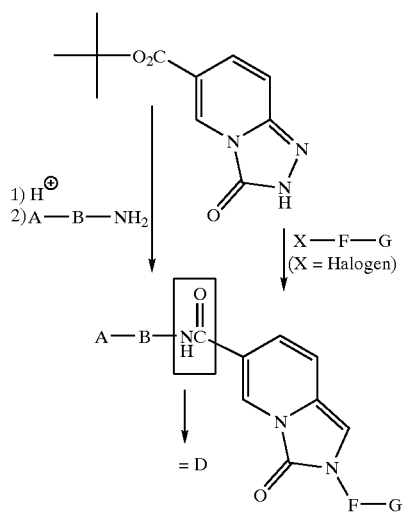

Preparation methods which are known from the literature are described, for example, in J. March, Advanced Organic Chemistry, Third Edition (John Wiley & Sons, 1985).

The compounds of the formula I, and their physiologically tolerated salts, may be administered to animals, preferably to mammals and, in particular, to humans, as drugs on their own, in mixtures with each other or in the form of pharmaceutical preparations which permit enteral or parenteral use and which comprise, as the active constituent, an effective dose of at least one compound of the formula I, or of a salt thereof, together with customary, pharmaceutically unobjectionable carrier and auxiliary substances. The preparations normally comprise from about 0.5 to 90% by weight of the therapeutically active compound.

The drugs may be administered orally, for example in the form of pills, tablets, lacquered tablets, coated tablets, granules, hard and soft gelatin capsules, solutions, syrups, emulsions, suspensions or aerosol mixtures. However, the administration can also be effected rectally, for example in the form of suppositories, or parenterally, for example in the form of injection or infusion solutions, microcapsules or rods, percutaneously, for example in the form of ointments or tinctures, or nasally, for example in the form of nasal sprays.

The pharmaceutical preparations are produced in a manner known per se, with pharmaceutically inert inorganic or organic carrier substances being used. Lactose, corn starch or derivatives thereof, talc, stearic acid or its salts, etc. can, for example, be used for preparing pills, tablets, coated tablets and hard gelatin capsules. Examples of carrier substances for soft gelatin capsules and suppositories are fats, waxes, semisolid and liquid polyols, natural or hardened oils, etc. Examples of suitable carrier substances for preparing solutions and syrups are water, sucrose, invert sugar, glucose, polyols, etc. Suitable carrier substances for preparing injection solutions are water, alcohols, glycerol, polyols, vegetable oils, etc. Suitable carrier substances for microcapsules, implants or rods are mixed polymers of glycolic acid and lactic acid.

In addition to the active compounds and carrier substances, the pharmaceutical preparations may also comprise additives, such as fillers, extenders, disintegrants, binders, glidants, wetting agents, stabilizers, emulsifiers, preservatives, sweeteners, dyes, flavorants or aromatizing substances, thickeners, diluents or buffering substances, and also solvents or solubilizing agents or agents for achieving a slow release effect, and also salts for altering the osmotic pressure, coating agents or antioxidants. They may also comprise two or more compounds of the formula I or their physiologically tolerated salts; they may furthermore comprise one or more different therapeutically active compounds in addition to at least one compound of the formula I.

The dose may be varied within wide limits and must be adjusted to the individual circumstances in each individual case.

In the case of oral administration, the daily dose may be from 0.01 to 100 mg/kg, preferably from 0.1 to 5 mg/kg, particularly from 0.3 to 0.5 mg/kg of bodyweight in order to achieve effective results. Also in the case of intravenous administration the daily dose is generally from about 0.01 to 100 mg/kg, preferably from 0.05 to 10 mg/kg of bodyweight. Particularly when administering relatively large quantities, the daily dose can be subdivided into several, e.g. 2, 3 or 4, parts which are administered separately. Where appropriate, it can be necessary to depart from the given daily dose in an upward or downward direction depending on the individual response.

Besides as active drug substances the compounds of the formula I may be used in diagnostic procedures, for example in in vitro diagnoses, or as tools in biochemical research when it is intended to inhibit the vitronectin receptor.

EXAMPLES

The products were identified by their mass spectra and/or NMR spectra.

Example 1

(2S)-3-[5-(2-Guanidinocarbonylethyl)-4,5,6,7-tetrahydro-4-oxopyrazolo[1,5-a]-pyrazine-2-carbonylamino]-2-[benzyloxycarbonylamino] propionic acid (1.8)

The synthesis was carried out in accordance with the following reaction sequence:

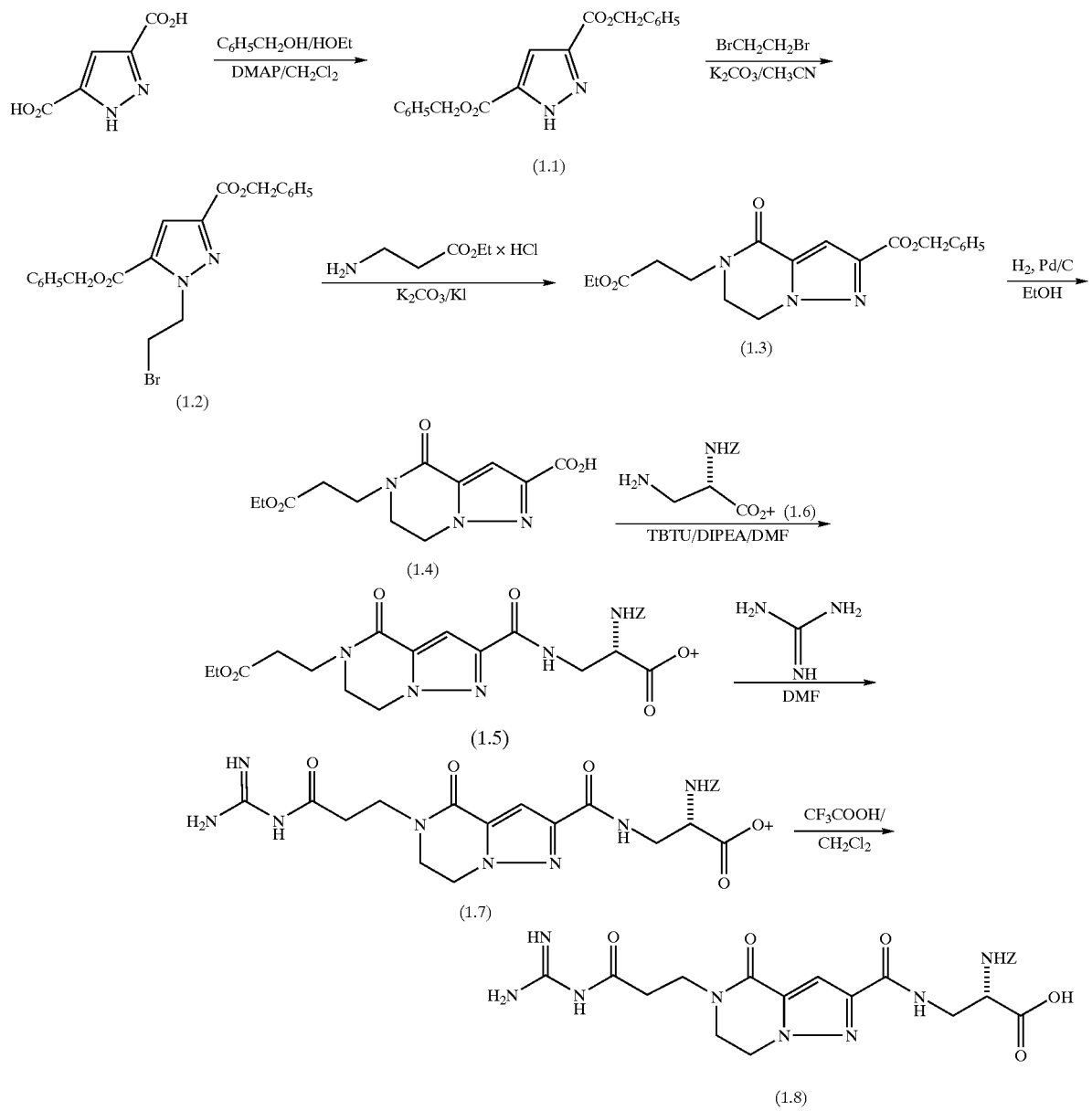

Dibenzyl pyrazole-3,5-dicarboxylate (1.1)

0.77 g (6.3 mmol) of 4-dimethylaminopyridine, 8.53 g (63.1 mmol) of 1-hydroxybenzotriazole hydrate, 12.1 g (63.1 mmol) of 1-(3-dimethylaminopropyl)-3-ethylcarbodiimide hydrochloride and 6.5 ml (6.8 g, 62.8 mmol) of benzyl alcohol were added to a mixture of 5.0 g (28.7 mmol) of pyrazole-3,5-dicarboxylic acid monohydrate in 150 ml of methylene chloride. The mixture was stirred at room temperature for about 20 hours under a nitrogen atmosphere until the reaction was complete (thin layer chromatography (TLC): silica gel; ethyl ether/pentane 50/50). The reaction mixture was diluted with 100 ml of water and then filtered, and the organic phase was separated and washed with 2×100 ml of water, 2×50 ml of 5% acetic acid and 100 ml of water. After drying over sodium sulfate, the solvent was removed in vacuo. The residue was chromatographed through silica gel (methanol/methylene chloride 5/95). Yield: 4.3 g (45%).

Melting point: 120° C. (Kofler stage)

TLC: $R_f$=0.3 (silica gel; diethyl ether/pentane 50/50)

IR (CHCl$_3$): 3420 (=C—NH); 1728 (CO); 1558–1495 cm-1 (C=C).

$^1$H NMR (CDCl$_3$) 250 MHz: 5.38 (s, 2CH$_2$); 7.38 (s, CH); 7.37 (m, Ph); 11.5 ppm (bs, NH).

| CHN analysis: | Calc. | C 67.85; | H 4.79; | N 8.33 |
|---|---|---|---|---|
| | Found | C 67.5; | H 4.6; | N 8.2 |

Dibenzyl 1-(2-bromoethyl)pyrazole-3,5-dicarboxylate (1.2)

400 mg (1.19 mmol) of dibenzyl pyrazole-3,5-dicarboxylate (1.1), 225 mg (1.63 mmol) of potassium carbonate and 1.04 ml (2.27 g, 12.0 mmol) of 1,2- dibromoethane in 10 ml of acetonitrile were heated under reflux in a nitrogen atmosphere until the reaction was complete (approx. 2 h; TLC: silica gel; methanol/methylene chloride 5/95). The reaction mixture was filtered and concentrated in vacuo. The residue was chromatographed through silica gel (methylene chloride and then methanol/methylene chloride 2/98). Yield: 450 mg (85%).

Melting point: 112° C. (Kofler stage)

TLC: $R_f$=0.3 (silica gel; methylene chloride)

IR (CHCl$_3$): 1727 (CO); 1588–1529–1498 cm$^{-1}$ (C=C).

$^1$H NMR (CDCl$_3$) 250 MHz: 3.72 (t, CH$_2$); 5.03 (t, CH$_2$); 5.34 (s, CH$_2$Ph); 5.38 (s, CH$_2$Ph); 7.30–7.47 ppm (m, 11CH).

| CHN analysis: | Calc. | C 56.90; | H 4.32; |
| --- | --- | --- | --- |
|  |  | N 6.32; | Br 18.02 |
|  | Found | C 56.9; | H 4.2; |
|  |  | N 6.2; | Br 18.0 |

Benzyl 5-(2-ethoxycarbonylethyl)-4,5,6,7-tetrahydro-4-oxopyrazolo[1,5-a]pyrazine-2-carboxylate (1.3)

A mixture of 4.00 g (9.02 mmol) of dibenzyl 1-(2-bromoethyl)pyrazole-3,5-dicarboxylate (1.2), 3.11 g (22.5 mmol) of potassium carbonate, 300 mg of potassium iodide and 1.52 g (9.90 mmol) of ethyl 3-aminopropionate hydrochloride in 250 ml of dioxane was heated under reflux and under a nitrogen atmosphere until the reaction was complete (approx. 48 h; TLC; silica gel; methanol/methylene chloride 5/95). The reaction mixture was filtered and concentrated in vacuo. The residue was chromatographed through silica gel (methylene chloride to methanol/methylene chloride 1/99). Yield: 1.60 g (48%), oil.

TLC: $R_f$=0.4 (silica gel; methanol/methylene chloride 5/95)

IR (CHCl$_3$): 1729–1666 (CO); 1552–1497 cm$^{-1}$ (C=N, C=C).

$^1$H NMR (CDCl$_3$) 250 MHz: 1.26 (t, CH$_3$); 2.73 (t, CH$_2$); 3.79 (t, CH$_2$); 3.94 (m, CH$_2$); 4.14 (q, CH$_2$); 4.44 (m, CH$_2$); 5.38 (s, CH$_2$Ph); 7.35 (s, CH); 7.28–7.47 ppm (m, 5CH).

| Mass spectrum: | Calc. | 371.40 |
| --- | --- | --- |
|  | Found | 372 (MH+). |

5-(2-Ethoxycarbonylethyl)-4,5,6,7-tetrahydro-4-oxopyrazolo[1,5-a]pyrazine-2-carboxylic acid (1.4)

A mixture of 600 mg (1.61 mmol) of benzyl 5-(2-ethoxycarbonylethyl)-4,5,6,7-tetrahydro-4-oxopyrazolo[1,5-a]pyrazine-2-carboxylate (1.3) and 200 mg of palladium (5% on active carbon) in 50 ml of ethanol was stirred under hydrogen until the reaction was complete (approx. 4 h; TLC; silica gel; methanol/methylene chloride 5/95). The catalyst was filtered off and the filtrate was concentrated in vacuo. Yield: 420 mg (92%), amorphous powder.

TLC: $R_f$=0.1 (silica gel; methanol/methylene chloride 10/90)

IR (CHCl$_3$): 3510 (OH); 1724–1709–1667 (CO); 1553–1503–1495 cm$^{-1}$ (C=N, C=C).

$^1$H NMR (CDCl$_3$) 250 MHz: 1.26 (t, CH$_3$); 2.75 (t, CH$_2$); 3.81 (t, CH$_2$); 3.98 (m, CH$_2$); 4.15 (q, CH$_2$); 4.48 (m, CH$_2$); 6.39 (bs, COOH); 7.41 ppm (s, CH).

| Mass spectrum: | Calc. | 281.27 |
| --- | --- | --- |
|  | Found | 282 (MH+); 288 (MLi+). | tert-Butyl (2S)-3-[5-(2-ethoxycarbonylethyl)-4,5,6,7-tetrahydro-4-oxopyrazolo[1,5-a]pyrazine-2-carbonylamino]-2-[benzyloxycarbonylamino]propionate (1.5)

A mixture of 420 mg (1.49 mmol) of 5-(2-ethoxycarbonyl-1-ethyl)-4,5,6,7-tetrahydro-4-oxopyrazolo[1,5-a]pyrazine-2-carboxylic acid (1.4), 0.82 ml (608 mg; 4.71 mmol) of diisopropylethylamine, 685 mg (2.13 mmol) of O-benzotriazol-1-yl-N,N,N',N'-tetramethyluronium tetrafluoroborate and 414 mg (1.41 mmol) of tert-butyl (2S)-3-amino-2-[benzyloxycarbonylamino]propionate (1.6) in 50 ml of dimethylformamide was stirred overnight under a nitrogen atmosphere. The reaction mixture was diluted with 50 ml of ethyl acetate and the organic phase was washed 2 times with 10 ml of 1N hydrochloric acid, 2 times with 30 ml of a saturated solution of sodium bicarbonate and 2 times with 30 ml of a saturated solution of sodium chloride. After drying over sodium sulfate and filtration, the solvent was removed in vacuo and the residue was chromatographed through silica gel (methylene chloride to methanol/methylene chloride 2/98). Yield: 450 mg (53%), oil.

TLC: $R_f$=0.6 (silica gel; methanol/methylene chloride 10/90)

$[\alpha]_D^{20}$=+10° (CH$_2$Cl$_2$, c=1.49)

IR (CHCl$_3$): 3420 (NH); 1722–1677 (CO); 1546–1506 cm$^{-1}$ (C=N, C=C, N—CO).

$^1$H NMR (CDCl$_3$) 250 MHz: 1.26 (t, CH$_3$); 1.45 (s, tBu), 2.73 (t, CH$_2$); 3.79 (t, CH$_2$); 3.80–4.00 (m, 2CH$_2$); 4.14 (q, CH$_2$); 4.35 (m, CH$_2$); 4.42 (m, CH); 5.11 (s, CH$_2$Ph); 5.78 (d, NH); 7.13 (t, NH); 7.26–7.40 ppm (m, 6CH).

| Mass spectrum: | Calc. | 557.61 |
| --- | --- | --- |
|  | Found | 558 (MH+); 564 (MLi+). |

Tert-Butyl (2S)-3-amino-2-benzyloxycarbonylaminopropionate (1.6)

10 g (42 mmol) of (2S)-3-amino-2-benzyloxycarbonylaminopropionic acid were shaken for 3 days, in an autoclave and under 20 atm. N$_2$ pressure, in a mixture of 100 ml of dioxane, 100 ml of isobutylene and 8 ml of conc. H$_2$SO$_4$. Excess isobutylene was blown off, and 150 ml of diethyl ether and 150 ml of a saturated solution of NaHCO$_3$ were added to the remaining solution. The phases were separated and the aqueous phase was extracted 2 times with 100 ml of diethyl ether on each occasion. The combined organic phases were washed with 2×100 ml of H$_2$O and dried over Na$_2$SO$_4$. After the solvent had been removed in vacuo, 9.58 g (78%) of (1.6) were obtained as a pale yellow oil.

tert-Butyl (2S)-3-[5-(2-guanidinocarbonylethyl)-4,5,6,7-tetrahydro-4-oxopyrazolo[1,5-a]pyrazine-2-carbonylamino]-2-[benzyloxycarbonylamino]propionate (1.7)

300 mg (0.54 mmol) of tert-butyl (2S)-3-[5-(2-ethoxycarbonylethyl)-4,5,6,7-tetrahydro-4-oxopyrazolo[1, 5-a]pyrazine-2-carbonylamino]-2-[benzyloxycarbonylamino]propionate (1.5) and 64 mg (1.08 mmol) of guanidine in 15 ml of dimethylformamide were stirred overnight under a nitrogen atmosphere. The reaction mixture was concentrated in vacuo and the residue was chromatographed several times through silica gel (methylene chloride to methanol/methylene chloride 15/95, then methanol/methylene chloride/acetic acid/water 15/85/2/2). Yield: 40 mg (13%), oil.

TLC: $R_f$=0.4 (silica gel; methanol/methylene chloride/acetic acid/water 15/85/2/2)

$^1$H NMR (DMSO-$d_6$) 300 MHz: 1.34 (s, tBu); 2.43 (t, $CH_2$); 3.40–3.75 (m, $2CH_2$); 3.84 (m, $CH_2$); 4.14 (m, CH); 4.39 (m, $CH_2$); 5.04 (s, $CH_2$Ph); 6.94 (s, NH); 6.98 (s, CH); 7.35 (m, 5CH); 7.73 (d, NH); 8.35 ppm (m, NH).

| Mass spectrum: | Calc. | 570.61 |
|---|---|---|
|  | Found | 571 (MH+). |

(2S)-3-[5-(2-Guanidinocarbonylethyl)-4,5,6,7-tetrahydro-4-oxopyrazolo[1,5-a]pyrazine-2-carbonylamino]-2-[benzyloxycarbonylamino]propionic acid (1.8)

40 mg (0.07 mmol) of tert-butyl (2S)-3-[5-(2-guanidinocarbonylethyl)-4,5,6,7-tetrahydro-4-oxopyrazolo[1,5-a]pyrazine-2-carbonylamino]-2-[benzyloxycarbonylamino]propionate (1.6) and 1.0 ml of trifluoroacetic acid in 5.0 ml of methylene chloride were stirred under a nitrogen atmosphere until the reaction was complete (approx. 3 h; TLC: silica gel; methanol/methylene chloride/acetic acid/water 15/85/2/2). The reaction mixture was diluted with 5 ml of toluene and concentrated in vacuo. The residue was taken up in ethyl acetate, and the precipitate was filtered off and washed several times with ethyl acetate and then dried in vacuo. Yield: 25 mg (70%), amorphous powder.

TLC: $R_f$=0.20 (silica gel; methanol/methylene chloride/acetic acid/water 15/85/2/2)

$^1$H NMR (DMSO-$d_6$) 300 MHz: 2.60 (m, $CH_2$); 3.56 (m, $CH_2$); 3.69 (m, $CH_2$); 3.84 (m, $CH_2$); 4.38 (m, $CH_2$); 4.05 (m, CH); 5.02 (s, $CH_2$Ph); 6.98 (m, CH); 7.34 (m, 5CH); 7.70 (m, NH); 8.24 (broad m, NH); 8.50 (m, H).

| Mass spectrum: | Calc. | 514.50 |
|---|---|---|
|  | Found | 515 (MH+). |

Example 2

(2S)-3-[5-(3-Guanidinocarbonylpropyl)-4,5,6,7-tetrahydro-4-oxopyrazolo[1,5-a]pyrazine-2-carbonylamino]-2-[benzyloxycarbonylamino]propionic acid (2.7)

The synthesis was carried out in accordance with the following reaction sequence:

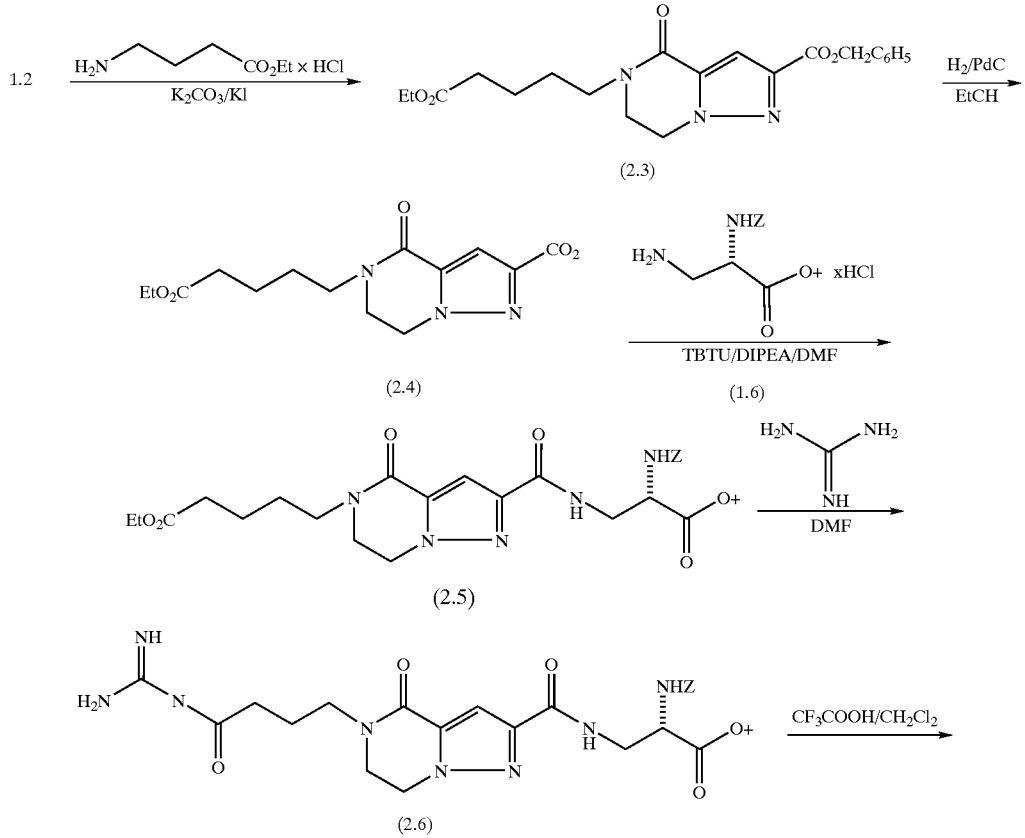

-continued

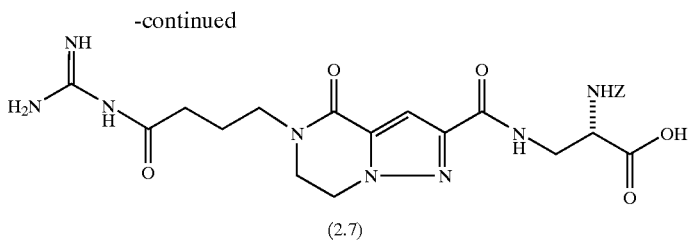

(2.7)

Dibenzyl 5-(3-ethoxycarbonylpropyl)-4,5,6,7-tetrahydro-4-oxopyrazolo[1,5-a]pyrazine-2-carboxylate (2.3)

500 mg (1.13 mmol) of dibenzyl 1-(2-bromoethyl) pyrazole-3,5-dicarboxylate (1.2; see Example 1), 315 mg (2.28 mmol) of potassium carbonate, 20 mg of potassium iodide and 206 mg (1.23 mmol) of ethyl 4-aminobutyrate hydrochloride in 50 ml of acetonitrile were heated under reflux in a nitrogen atmosphere until the reaction was complete (approx. 40 h; TLC: silica gel; methanol/methylene chloride 10/90). The reaction mixture was filtered and concentrated in vacuo. The residue was chromatographed through silica gel (methylene chloride, then methanol/methylene chloride 1/99). Yield: 240 mg (55%), oil.

TLC: $R_f$=0.6 (silica gel; methanol/methylene chloride 5/95)

IR (CHCl$_3$): 1729–1667 (CO); 1552–1496 cm-1 (C=N, C=C).

$^1$H NMR (CDCl$_3$) 250 MHz: 1.24 (t, CH$_3$); 1.96 (m, CH$_2$); 2.40 (t, CH$_2$); 3.61 (t, CH$_2$); 3.81 (m, CH$_2$); 4.10 (q, CH$_2$); 4.48 (m, CH$_2$); 5.40 (s, CH$_2$Ph); 7.36 (s, CH); 7.30–7.48 ppm (m, 5CH).

| Mass spectrum: | Calc. | 385.42 |
|---|---|---|
|  | Found | 386 (MH+), 392 (MLi+) |

5-(3-Ethoxycarbonylpropyl)-4,5,6,7-tetrahydro-4-oxopyrazolo[1,5-a]pyrazine-2-carboxylic acid (2.4)

700 mg (1.82 mmol) of benzyl 5-(3-ethoxycarbonylpropyl)-4,5,6,7-tetrahydro-4-oxopyrazolo[1,5-a]pyrazine-2-carboxylate (2.3) and 217 mg of palladium (5% on active carbon) in 50 ml of ethanol were stirred under hydrogen until the reaction was complete (approx. 4 h; TLC: silica gel; methanol/methylene chloride 10/90). The catalyst was filtered off and the filtrate was concentrated in vacuo. Yield: 240 mg (75%), amorphous powder. Melting point: 175° C. (Kofler stage)

TLC: $R_f$=0.1 (silica gel; methanol/methylene chloride 10/90)

IR (Nujol): 1715–1625 (CO); 1580–1554 cm$^{-1}$ (C=N, C=C).

$^1$H NMR (DMSO-d$_6$) 300 MHz: 1.16 (t, CH$_3$); 1.81 (m, CH$_2$); 2.34 (t, CH$_2$); 3.48 (t, CH$_2$); 3.81 (m, CH$_2$); 4.03 (q, CH$_2$); 4.45 (m, CH$_2$); 7.03 (s, CH); 13.0 ppm (s, COOH).

| Mass spectrum: | Calc. | 295.30 |
|---|---|---|
|  | Found | 296 (MH+), 318 (MNa+). | tert-Butyl (2S)-3-[5-(3-ethoxycarbonylpropyl)-4,5,6,7-tetrahydro-4-oxopyrazolo[1,5-a]pyrazine-2-carbonylamino]-2-[benzyloxycarbonylamino] propionate (2.5)

400 mg (1.35 mmol) of 5-(3-ethoxycarbonylpropyl)-4,5,6,7-tetrahydro-4-oxopyrazolo[1,5-a]pyrazine-2-carboxylic acid (2.4), 0.70 ml (519 mg; 4.01 mmol) of diisopropylethylamine, 589 mg (1.83 mmol) of O-benzotriazol-1-yl-N,N,N',N'-tetramethyluronium tetrafluoroborate and 356 mg (1.21 mmol) of tert-butyl (2S)-3-amino-2-[benzyloxycarbonylamino]propionate (1.6) (for synthesis, see Example 1) in 50 ml of dimethylformamide were stirred for 48 h under a nitrogen atmosphere. The reaction mixture was diluted with 50 ml of ethyl acetate and the organic phase was washed with 2 times 10 ml of 1N hydrochloric acid, 2 times 20 ml of a saturated solution of sodium bicarbonate and 2 times 30 ml of a saturated solution of sodium chloride. After drying over sodium sulfate, the organic phase was concentrated in vacuo and the residue was chromatographed through silica gel (methylene chloride to methanol/methylene chloride 2/98). Yield: 440 mg (57%), oil.

TLC: $R_f$=0.2 (silica gel; methanol/methylene chloride 5/95)

$[\alpha]_D^{20}$=+5° (CH$_2$Cl$_2$, c=0.58)

IR (CHCl$_3$): 3420 (NH); 1722–1676 (CO); 1547–1505 cm$^{-1}$ (C=N, C=C, N—CO).

$^1$H NMR (CDCl$_3$) 250 MHz: 1.23 (t, CH$_3$); 1.45 (s, tBu); 1.96 (m, CH$_2$); 2.39 (t, CH$_2$); 3.60 (t, CH$_2$); 3.78 (t, CH$_2$); 3.87 (m, CH$_2$); 4.10 (q, CH$_2$); 4.32 (t, CH$_2$); 4.40 (m, CH); 5.14 (s, CH$_2$Ph); 5.81 (d, NH); 7.17 (t, NH); 7.32 ppm (m, 6CH).

| Mass spectrum: | Calc. | 571.64 |
|---|---|---|
|  | Found | 572 (MH+), 610 (MK+). | tert-Butyl (2S)-3-[5-(3-guanidinocarbonylpropyl)-4,5,6,7-tetrahydro-4-oxopyrazolo[1,5-a]pyrazine-2-carbonylamino]-2-[benzyloxycarbonylamino] propionate (2.6)

200 mg (0.35 mmol) of tert-butyl (2S)-3-[5-(3-ethoxycarbonylpropyl)-4,5,6,7-tetrahydro-4-oxopyrazolo[1,5-a]pyrazine-2-carbonylamino-2-(benzoyloxycarbonylamino]propionate (2.5) and 42 mg (0.71 mmol) of guanidine in 10 ml of dimethylformamide were stirred at room temperature overnight under a nitrogen atmosphere. The reaction mixture was concentrated in vacuo and the residue was chromatographed through silica gel (methylene chloride to methanol/methylene chloride 15/85, then methanol/methylene chloride/acetic acid/water 15/85/2/2). Yield: 60 mg (29%), oil.

TLC: $R_f$=0.3 (silica gel; methanol/methylene chloride/acetic acid/water 15/85/2/2).

$^1$H NMR (DMSO-d$_6$) 300 MHz: 1.33 (s, tBu); 1.78 (m, CH$_2$); 2.19 (t, CH$_2$); 3.30–3.70 (m, 2CH$_2$); 3.83 (m, CH$_2$); 4.42 (m, CH$_2$); 4.13 (m, CH); 5.03 (s, CH$_2$Ph); 6.99 (m, CH); 7.36 (m, 5CH); 7.75 (d, NH); 8.35 ppm (m, NH).

| Mass spectrum: | Calc. | 584.64 |
| --- | --- | --- |
| | Found | 585 (MH+), 607 (MNa+). |

(2S)-3-[5-(3-Guanidinocarbonylpropyl)-4,5,6,7-tetrahydro-4-oxopyrazolo[1,5-a]pyrazine-2-carbonylamino]-2-[benzyloxycarbonylamino] propionic acid (2.7)

35 mg (0.06 mmol) of tert-butyl (2S)-3-[5-(3-guanidinocarbonylpropyl)-4,5,6,7-tetrahydro-4-oxopyrazolo[1,5-a]pyrazine-2-carbonylamino]-2-[benzoyloxycarbonylamino]propionate (2.6) and 0.5 ml of trifluoroacetic acid in 1.5 ml of methylene chloride were stirred under a nitrogen atmosphere until the reaction was complete (approx. 1 h, TLC: silica gel; methanol/methylene chloride/acetic acid/water 15/85/2/2). The reaction mixture was diluted with 5 ml of toluene and concentrated in vacuo. The residue was diluted with a mixture of ethyl ether/methylene chloride, and the precipitate was filtered and washed several times with ethyl ether/methylene chloride and then dried in vacuo. Yield: 30 mg (95%), amorphous powder.

TLC: $R_f$=0.15 (silica gel; methanol/methylene chloride/acetic acid/water 15/85/2/2).

$^1$H NMR (DMSO-d$_6$) 300 MHz: 1.84 (m, CH$_2$); 2.45 (m, CH$_2$); 3.51 (m, 2CH$_2$); 3.81 (m, CH$_2$); 4.09 (m, CH); 4.44 (m, CH$_2$); 5.02 (s, CH$_2$Ph); 7.01 (m, CH); 7.34 (m, 5H); 8.24 ppm (broad m, H).

| Mass spectrum: | Calc. | 528.53 |
| --- | --- | --- |
| | Found | 529 (MH+), 551 (MNa+). |

Example 3

3-[2-(Guanidinocarbonylmethyl)-2,3-dihydro-3-oxo-[1,2,4]triazolo[4,3-a]pyridin-6-carbonylamino]-2-[(phenylmethoxy)carbonylamino]propanoic acid (3.5)

The synthesis was carried out according to the following procedures.

2-(Ethoxycarbonylmethyl)-2,3-dihydro-3-oxo-[1,2,4]triazolo[4,3-a]pyridin-6-carboxylic acid t-butyl ester (3.1)

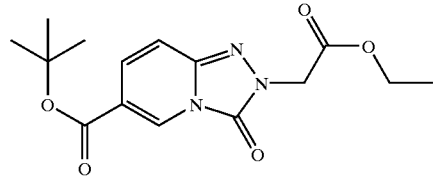

A mixture of 2,3-dihydro-3-oxo-[1,2,4]triazolo[4,3-a]pyridin-6-carboxylic acid t-butyl ester [prepared as in WO 94-18981] (350 mg, 1.49 mmoles), cesium carbonate (485 mg, 1.49 mmoles) and ethyl 2-bromoacetate (0.26 ml, 2.26 mmoles) in acetonitrile (50 ml) was refluxed during 1 hour. After cooling to room temperature, the precipitate was discarded by filtration and the filtrate was evaporated to dryness under reduced pressure. The residue was chromatographed (silica gel; elution with chloroform/ethyl acetate 80/20 v/v) and the solid recrystallized from diisopropyl ether giving light yellow crystals (330 mg, 68%).

Melting point: 108° C.

TLC: $R_f$=0.60 (silica gel; chloroform/ethyl acetate 80/20 v/v).

IR (CHCl$_3$): 1751, 1734, 1718 (C=O), 1643, 1559, 1539 cm$^{-1}$ (C=N+C=C).

$^1$H NMR (CDCl$_3$) 250 MHz: 1.30 (t, 3H, CH$_3$), 1.59 (s, 9H, t-Bu), 4.26 (q, 2H, CH$_2$), 4.77 (s, 2H, CH$_2$), 7.08 (dd, 1H, arom.), 7.59 (dd, 1H, arom.), 8.47 ppm (t, 1H, arom.).

| CHN analysis: | Calc. | C 56.07; | H 5.96; | N 13.08. |
| --- | --- | --- | --- | --- |
| | Found | C 56.3; | H 6.1; | N 12.8. |

2-(Ethoxycarbonylmethyl)-2,3-dihydro-3-oxo-[1,2,4]triazolo[4,3-a]pyridin-6-carboxylic acid (3.2)

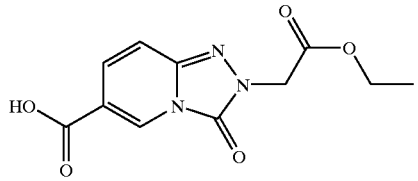

To a solution cooled at 0° C. of 2-(ethoxycarbonylmethyl)-2,3-dihydro-3-oxo-[1,2,4]triazolo[4,3-a]pyridin-6-carboxylic acid t-butyl ester (300 mg, 0.93 mmoles) in dichloromethane (5 ml) was added trifluoroacetic acid (5 ml). The mixture was stirred 4 hours at 0° C. After evaporation to dryness under reduced pressure, the solid residue was recrystallized from diisopropyl ether/isopropanol giving crystals (155 mg, 63%).

Melting point: 188° C.

TLC: $R_f$=0.20 (silica gel; dichloromethane/methanol 80/20 v/v).

IR (CHCl$_3$): 1743, 1734, 1700 (C=O), 1641, 1558, 1536 cm$^{-1}$ (C=N+C=C).

$^1$H NMR (DMSO-d$_6$) 250 MHz: 1.21 (t, 3H, CH$_3$), 4.17 (q, 2H, CH$_2$), 4.84 (s, 2H, CH$_2$), 7.30 (dd, 1H, arom.), 7.55

(dd, 1H, arom.), 8.29 (dd, 1H, arom.), 13.44 ppm (broad s, 1H, COOH).

| CHN analysis: | Calc. | C 49.81; | H 4.18; | N 15.84. |
|---|---|---|---|---|
| | Found | C 49.7; | H 4.0; | N 15.7. |

3-[2-(Ethoxycarbonylmethyl)-2,3-dihydro-3-oxo-[1,2,4]triazolo[4,3-a]pyridin-6-carbonylamino]-2-[(phenylmethoxy)carbonylamino]propanoic acid, t-butyl ester (3.3)

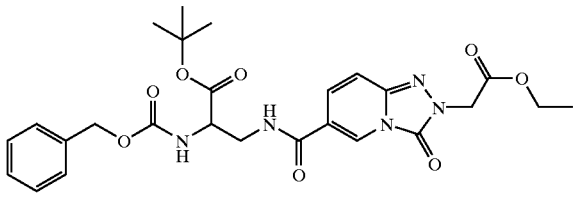

To a solution of 2-(ethoxycarbonylmethyl)-2,3-dihydro-3-oxo-[1,2,4]triazolo[4,3-a]pyridin-6-carboxylic acid (220 mg, 0.83 mmoles) in dry dimethylformamide (5 ml) were added successively N,N-diisopropylethylamin (0.435 ml, 2.5 mmoles), o-benzotriazol-1-yl-N,N,N',N'-tetramethyluronium tetrafluoroborate (362 mg, 1.13 mmoles) and 3-amino-2-(benzyloxycarbonylamino) propanoic acid t-butyl ester (244 mg, 0.83 mmoles) and the mixture was stirred at room temperature under inert atmosphere during the night. After the addition of ethyl acetate (150ml), the organic layer was washed with 1N hydrochloric acid (2×50 ml), with saturated sodium hydrogencarbonate solution (2×50ml), brine (1×50 ml), dried over magnesium sulfate and evaporated to dryness under reduced pressure. The residue was chromatographed (silica gel; elution with ethyl acetate/triethylamine 98/2 v/v) giving a light yellow oil (170 mg, 38%).

TLC: $R_f$=0.70 (silica gel; ethyl acetate/triethylamine 98/2 v/v).

IR (CHCl$_3$): 3414 (NH), 1729, 1672 (C=O), 1642, 1630, 1560, 1532, 1506 cm$^{-1}$ (C=C+C=N+amide).

$^1$H NMR (CDCl$_3$) 250 MHz: 1.30 (t, 3H, CH$_3$), 1.48 (s, 9H, t-Bu), 3.79 (m, 2H, CH$_2$), 4.27 (q, 2H, CH$_2$), 4.45 (m, 1H, CH), 4.77 (s, 2H, CH$_2$), 5.14 (s, 2H, CH$_2$Ph), 5.89 (d, 1H, NH), 7.08 (dd, 1H, arom.), 7.33 (m, 6H, arom.+NH), 7.41 (d, 1H, arom.), 8.31 ppm (s, 1H, arom.).

| CHN analysis: | Calc. | C 57.66; | H 5.77; | N 12.93. |
|---|---|---|---|---|
| | Found | C 57.6; | H 5.9; | N 12.6. |

3-[2-(Guanidinocarbonylmethyl)-2,3-dihydro-3-oxo-[1,2,4]triazolo[4,3-a]pyridin-6-carbonylamino]-2-[(phenylmethoxy)carbonylamino]propanoic acid, t-butyl ester (3.4)

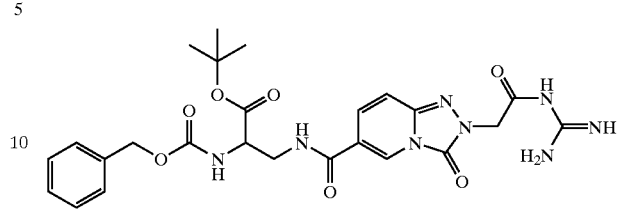

A mixture of 3-[2-(ethoxycarbonylmethyl)-2,3-dihydro-3-oxo-[1,2,4]triazolo[4,3-a]pyridin-6-carbonylamino]-2-[(phenylmethoxy) carbonylamino]propanoic acid t-butyl ester (170 mg, 0.31 mmoles) and guanidine base (30 mg, 0.51 mmoles) in dry tetrahydrofuran (10 ml) and t-butanol (0.5 ml) was stirred at room temperature under inert atmosphere during the night. The mixture was evaporated to dryness under reduced pressure and the residue was chromatographed (silica gel; elution with dichloromethane/methanol 85/15 v/v) giving a colourless oil (100 mg, 58%).

TLC: $R_f$=0.40 (silica gel; dichloromethane/methanol 85/15 v/v).

IR (CHCl$_3$): 3505, 3405, 3310 (NH/NH$_2$), 1731, 1714 (C=O), 1667, 1627, 1607, 1532 cm$^{-1}$ (C=O+C=N+C=C+NH/NH$_2$).

$^1$H NMR (DMSO-d$_6$) 300 MHz: 1.35 (s, 9H, tBu), 3.58 (m, 2H, CH$_2$), 4.22 (m, 1H, CH), 4.46 (s, 2H, CH$_2$), 5.05 (m, 2H, CH$_2$Ph), 6.66 (broad s, NH), 7.27 (d, 1H, arom.), 7.34 (m, 5H, arom.), 7.52 (dd, 1H, arom.), 7.69 (d, 1H, NH), 7.73 (broad s, NH), 8.47 (broad s, 1H, arom.), 8.67 ppm (t, 1H, NH).

| Mass spectrum: | 555 (MH+), 577 (MNa+). | | | |
|---|---|---|---|---|
| CHN analysis: | Calc. | C 54.15; | H 5.45; | N 20.21. |
| | Found | C 52.5; | H 5.2; | N 19.0. |

3-[2-(Guanidinocarbonylmethyl)-2,3-dihydro-3-oxo-[1,2,4]triazolo[4,3-a]pyridin-6-carbonylamino]-2-[(phenylmethoxy)carbonylamino]propanoic acid (3.5)

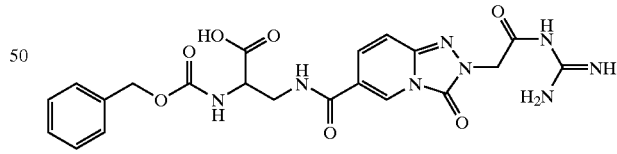

To a solution of 3-[2-(guanidinocarbonylmethyl)-2,3-dihydro-3-oxo-[1,2,4]triazolo[4,3-a]pyridin-6-carbonylamino]-2-[(phenylmethoxy)carbonylamino] propanoic acid t-butyl ester (95 mg, 0.17 mmoles) in dichloromethane (5 ml) cooled to 0° C. was added trifluoroacetic acid (2 ml). After reaching room temperature the solution was stirred further 3 hours. The mixture was evaporated to dryness under reduced pressure after having added toluene (20 ml). The residue was chromatographed (silicagel; elution with dichloromethane/methanol/ammonium hydroxide 70/30/4 v/v/v) giving a pale yellow powder (20 mg, 24%).

Melting point: >250° C. decomp.

TLC: $R_f$=0.30 (silica gel; dichloromethane/methanol/ammonium hydroxide 70/30/4 V/V/V).

IR (Nujol): 3374 (NH/OH), 1710 (C=O), 1654 (C=O+ C=N), 1632, 1525 cm$^{-1}$ (arom.+amide).

$^1$H NMR (DMSO-d$_6$) 300 MHz: 3.59 (m, 2H, CH$_2$), 4.23 (q, 1H, CH), 4.46 (s, 2H, CH$_2$), 5.03 (AB, 2H, CH$_2$Ph), 6.71 (broad s, 1H, NH), 7.09 (broad s, NH), 7.26 (d, 1H, arom.), 7.33 (broad s, 5H, arom.), 7.53 (broad d, 1H, arom.), 7.78 (broad s, NH), 8.47 (broad s, 1H, arom.), 8.72 ppm (t, NH).

| Mass spectrum: | 499 (MH+). | | |
|---|---|---|---|
| CHN analysis: | Calc. | C 50.60; | H 4.45; N 22.48. |
| | Found | C 48.1; | H 4.6; N 19.0. |

Example 4

2-(Benzyloxycarbonylamino)-3-[[2-(2-(guanidylcarbonyl)-1-ethyl)-5-benzimidazolyl]carbonylamino]propanoic acid (4.5)

The synthesis was carried out according to the following procedures.

3-[5-Carboxy-2-benzimidazolyl]propanoic acid, methyl ester (4.1)

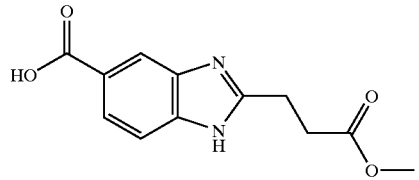

To a mixture of 3,4-diaminobenzoic acid (3.0 g, 20 mmoles) and triethylamine (5.5 ml, 40 mmoles) in tetrahydrofuran (400 ml) was added at room temperature and under inert atmosphere within 20 minutes a solution of 3-carbomethoxypropionyl chloride (2.4 ml, 20 mmoles) in tetrahydrofuran (100 ml). The brown mixture was stirred at room temperature during 24 hours, the solid formed was discarded by filtration and the filtrate evaporated to dryness under reduced pressure. To the residue was added acetic acid (300 ml) and the whole was refluxed during 5 hours. The mixture was evaporated to dryness under reduced pressure and the residue was chromatographed (silica gel; elution with dichloromethane/ethyl acetate 50/50 v/v, then dichloromethane/ethyl acetate/methanol 50/50/5 v/v/v and finally dichloromethane/ethyl acetate/methanol/acetic acid 50/50/5/2 v/v/v/v) giving an amorphous solid (2.6 g, 52%).

TLC: $R_f$=0.05 (silica gel; ethyl acetate).

IR (Nujol): 3250 (OH, NH), 1717, 1685 (C=O), 1624, 1593, 1542, 1480 cm$^{-1}$ (C=N+arom.).

$^1$H NMR (DMSO-d$_6$) 250 MHz: 2.91 (m, 2H, CH$_2$), 3.12 (m, 2H, CH$_2$), 3.61 (s, 3H, CH$_3$), 7.52 (d, 1H, arom.), 7.77 (dd, 1H, arom.), 8.06 (broad s, 1H, arom.), 12.60 ppm (broad m, 2H, NH+OH).

Mass spectrum: 248 (M+).

3-[5-[2-(Benzyloxycarbonylamino)-2-t-butoxycarbonyl-1-ethylaminocarbonyl]-2-benzimidazolyl]propanoic acid, methyl ester (4.2)

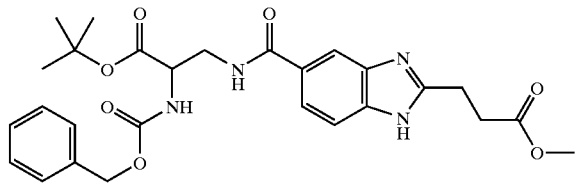

A mixture of 3-[5-carboxy-2-benzimidazolyl]propanoic acid methyl ester (1.7 g, 6.8 mmoles), 3-amino-2-(benzyloxycarbonylamino)propanoic acid t-butyl ester (2.6 g, 8.8 mmoles), 1-hydroxybenzotriazole (1.1 g, 8.1 mmoles), 1-(3-dimethylaminopropyl)-3-ethylcarbodimide hydrochloride (1.7 g, 8.8 mmoles) and N-methylmorpholine (1.5 ml, 13.6 mmoles) in dry dimethylformamide (50 ml) was stirred at room temperature under inert atmosphere during 48 hours. The mixture was evaporated to dryness under reduced pressure and the residue chromatographed (silica gel; ethyl acetate) giving an amorphous solid (2.0 g, 55%).

TLC: $R_f$=0.40 (silica gel; ethyl acetate).

IR (CHCl$_3$): 3445, 3413 (NH), 1722, 1661 (C=O), 1626, 1600, 1580, 1536 (arom.), 1440 (COOMe), 1370 cm$^{-1}$ (COOtBu).

$^1$H NMR (CDCl$_3$) 300 MHz: 1.45 (s, 9H, t-Bu), 2.90 (m, 2H, CH$_2$), 3.23 (m, 2H, CH$_2$), 3.72 (s, 3H, CH$_3$), 3.87 (t, 2H, CH$_2$), 4.43 (q, 1H, CH), 5.10 (broad s, 2H, CH$_2$Ph), 6.05 (d, 1H, NH), 7.05 (t, 1H, NH), 7.29 (m, 5H, arom.), 7.54 (m, 1H, arom.), 7.59 (m, 1H, arom.), 7.98 ppm (broad s, 1H, arom.).

Mass spectrum: 525 (MH+), 547 (MNa+).

3-[5-[2-(Benzyloxycarbonylamino)-2-t-butoxycarbonyl-1-ethylaminocarbonyl]-1-t-butoxycarbonyl-2-benzimidazolyl]propanoic acid, methyl ester and 3-[5-[2-(Benzyloxycarbonylamino)-2-t-butoxycarbonyl-1-ethylaminocarbonyl]-3-t-butoxycarbonyl-2-benzimidazolyl]propanoic acid, methyl ester (4.3)

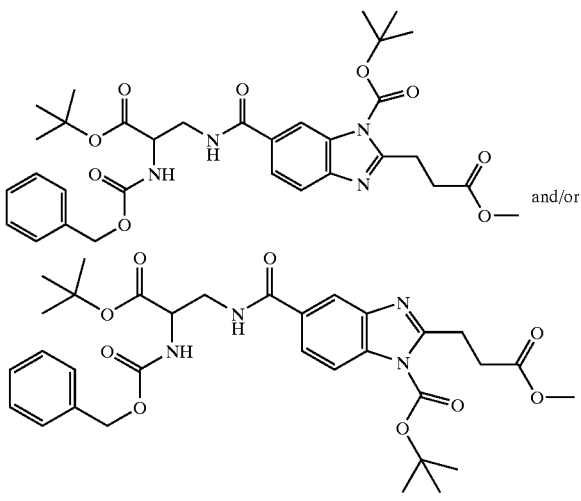

To a mixture of 3-[5-[2-(benzyloxycarbonylamino)-2-t-butoxycarbonyl-1-ethylaminocarbonyl]-2-benzimidazolyl]

propanoic acid methyl ester (965 mg, 1.84 mmoles), (Boc)₂O (405 mg, 1.85 mmoles) and 4-dimethylaminopyridine (224 mg, 1.83 mmoles) in dichloromethane (80 ml) under inert atmosphere was added triethylamine (260 μl, 1.86 mmoles) at room temperature. After stirring during half an hour, diethyl ether (100 ml) and water (50 ml) were added. The organic layer was separated, dried over magnesium sulfate and evaporated to dryness under reduced pressure. The residue was chromatographed (silica gel; elution with gradient dichloromethane/diethyl ether from 100/0 to 0/100) giving a white amorphous solid (790 mg, 68%).

TLC: R$_f$=0.90 (silica gel; ethyl acetate).

IR (CHCl₃): 3416 (NH), 1736, 1661 (C=O), 1620, 1588, 1507 cm$^{-1}$ (arom.+amide)

¹H NMR (DMSO-d₆) 300 MHz: 1.30 and 1.36 (2s, 2×9H, tBu), 2.91 (t, 2H, CH₂), 3.40 (td, 2H, CH₂), 3.62 (sd, 3H, CH₃), 3.69 and 3.96 (2m, 2H, CH₂), 5.03–5.20 (m, 3H, CH+CH₂Ph), 7.30–7.34 (m, 5H, arom.), 7.68 and 7.93 (2d, 1H, arom.), 7.75 and 7.82 (2d, 1H, arom.), 8.10 and 8.40 (2s, 1H, arom.), 8.75 ppm (d, 1H, NH).

Mass spectrum: 625 (MH+), 647 (MNa+).

2-(Benzyloxycarbonylamino)-3-[[2-(2-(guanidylcarbonyl)-1-ethyl)-5-benzimidazolyl]carbonylamino]propanoic acid, t-butyl ester (4.4)

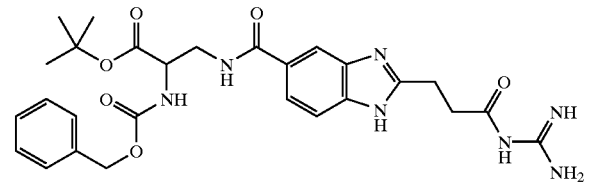

A mixture of 3-[5-[2-(Benzyloxycarbonylamino)-2-t-butoxycarbonyl-1-ethylaminocarbonyl]-1 (and 3)-t-butoxycarbonyl-2-benzimidazolyl]propanoic acid methyl ester (790 mg, 1.26 mmoles) and guanidine base (780 mg, 13 mmoles) in dry dimethylformamide (30 ml) was stirred at room temperature under inert atmosphere during 1 hour. The mixture was evaporated to dryness under reduced pressure and the residue was chromatographed (silica gel; elution with a gradient dichloromethane/methanol/water/acetic acid 90/10/1/1 to 85/15/2/2 and finally 70/30/6/3 v/v/v/v) giving a white powder (860 mg). To the solid was added methanol (6 ml), the solution was filtered and the filtrate poured into a mixture of ethyl acetate/diethyl ether/pentane (600 ml, 1/1/1 v/v/v). The precipitate was filtered, washed with pentane and dried under vacuum giving an amorphous solid (470 mg, 68%).

TLC: R$_f$=0.28 (silica gel; dichloromethane/methanol/water/acetic acid 85/15/2/2 v/v/v/v).

IR (Nujol): 1730, 1701 (C=O), 1623, 1540 cm$^{-1}$ (C=O+C=N+arom.+amide).

¹H NMR (DMSO-d₆) 300 MHz: 1.33 and 1.40 (2s, 9H, t-Bu), 2.92 (t, 2H, CH₂), 3.09 (t, 2H, CH₂), 3.58 and 3.70 (m, 2H, CH₂), 4.24 (q, 1H, CH), 5.05 (s, 2H, CH₂Ph), 7.11 (broad s, NH), 7.32 (broad m, NH), 7.35 (s, 5H, arom.), 7.48 (d, 1H, arom.), 7.62 (broad d, 1H, arom.), 7.71 (broad d, NH), 7.90 (broad s, 1H, arom.), 8.42 ppm (broad m, NH).

Mass spectrum: 552 (MH+).

2-(Benzyloxycarbonylamino)-3-[[2-(2-(guanidylcarbonyl)-1-ethyl)-5-benzimidazolyl]carbonylamino]propanoic acid (4.5)

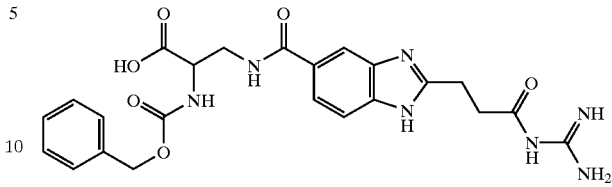

To a suspension of 2-(Benzyloxycarbonylamino)-3-[[2-(2-(guanidylcarbonyl)-1-ethyl)-5-benzimidazolyl]carbonylamino]propanoic acid t-butyl ester (230 mg, 0.42 mmoles) in dichloromethane (10 ml) was added dropwise trifluoroacetic acid (2 ml). The mixture was stirred at room temperature during 2 hours and then toluene (50 ml) was added. The mixture was evaporated to dryness under reduced pressure and the residue dissolved in methanol (1.5 ml). This solution was poured in a solution of diethyl ether-ethyl acetate (200 ml, 1/1) and the precipitate was collected and reprecipitated by the same procedure giving after filtration and drying under vacuum an amorphous powder (85 mg, 41%).

TLC: R$_f$=0.05 (silica gel; dichloromethane/methanol/water/acetic acid 85/15/2/2 v/v/v/v).

¹H NMR (DMSO-d₆) 300 MHz: 3.04 (m, 2H, CH₂), 3.14 (m, 2H, CH₂), 3.62 (m, 2H, CH₂), 4.24 (m, 1H, CH), 5.02 (broad s, 2H, CH₂Ph), 7.32 (m, 5H, arom.), 7.51 (m, 2H, arom.+NH), 7.65 (d, 1H, arom.), 7.99 (broad s, 1H, arom.), 8.20–8.70 (broad m, 4H, NH), 12.53 ppm (m, 2H, NH+COOH).

Mass spectrum: 518 (MNa+), 496 (MH+).

Example 5

3-[2-(2-Guanidinocarbonyl-1-ethyl)-2,3-dihydro-3-oxo-[1,2,4]triazolo[4,3-a]pyridin-6-carbonylamino]-2-[(phenylmethoxy)carbonylamino]propanoic acid (5.5)

The synthesis was carried out according to the following procedures.

2-(2-Ethoxycarbonyl-1-ethyl)-2,3-dihydro-3-oxo-[1,2,4]triazolo[4,3-a]pyridin-6-carboxylic acid t-butyl ester (5.1)

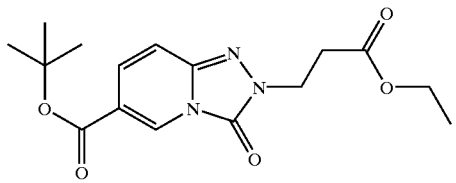

A mixture of 2,3-dihydro-3-oxo-[1,2,4]triazolo[4,3-a]pyridin-6-carboxylic acid t-butyl ester [prepared as in WO 94-18981] (500 mg, 2.1 mmoles), cesium carbonate (1.38 g, 4.2 mmoles) and ethyl 3-bromopropionate (0.41 ml, 3.2 mmoles) in acetonitrile (50 ml) was refluxed during 8 hours and stirred at room temperature during the night. The precipitate was discarded by filtration and the filtrate was evaporated to dryness under reduced pressure. The residue was chromatographed (silica gel; elution with dichloromethane/ethyl acetate 80/20 v/v) giving a light yellow oil (500 mg, 71%).

TLC: $R_f$=0.71 (silica gel; chloroform/ethyl acetate 60/40 v/v).

IR (CHCl$_3$): 1717 (C=O), 1641, 1557, 1535 cm$^{-1}$ (C=N+C=C).

$^1$H NMR (CDCl$_3$) 250 MHz: 1.25 (t, 3H, CH$_3$), 1.58 (s, 9H, t-Bu), 2.87 (t, 2H, CH$_2$), 4.16 (q, 2H, CH$_2$), 4.31 (t, 2H, CH$_2$), 7.06 (dd, 1H, arom.), 7.56 (dd, 1H, arom.), 8.45 ppm (t, 1H, arom.).

| CHN analysis: | Calc. | C 57.30; | H 6.31; | N 12.53. |
|---|---|---|---|---|
| | Found | C 57.3; | H 6.2; | N 12.4. |

2-(2-Ethoxycarbonyl-1-ethyl)-2,3-dihydro-3-oxo-[1,2,4]triazolo[4,3-a]pyridin-6-carboxylic acid (5.2)

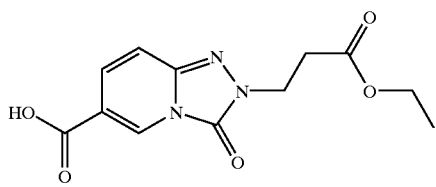

To a solution cooled at 0° C. of 2-(2-ethoxycarbonyl-1-ethyl)-2,3-dihydro-3-oxo-[1,2,4]triazolo[4,3-a]pyridin-6-carboxylic acid t-butyl ester (1.3 g, 3.9 mmoles) in dichloromethane (20 ml) was added trifluoroacetic acid (20 ml). The mixture was stirred 1 hour at 0° C. and then 24 hours at room temperature. After evaporation to dryness under reduced pressure, the solid residue was recrystallized from diisopropyl ether giving crystals (800 mg, 74%).

Melting point: 138° C.

TLC: $R_f$=0.30 (silica gel; chloroform-ethyl acetate 60/40 v/v).

IR (CHCl$_3$): 1731, 1701 (C=O), 1640, 1560, 1538 cm$^{-1}$ (C=N+C=C).

$^1$H NMR (CDCl$_3$) 300 MHz: 1.26 (t, 3H, CH$_3$), 2.90 (t, 2H, CH$_2$), 4.17 (q, 2H, CH$_2$), 4.34 (t, 2H, CH$_2$), 7.13 (dd, 1H, arom.), 7.61 (dd, 1H, arom.), 8.71 (m, 1H, arom.), 10.00 ppm (broad s, 1H, COOH).

| CHN analysis: | Calc. | C 51.61; | H 4.69; | N 15.05. |
|---|---|---|---|---|
| | Found | C 51.7; | H 4.7; | N 14.7. |

3-[2-(2-Ethoxycarbonyl-1-ethyl)-2,3-dihydro-3-oxo-[1,2,4]triazolo[4,3-a]pyridin-6-carbonylamino]-2-[(phenylmethoxy)carbonylamino]propanoic acid, t-butyl ester (5.3)

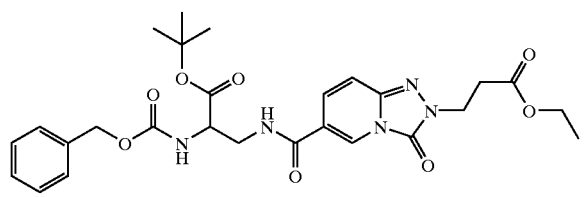

To a solution of 2-(2-ethoxycarbonyl-1-ethyl)-2,3-dihydro-3-oxo-[1,2,4]triazolo[4,3-a]pyridin-6-carboxylic acid (800 mg, 2.86 mmoles) in dry dimethylformamide (20 ml) were added successively N,N-diisopropylethylamin (1.5 ml, 8.6 mmoles), O-benzotriazol-1-yl-N,N,N',N'tetramethyluronium tetrafluoroborate (1.25 g, 3.9 mmoles) and 3-amino-2-(benzyloxycarbonylamino) propanoic acid t-butyl ester (760 mg, 2.58 mmoles) and the mixture was stirred at room temperature under inert atmosphere during 6 hours. After the addition of ethyl acetate (100 ml), the organic layer was washed with 1N hydrochloric acid (2×50 ml), with saturated sodium hydrogenocarbonate solution (2×50 ml), brine (1×50 ml), dried over magnesium sulfate and evaporated to dryness under reduced pressure. The residue was chromatographed (silica gel; elution with ethyl acetate/triethylamine 100/2 v/v) giving a light yellow oil (800 mg, 50%).

TLC: $R_f$=0.73 (silica gel; ethyl acetate/triethylamine 98/2 v/v).

IR (CHCl$_3$): 3409, 3344 (NH), 1729, 1670 (C=O), 1641, 1628, 1560, 1529, 1507 cm$^{-1}$ (C=C+C=N+amide).

$^1$H NMR (CDCl$_3$) 300 MHz: 1.24 (t, 3H, CH$_3$), 1.47 (s, 9H, t-Bu), 2.87 (t, 2H, CH$_2$), 3.82 (m, 2H, CH$_2$), 4.15 (q, 2H, CH$_2$), 4.30 (t, 2H, CH$_2$), 4.47 (m, 1H, CH), 5.12 (AB, 2H, CH$_2$Ph), 5.93 (broad d, 1H, NH), 7.06 (dd, 1H, arom.), 7.20–7.40 (m, 6H, 5arom.+NH), 7.44 (dd, 1H, arom.), 8.36 ppm (broad s, 1H, arom.).

| CHN analysis: | Calc. | C 58.37; | H 5.99; | N 12.61. |
|---|---|---|---|---|
| | Found | C 58.1; | H 6.0; | N 12.6. |

3-[2-(2-Guanidinocarbonyl-1-ethyl)-2,3-dihydro-3-oxo-[1,2,4]triazolo[4,3-a]pyridin-6-carbonylamino]-2-[(phenylmethoxy)carbonylamino]propanoic acid, t-butyl ester (5.4)

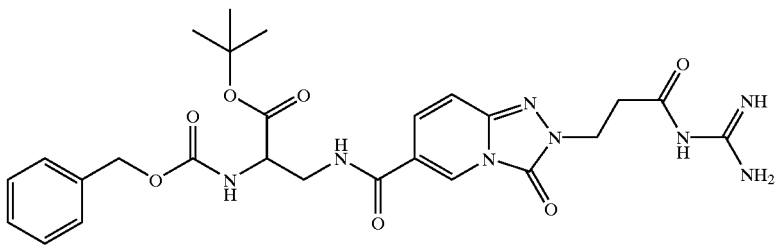

A mixture of 3-[2-(2-ethoxycarbonyl-1-ethyl)-2,3-dihydro-3-oxo-[1,2,4]triazolo[4,3-a]pyridin-6-carbonylamino]-2-[(phenylmethoxy)carbonylamino]propanoic acid t-butyl ester (300 mg, 0.54 mmoles) and guanidine base (160 mg, 2.71 mmoles) in dry dimethylformamide (10 ml) was stirred at room temperature under inert atmosphere during 30 hours. The mixture was evaporated to dryness under reduced pressure and the residue was chromatographed (silica gel; elution with dichloromethane/methanol/water/acetic acid 90/10/1/1 v/v/v/v) giving a colourless powder (90 mg, 29%).

Melting point: 120° C. decomp.

TLC: $R_f$=0.26 (silica gel; dichloromethane/methanol/water/acetic acid 90/10/1/1 v/v/v/v).

IR (CHCl$_3$): 3360 (NH/NH$_2$), 1730, 1714 (C=O), 1670, 1603, 1539, 1531 cm$^{-1}$ (C=O+C=N+C=C+NH/NH$_2$).

$^1$H NMR (DMSO-d$_6$) 300 MHz: 1.35 (s, 9H, tBu), 2.61 (t, 2H, CH$_2$), 3.57 (m, 2H, CH$_2$), 4.10 (t, 2H, CH$_2$), 4.22 (q, 1H, CH), 5.05 (AB, 2H, CH$_2$Ph), 6.66 (broad m, NH), 7.25–7.40 (m, 5H, arom.), 7.29 (m, 1H, arom.), 7.53 (dd, 1H, arom.), 7.68 (d, 1H, NH), 7.70 (broad m, NH), 8.44 (broad s, 1H, arom.), 8.65 ppm (t, 1H, NH).

| Mass spectrum: | 569 (MH+). | | |
|---|---|---|---|
| CHN analysis: | Calc. | C 54.92; | H 5.67; N 19.71. |
| | Found | C 52.5; | H 5.9; N 17.6. |

3-[2-(2-Guanidinocarbonyl-1-ethyl)-2,3-dihydro-3-oxo-[1,2,4]triazolo[4,3-a]pyridin-6-carbonylamino]-2-[(phenylmethoxy)carbonylamino]propanoic acid (5.5)

To a solution of 3-[2-(2-guanidinocarbonyl-1-ethyl)-2,3-dihydro-3-oxo-[1,2,4]triazolo[4,3-a]pyridin-6-carbonylamino]-2-[(phenylmethoxy)carbonylamino]propanoic acid t-butyl ester (85 mg, 0.15 mmoles) in dichloromethane (10 ml) cooled to 0° C. was added trifluoroacetic acid (3 ml). After reaching room temperature the solution was stirred further 5 hours. The mixture was evaporated to dryness under reduced pressure after having added toluene (20 ml). The residue was chromatographed twice (silicagel; elution with chloroform/methanol/water/acetic acid 70/30/6/3 v/v/v/v) giving a pale yellow powder (45 mg, 58%).

Melting point: 125° C. decomp.

TLC: $R_f$=0.39 (silica gel; chloroform/methanol/water/acetic acid 70/30/6/3 v/v/v/v).

IR (Nujol): 3340 (NH/OH), 1706 (C=O), 1653 (C=O+C=N), 1600, 1545, 1530, 1499 cm$^{-1}$ (arom.+amide).

$^1$H NMR (DMSO-d$_6$) 300 MHz: 2.63 (t, 2H, CH$_2$), 3.48 (m, 2H, CH$_2$), 3.92 (m, 1H, CH), 4.09 (t, 2H, CH$_2$), 4.99 (AB, 2H, CH$_2$Ph), 6.73 (d, 1H, NH), 7.00 (broad m, NH), 7.15–7.40 (m, 7H, arom.+NH), 7.48 (broad d, 1H, arom.), 8.00 (broad m, NH), 8.34 (s, 1H, arom.), 8.70 (sl, NH).

| Mass spectrum: | 513 (MH+), 535 (MNa+), 551 (MK+). | | |
|---|---|---|---|
| CHN analysis: | Calc. | C 51.56; | H 4.72; N 21.86. |
| | Found | C 48.7; | H 4.7; N 18.2. |

Example 6

3-[2-(3-Guanidinocarbonyl-1-propyl)-2,3-dihydro-3-oxo-[1,2,4]triazolo[4,3-a]pyridin-6-carbonylamino]-2-[(phenylmethoxy)carbonylamino]propanoic acid (6.5)

The synthesis was carried out according to the following procedures.

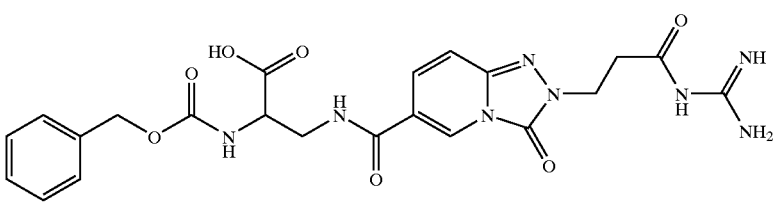

2-(3-Ethoxycarbonyl-1-propyl)-2,3-dihydro-3-oxo-[1,2,4]triazolo[4,3-a]pyridin-6-carboxylic acid t-butyl ester (6.1)

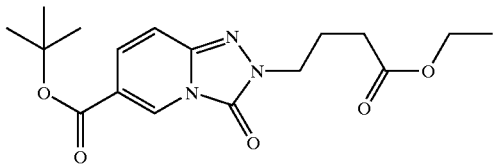

A mixture of 2,3-dihydro-3-oxo-[1,2,4]triazolo[4,3-a]pyridin-6-carboxylic acid t-butyl ester [prepared as in WO 94-18981] (1.00 g, 4.25 mmoles), cesium carbonate (2.70 g, 8.28 mmoles) and ethyl 3-bromobutyrate (1.24 g, 6.36 mmoles) in acetonitrile (100 ml) was refluxed during 1 hour and stirred at room temperature during the night. The precipitate was discarded by filtration and the filtrate was evaporated to dryness under reduced pressure. The residue was chromatographed (silica gel; elution with dichloromethane/ethyl acetate 80/20 v/v) giving a light yellow oil (1.30 g, 87%).

TLC: $R_f$=0.58 (silica gel; chloroform/ethyl acetate 60/40 v/v).

IR (CHCl$_3$): 1717 (C=O), 1641, 1557, 1536 cm$^{-1}$ (C=N+C=C).

$^1$H NMR (CDCl$_3$) 250 MHz: 1.25 (t, 3H, CH$_3$), 1.58 (s, 9H, t-Bu), 2.18 (m, 2H, CH$_2$), 2.40 (m, 2H, CH$_2$), 4.07 (t, 2H, CH$_2$), 4.13 (q, 2H, CH$_2$), 7.07 (dd, 1H, arom.), 7.57 (dd, 1H, arom.), 8.46 ppm (t, 1H, arom.).

| CHN analysis: | Calc. | C 58.44; | H 6.64; | N 12.03. |
|---|---|---|---|---|
| | Found | C 58.4; | H 6.7; | N 11.9. |

2-(3-Ethoxycarbonyl-1-propyl)-2,3-dihydro-3-oxo-[1,2,4]triazolo[4,3-a]pyridin-6-carboxylic acid (6.2)

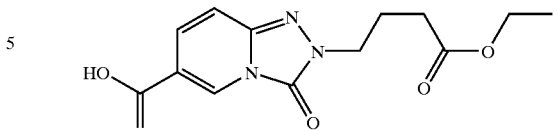

To a solution cooled at 0° C. of 2-(3-ethoxycarbonyl-1-propyl)-2,3-dihydro-3-oxo-[1,2,4]triazolo[4,3-a]pyridin-6-carboxylic acid t-butyl ester (1.3 g, 3.7 mmoles) in dichloromethane (20 ml) was added trifluoroacetic acid (20 ml). The mixture was stirred one hour at 0° C. and then 6 hours at room temperature. After evaporation to dryness under reduced pressure, the solid residue was recrystallized from diisopropyl ether giving crystals (750 mg, 68%).

Melting point: 140° C.

TLC: $R_f$=0.16 (silica gel; chloroform/ethyl acetate 60/40 v/v).

IR (CHCl$_3$): 1728, 1701 (C=O), 1640, 1560, 1535 cm$^{-1}$ (C=N+C=C).

$^1$H NMR (CDCl$_3$) 300 MHz: 1.25 (t, 3H, CH$_3$), 2.20 (m, 2H, CH$_2$), 2.42 (t, 2H, CH$_2$), 4.10 (m, 2H, CH$_2$), 4.14 (q, 2H, CH$_2$), 7.04 (dd, 1H, arom.), 7.62 (dd, 1H, arom.), 8.72 (t, 1H, arom.), 8.70 ppm (broad s, 1H, COOH).

| CHN analysis: | Calc. | C 53.24; | H 5.16; | N 14.33. |
|---|---|---|---|---|
| | Found | C 53.3; | H 5.1; | N 14.3. |

3-[2-(3-Ethoxycarbonyl-1-propyl)-2,3-dihydro-3-oxo-[1,2,4]triazolo[4,3-a]pyridin-6-carbonylamino]-2-[(phenylmethoxy)carbonylamino]propanoic acid, t-butyl ester (6.3)

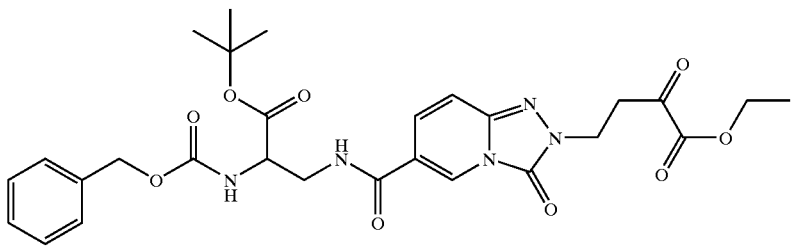

To a solution of 2-(3-ethoxycarbonyl-1-propyl)-2,3-dihydro-3-oxo-[1,2,4]triazolo[4,3-a]pyridin-6-carboxylic acid (950 mg, 3.24 mmoles) in dry dimethylformamide (20 ml) were added successively N,N-diisopropylethylamin (1.69 ml, 9.70 mmoles), O-benzotriazol-1-yl-N,N,N',N'-tetramethyluronium tetrafluoroborate (1.41 g, 4.40 mmoles) and 3-amino-2-(benzyloxycarbonylamino)propanoic acid t-butyl ester (900 mg, 3.06 mmoles) and the mixture was stirred at room temperature under inert atmosphere during 48 hours. After the addition of ethyl acetate (100 ml), the organic layer was washed with 1N hydrochloric acid (2×50 ml), with saturated sodium hydrogenocarbonate solution (2×50ml), brine (1×50 ml), dried over magnesium sulfate and evaporated to dryness under reduced pressure. The residue was chromatographed (silica gel; elution with ethyl acetate/triethylamine 98/2 v/v) giving a light yellow oil (1.00 g, 54%).

TLC: $R_f=0.75$ (silica gel; ethyl acetate/triethylamine 98/2 v/v).

IR (CHCl$_3$): 3409, 3344 (NH), 1726, 1670 (C=O), 1641, 1629, 1560, 1529, 1506 cm$^{-1}$ (C=C+C=N+amide).

$^1$H NMR (CDCl$_3$) 300 MHz: 1.24 (t, 3H, CH$_3$), 1.47 (s, 9H, t-Bu), 2.17 (m, 2H, CH$_2$), 2.39 (t, 2H, CH$_2$), 3.81 (m, 2H, CH$_2$), 4.06 (t, 2H, CH$_2$), 4.12 (q, 2H, CH$_2$), 4.46 (m, 1H, CH), 5.12 (AB, 2H, CH$_2$Ph), 5.96 (broad d, 1H, NH), 7.07 (dd, 1H, arom.), 7.31 (m, 5H, arom.), 7.34 (m, 1H, NH), 7.44 (dd, 1H, arom.), 8.36 ppm (broad s, 1H, arom.).

| CHN analysis: | Calc. | C 59.04; | H 6.19; | N 12.29. |
|---|---|---|---|---|
| | Found | C 58.7; | H 6.1; | N 12.2. |

3-[2-(3-Guanidinocarbonyl-1-propyl)-2,3-dihydro-3-oxo-[1,2,4]triazolo[4,3-a]pyridin-6-carbonylamino]-2-[(phenylmethoxy)carbonylamino]propanoic acid, t-butyl ester (6.4)

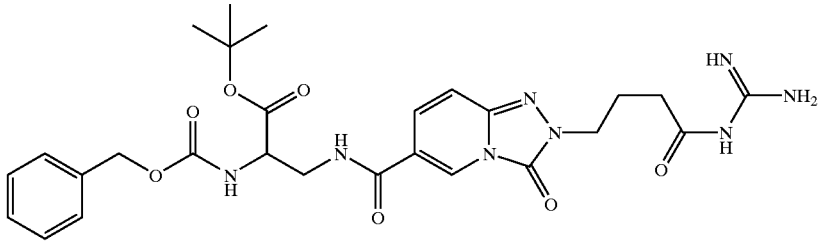

A mixture of 3-[2-(3-ethoxycarbonyl-1-propyl)-2,3-dihydro-3-oxo-[1,2,4]triazolo[4,3-a]pyridin-6-carbonylamino]-2-[(phenylmethoxy)carbonylamino] propanoic acid t-butyl ester (295 mg, 0.52 mmoles) and guanidine base (152 mg, 2.57 mmoles) in dry dimethylformamide (10 ml) was stirred at room temperature under inert atmosphere during 30 hours. The mixture was evaporated to dryness under reduced pressure and the residue was chromatographed (silica gel; elution with dichloromethane/methanol/water/acetic acid 70/30/1/1 v/v/v/v) giving a light coloured powder (60 mg, 20%).

Melting point: 110° C. decomp.

TLC: $R_f=0.20$ (silica gel; dichloromethane/methanol/water/acetic acid 90/10/1/1 v/v/v/v).

IR (CHCl$_3$): 3364 (NH/NH$_2$), 1713 (C=O), 1669, 1602, 1532, cm$^{-1}$ (C=O+C=N+C=C+NH/NH$_2$).

$^1$H NMR (DMSO-d$_6$) 300 MHz: 1.35 and 1.39 (s, 9H, tBu), 1.95 (m, 2H, CH$_2$), 2.17 (t, 2H, CH$_2$), 3.57 (m, 2H, CH$_2$), 3.90 (t, 2H, CH$_2$), 4.21 (q, 1H, CH), 5.04 (AB, 2H, CH$_2$Ph), 7.25–7.40 (m, 5H, arom.), 7.27 (d, 1H, arom.), 7.52 (dd, 1H, arom.), 7.70 (broad d, NH), 8.45 (broad s, 1H, arom.), 8.65 ppm (t, 1H, NH).

| Mass spectrum: | 583 (MH+). | | | |
|---|---|---|---|---|
| CHN analysis: | Calc. | C 55.66; | H 5.88; | N 19.23. |
| | Found | C 51.8; | H 6.1; | N 14.8. |

3-[2-(3-Guanidinocarbonyl-1-propyl)-2,3-dihydro-3-oxo-[1,2,4]triazolo[4,3-a]pyridin-6-carbonylamino]-2-[(phenylmethoxy)carbonylamino]propanoic acid (6.5)

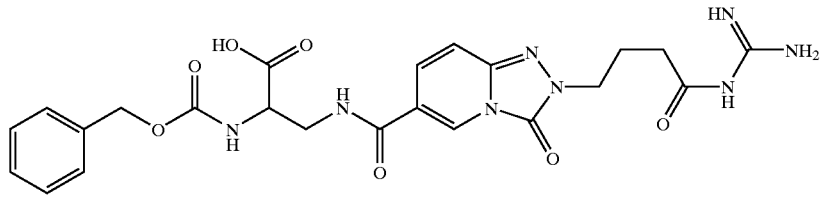

To a solution of 3-[2-(3-guanidinocarbonyl-1-propyl)-2,3-dihydro-3-oxo-[1,2,4]triazolo[4,3-a]pyridin-6-carbonylamino]-2-[(phenylmethoxy)carbonylamino] propanoic acid t-butyl ester (60 mg, 0.10 mmoles) in dichloromethane (10 ml) cooled to 0° C. was added trifluoroacetic acid (3 ml). After reaching room temperature the solution was stirred further 7 hours. The mixture was evaporated to dryness under reduced pressure after having added toluene (20 ml). The residue was chromatographed (silicagel; elution with chloroform/methanol/water/acetic acid 70/30/6/3 v/v/v/v) giving a pale yellow powder (17 mg, 31%).

Melting point: 190° C. decomp.

TLC: $R_f$=0.50 (silica gel; chloroform/methanol/water/acetic acid 70/30/6/3 v/v/v/v).

IR (Nujol): 1705 (C=O), 1650 (C=O+C=N), 1595, 1525 cm$^{-1}$ (arom.+amide).

$^1$H NMR (DMSO-d$_6$) 300 MHz: 1.98 (m, 2H, CH$_2$), 2.34 (t, 2H, CH$_2$), 2.50 (hidden m, 2H, CH$_2$), 3.89 (t, 2H, CH$_2$), 3.95 (q, 1H, CH), 4.99 (m, 2H, CH$_2$Ph), 6.81 (broad s, 1H, NH), 7.20–7.38 (m, 7H, arom.+NH), 7.47 (d, 1H, arom.), 8.30 (broad s, 1H, NH), 8.36 (s, 1H, arom.), 8.44 (broad s, NH).

Mass spectrum: 527 (MH+), 549 (MNa+).

Example 7

2-Benzyloxycarbonylamino-3-[6-(guanidinocarbonylmethyloxy)-3,4-dihydro-1-oxo-2(1H)-isoquinolyl]propanoic acid (7.10)

The synthesis was carried out according to the following procedures.

2-(Acetylamino)-3-[6-(benzyloxy)-3,4-dihydro-1-oxo-2(1H)-isoquinolyl]propanoic acid, methyl ester (7.1)

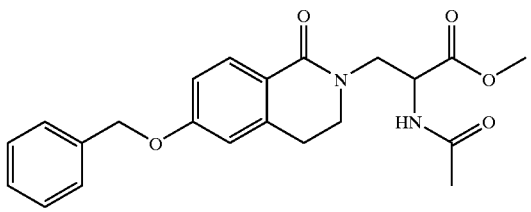

To a suspension of 6-(benzyloxy)-3,4-dihydro-1-oxo-2(1H)-isoquinoline [prepared by the method described in J.Med.Chem. (1997), 40(13), 2085–2101] (1.41 g, 5.57 mmoles) and of dry cesium fluoride (1.68 g, 11.06 mmoles) in tetrahydrofuran (15 ml) under inert atmosphere was added tetramethoxysilane (4 ml, 27.12 mmoles) at room temperature. The mixture was stirred at room temperature during 1 hour and then heated to 50° C. At this temperature was added within 1 hour a solution of methyl 2-acetamidoacrylate (1.60 g, 11.18 mmoles) in tetrahydrofuran (7 ml). The mixture was maintained at 50° C. during 1 hour and after cooling to room temperature evaporated to dryness under reduced pressure. The residue was chromatographed (silicagel; elution with ethyl acetate/dichloromethane 50/50 v/v) giving the wanted compound as an oil (0.7 g, 31%).

TLC: $R_f$=0.26 (ethyl acetate/dichloromethane 60/40 v/v)

$^1$H NMR (CDCl$_3$) 250 MHz: 1.95 (s, 3H, CH$_3$), 2.80–3.00 (m, 2H, CH$_2$), 3.40–3.65 (m, 2H, CH$_2$), 3.65–3.80 (m, 1H, CH$_2$), 3.70 (s, 3H, CH$_3$), 3.90–4.05 (m, 1H, CH$_2$), 4.60–4.80 (m, 1H, CH), 5.05 (s, 2H, CH$_2$Ph), 6.70 (d, 1H, arom.), 6.90 (dd, 1H, arom.), 7.05 (d, 1H, NH), 7.25–7.45 (m, 5H, arom.), 7.95 ppm (d, 1H, arom.).

2-Amino-3-[6-(benzyloxy)-3,4-dihydro-1-oxo-2(1H)-isoquinolyl]propanoic acid, methyl ester (7.2)

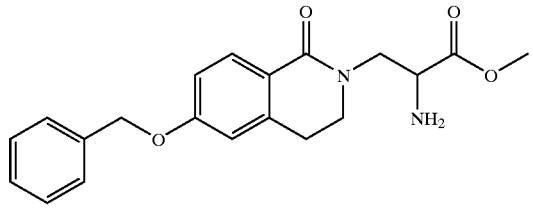

A mixture of 2-(acetylamino)-3-[6-(benzyloxy)-3,4-dihydro-1-oxo-2(1H)-isoquinolyl]propanoic acid methyl ester (0.97 g, 2.45 mmoles) in methanol (25 ml) and of concentrated hydrochloric acid (4.2 ml) was stirred at 50° C. during 92 hours. After cooling to room temperature, the mixture was evaporated to dryness under reduced pressure and chromatographed (silica gel; elution with methanol/dichloromethane 3/97 v/v) giving crystals (0.19 g, 21%).

Melting point: 104° C.

TLC: $R_f$=0.05 (silica gel; methanol/dichloromethane 5/95 v/v).

IR (CHCl$_3$): 3390, 3316 (NH$_2$), 1737, 1643 (C=O), 1606, 1578, 1498 cm$^{-1}$ (arom.+NH$_2$).

$^1$H NMR (CDCl$_3$) 250 MHz: 1.67 (broad s, 2H, NH$_2$), 2.85–3.05 (m, 2H, CH$_2$), 3.50–3.95 (m, 5H, 2CH$_2$+CH), 3.75 (s, 3H, CH$_3$), 5.20 (s, 2H, CH$_2$), 6.75 (d, 1H, arom.), 6.91 (dd, 1H, arom.), 7.25–7.45 (m, 5H, arom.), 8.00 ppm (d, 1H, arom.).

| Mass spectrum: | 355 (MH+), 377 (MNa+). | | |
|---|---|---|---|
| CHN analysis: | Calc. | C 67.78; | H 6.26; | N 7.90. |
| | Found | C 67.3; | H 6.4; | N 7.9. |

2-Benzyloxycarbonylamino-3-[6-(benzyloxy)-3,4-dihydro-1-oxo-2(1H)-isoquinolyl]propanoic acid, methyl ester (7.3)

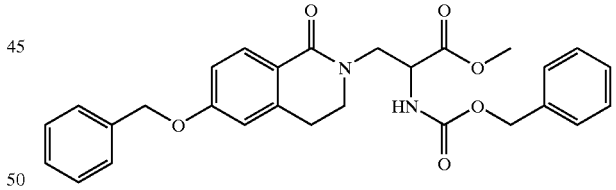

To a suspension of 2-amino-3-[6-(benzyloxy)-3,4-dihydro-1-oxo-2(1H)-isoquinolyl]propanoic acid methyl ester (0.61 g, 1.72 mmoles) in 1,2-dimethoxyethane (6 ml) was added at room temperature and under inert atmosphere a solution of N-(benzyloxycarbonyloxy)succinimide (0.45 g, 1.80 mmoles) in 1,2-dimethoxyethane (13 ml). The mixture was stirred at room temperature during 2 hours and evaporated to dryness under reduced pressure. The residue was chromatographed (silica gel; elution with methanol/dichloromethane 3/97 v/v) giving an oil (0.84 g, quantitative).

TLC: $R_f$=0.25 (silica gel; methanol/dichloromethane 5/95 v/v).

IR (CHCl$_3$): 3422 (NH), 1746, 1719, 1642 (C=O), 1606, 1578, 1512, 1500, 1480 cm$^{-1}$ (arom.+amide).

¹H NMR (CDCl₃) 300 MHz: 2.81 (t, 2H, CH₂), 3.45–3.60 (m, 2H, CH₂), 3.76 (s, 3H, CH₃), 3.80 (dd, 1H, CH₂), 4.03 (dd, 1H, CH₂), 4.45–4.57 (m, 1H, CH), 5.06 (m, 4H, CH₂Ph), 6.14 (broad d, 1H, NH), 6.73 (d, 1H, arom.), 6.92 (dd, 1H, arom.), 7.28 (m, 5H, arom.), 7.40 (m, 5H, arom.), 7.97 ppm (d, 1H, arom.).

Mass spectrum: 489 (MH+), 511 (MNa+).

2-Benzyloxycarbonylamino-3-[6-(benzyloxy)-3,4-dihydro-1-oxo-2(1H)-isoquinolyl]propanoic acid (7.4)

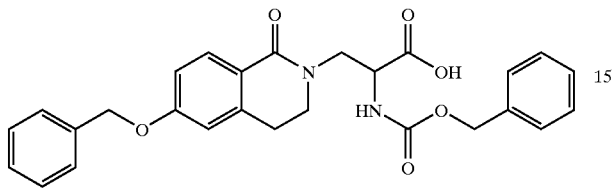

To 2-benzyloxycarbonylamino-3-[6-(benzyloxy)-3,4-dihydro-1-oxo-2(1H)-isoquinolyl]propanoic acid methyl ester (0.84 g, 1.72 mmoles) dissolved in methanol (6 ml) was added at room temperature a solution of 2N NaOH (1.2 ml, 2.4 mmoles) and the mixture was stirred at this temperature during 2 hours. After evaporation to dryness under reduced pressure, the residue was chromatographed (silica gel; elution with dichloromethane/methanol/acetic acid 98/2/1 v/v/v) giving an oil (0.73 g, 89%).

TLC: R_f=0.36 (silica gel; methanol/dichloromethane 10/90 v/v).

IR (CHCl₃): 3412 (NH), 1746, 1714, 1637 (C=O), 1604, 1577, 1507, 1498 cm⁻¹ (arom.+amide).

¹H NMR (CDCl₃) 250 MHz: 2.85 (m, 2H, CH₂), 3.45–4.50 (m, 5H, 2CH₂+CH), 5.06 (broad s, 4H, 2CH₂Ph), 6.68 (broad s, 1H, arom.), 6.85 (m, 1H, arom.), 7.20–7.40 (m, 10H, arom.), 7.94 ppm (m, 1H, arom.).

Mass spectrum: 473 (M−H).

2-Benzyloxycarbonylamino-3-[6-(benzyloxy)-3,4-dihydro-1-oxo-2(1H)-isoquinolyl]propanoic acid, t-butyl ester (7.5)

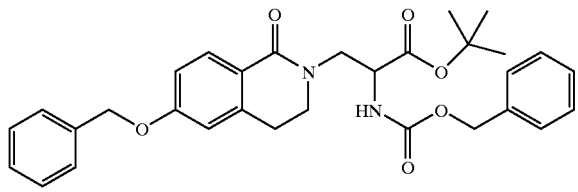

A mixture of 2-benzyloxycarbonylamino-3-[6-(benzyloxy)-3,4-dihydro-1-oxo-2(1H)-isoquinolyl]propanoic acid (0.71 g, 1.49 mmoles) and dimethylformamide ditert-butylacetal (15 ml) was heated at 90° C. during 3 hours under inert atmosphere. The solution was evaporated to dryness under reduced pressure and the residue chromatographed (silica gel; elution with methanol/dichloromethane 1/99 v/v) giving an oil (0.57 g, 72%).

TLC: R_f=0.73 (silica gel; methanol/dichloromethane 10/90 v/v).

IR (CHCl₃): 3424 (NH), 1740, 1714, 1648, 1631 (C=O), 1606, 1579, 1505, 1499 cm⁻¹ (arom.+amide).

¹H NMR (CDCl₃) 250 MHz: 1.35 (s, 9H, tBu), 2.80–3.10 (m, 2H, CH₂), 3.50–3.75 (m, 2H, CH₂), 3.85 (mAB, 2H, CH₂), 4.45 (m, 1H, CH), 5.05 (s, 2H, CH₂Ph), 5.10 (s, 2H, CH₂Ph), 5.90 (broad d, 1H, NH), 6.65 (d, 1H, arom.), 6.90 (dd, 1H, arom.), 7.10–7.40 (m, 10H, arom.), 7.90 ppm (d, 1H, arom.).

Mass spectrum: 553 (MNa+).

2-Amino-3-[3,4-dihydro-6-hydroxy-1-oxo-2(1H)-isoquinolyl]propanoic acid, tert-butyl ester (7.6)

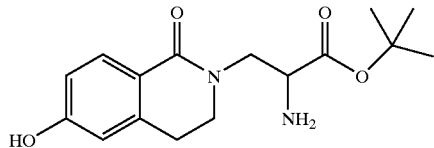

A mixture of 2-benzyloxycarbonylamino-3-[6-(benzyloxy)-3,4-dihydro-1-oxo-2(1H)-isoquinolyl] propanoic acid t-butyl ester (0.55 g, 1.03 mmoles), 20% palladium hydroxide on charcoal (0.28 g) and cyclohexene (2.4 ml) in methanol (15 ml) was refluxed during 3 hours. After filtration on clarcel, the filtrate was evaporated to dryness under reduced pressure. The residue was chromatographed (silica gel; elution with methanol/dichloromethane 5/95 v/v) giving an oil (0.11 g, 34%).

TLC: R_f=0.15 (silica gel; dichloromethane/methanol/acetic acid/water 90/10/1/1 v/v/v/v).

¹H NMR (CDCl₃) 250 MHz: 1.40 (s, 9H, t-Bu), 2.65–2.80 (m, 2H, CH₂), 3.45–3.75 (m, 4H, CH₂+exchangeable), 3.80–4.20 (m, 4H, CH+CH₂+exchangeable), 6.35 (broad s, 1H, arom.), 6.55 (dd, 1H, arom.), 7.65 ppm (d, 1H, arom.).

Mass spectrum: 305 (M−H), 249 (M−tBu), 162.

2-Benzyloxycarbonylamino-3-[3,4-dihydro-6-hydroxy-1-oxo-2(1H)-isoquinolyl]propanoic acid, tert-butyl ester (7.7)

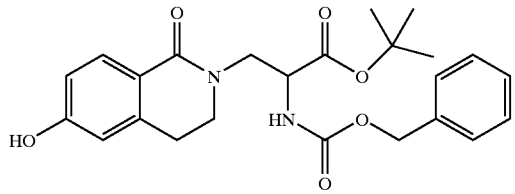

To a solution of 2-amino-3-[3,4-dihydro-6-hydroxy-1-oxo-2(1H)-isoquinolyl]propanoic acid t-butyl ester (0.110 g, 0.36 mmoles) in 1,2-dimethoxyethane (1.3 ml) was added dropwise at room temperature and under inert atmosphere a solution of N-(benzyloxycarbonyloxy)succinimide (0.094 g, 0.38 mmoles) in 1,2-dimethoxyethane (3 ml). The mixture was stirred at room temperature during 2 hours, evaporated to dryness under reduced pressure and the residue chromatographed (silica gel; elution with dichloromethane/methanol 97/3 v/v) giving an oil (0.16 g, quantitative).

TLC: R_f=0.50 (silica gel; dichloromethane/methanol 90/10 V/V).

IR (CHCl₃): 3594 (OH), 3424 (NH), 1744, 1715, 1642 (C=O), 1611, 1587, 1507, 1480 cm⁻¹ (arom.+amide).

¹H NMR (CDCl 3) 250 MHz: 1.43 (s, 9H, t-Bu), 2.85 (m, 2H, CH₂), 3.58 (m, 2H, CH₂), 3.78 and 3.99 (AB dd, 2H, CH₂), 4.47 (m, 1H, CH), 5.06 (s, 2H, CH₂Ph), 5.84 (broad d, 1H, NH), 6.59 (d, 1H, arom.), 6.75 (dd, 1H, arom.), 7.27 (broad s, 5H, arom.), 7.90 (d, 1H, arom.). Mass spectrum: 439 (M−H), 275, 162.

2-Benzyloxycarbonylamino-3-[3,4-dihydro-6-(methoxycarbonylmethyloxy)-1-oxo-2(1H)-isoquinolyl]propanoic acid, tert-butyl ester (7.8)

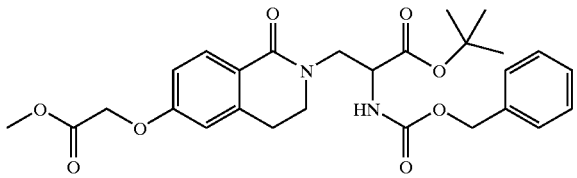

A mixture of 2-benzyloxycarbonylamino-3-[3,4-dihydro-6-hydroxy-1-oxo-2(1H)-isoquinolyl]propanoic acid t-butyl ester (140 mg, 0.32 mmoles), cesium carbonate (220 mg, 0.67 mmoles) and methyl bromoacetate (56 mg, 0.37 mmoles) in acetonitrile (10 ml) is refluxed during half an hour. The mixture was evaporated to dryness under reduced pressure and the residue was chromatographed (silica gel; elution with dichloromethane/ethyl acetate 90/10 v/v) giving an oil (117 mg, 72%).

TLC: $R_f$=0.45 (silica gel; dichloromethane/ethyl acetate 80/20 v/v).

IR (CHCl$_3$): 3420 (NH), 1754, 1737, 1717, 1644 (C=O), 1607, 1580, 1513, 1502 (arom.+amide), 1440 (CO$_2$Me), 1370 cm$^{-1}$ (CO$_2$tBu).

$^1$H NMR (CDCl$_3$) 250 MHz: 1.43 (s, 9H, tBu), 2.90 (t, 2H, CH$_2$), 3.59 (m, 2H, CH$_2$), 3.82 (s, 3H, CH$_3$), 3.90–4.20 (m, 2H, CH$_2$), 4.47 (m, 1H, CH), 4.68 (s, 2H, CH$_2$CO), 5.04 (s, 2H, CH$_2$Ph), 5.89 (d, 1H, NH), 6.67 (d, 1H, arom.), 6.82 (dd, 1H, arom.), 7.24–7.40 (m, 5H, arom.), 8.00 ppm (d, 1H, arom.).

Mass spectrum: 535 (MNa+).

2-Benzyloxycarbonylamino-3-[6-(guanidinocarbonylmethyloxy)-3,4-dihydro-1-oxo-2(1H)-isoquinolyl]propanoic acid, tert-butyl ester (7.9)

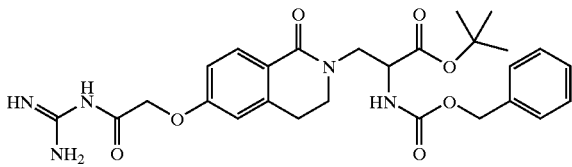

A mixture of 2-benzyloxycarbonylamino-3-[3,4-dihydro-6-(methoxycarbonylmethyloxy)-1-oxo-2(1H)-isoquinolyl]propanoic acid t-butyl ester (55 mg, 0.11 mmoles) and guanidine base (13 mg, 0.22 mmoles) in dry dimethylformamide (1 ml) was stirred at room temperature under inert atmosphere during 1 hour. The mixture was evaporated to dryness under reduced pressure and the residue was dissolved in the minimum of dichloromethane and methanol and poured into diisopropyl ether. The solid was collected by filtration and dried under vacuum giving an amorphous powder (18 mg, 31%).

TLC: $R_f$=0.60 (silica gel; dichloromethane/methanol/acetic acid/water 85/15/2/2 v/v/v/v).

IR (CHCl$_3$): 3508, 3475, 3418 (NH/NH$_2$), 1736, 1716 (C=O), 1639 (C=O), 1606, 1577, 1516, 1500, 1480 cm$^{-1}$ (C=N+arom.+amide+NH/NH$_2$)

$^1$H NMR (DMSO-d$_6$) 300 MHz: 1.26–1.34 (2s, 9H, tBu), 2.63 (m, 2H, CH$_2$), 3.31(m, 1H, CH$_2$), 3.53 (m, 2H, CH$_2$), 4.11 (dd, 1H, CH$_2$), 4.29 (m, 1H, CH), 4.49 (s, 2H, CH$_2$CO), 5.02 (s, 2H, CH$_2$Ph), 6.69 (d, 1H, arom.), 6.78 (dd, 1H, arom.), 7.26–7.31 (m, 5H, arom.), 7.74 ppm (d, 1H, arom.).

| Mass spectrum: | 562 (MNa+), 540 (MH+), 484 (M-tBu), 440, 423. | | |
|---|---|---|---|
| CHN analysis: | Calc. | C 60.10; | H 6.16; | N 12.98. |
| | Found | C 58.5; | H 6.1; | N 12.8. |

2-Benzyloxycarbonylamino-3-[6-(guanidinocarbonylmethyloxy)-3,4-dihydro-1-oxo-2(1H)-isoquinolyl]propanoic acid (7.10)

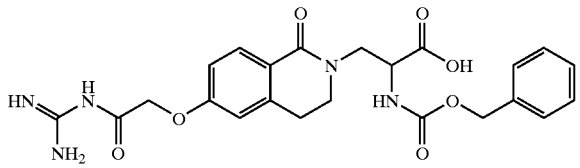

To a solution of 2-benzyloxycarbonylamino-3-[6-(guanidinocarbonylmethyloxy)-3,4-dihydro-1-oxo-2(1H)-isoquinolyl]propanoic acid t-butyl ester (37.8 mg, 0.07 mmoles) in dichloromethane (10 ml) was dropwise added at room temperature trifluoroacetic acid (3.5 ml). The mixture was stirred at room temperature during 3 hours, toluene (20 ml) was added and the whole was evaporated to dryness under reduced pressure. The residue was dissolved in acetic acid and precipitated isopropyl ether. The resulting powder was dried under vacuum giving an amorphous solid (8.7 mg, 25%).

TLC: $R_f$=0.25 (silica gel; dichloromethane/methanol/acetic acid/water 85/15/2/2 v/v/v/v).

IR (Nujol): 1704, 1634 (C=O), 1602 cm$^{-1}$ (arom.+amide).

$^1$H NMR (DMSO-d$_6$) 300 MHz: 2.79 (m, 2H, CH$_2$), 3.52 (m, 2H, CH$_2$), 3.52 and 3.85 (2m, 2H, CH$_2$), 4.11 (m, 1H, CH), 4.49–4.86 (2s, 2H, CH$_2$CO), 4.95 (AB, 2H, CH$_2$Ph), 6.66 and 6.70 (2d, 1H, arom.), 6.77 and 6.87 (2dd, 1H, arom.), 7.25–7.31 (m, 5H, arom.), 7.74 and 7.78 ppm (2d, 1H, arom.).

Mass spectrum: 506 (MNa+), 484 (MH+).

The inhibition of bone resorption by the novel compounds can be determined, for example, using an osteoclast resorption test (PIT ASSAY), for example in analogy with WO 95/32710. The test methods which can be used to determine the antagonistic effect of the novel compounds on the vitronectin receptor $\alpha_v\beta_3$ are described below.

Test Method 1

Inhibition of the Binding of Human Vitronectin (Vn) to Human Vitronectin Receptor (VnR) $\alpha_v\beta_3$: ELISA Test
(Test method 1 is designated Vn/VnR for short)

1. Purification of Human Vitronectin

Human vitronectin is isolated from human plasma and purified by affinity chromatography using the method of Yatohyo et al., Cell Structure and Function, 1988, 23, 281–292.

2. Purification of Human Vitronectin Receptor ($\alpha_v\beta_3$)

Human vitronectin receptor is isolated from the human placenta using the method of Pytela et al., Methods Enzymol. 1987, 144, 475. Human vitronectin receptor $\alpha_v\beta_3$ can also be isolated from some cell lines (e.g. from 293 cells, which is a human embryonic kidney cell line) which have been cotransfected with DNA sequences for both the subunits, i.e. $\alpha_v$ and $\beta_3$, of the vitronectin receptor. The subunits are extracted with octyl glycoside and then chromatographed through concanavalin A, heparin-Sepharose and S-300.

3. Monoclonal Antibodies

Murine monoclonal antibodies which are specific for the $\beta_3$ subunit of the vitronectin receptor are prepared using the method of Newman et al., Blood, 1985, 227–232, or using a similar method. Horseradish peroxidase-conjugated rabbit Fab 2 anti-mouse Fc (anti-mouse Fc HRP) was obtained from Pel Freeze (Catalog No. 715 305-1).

4. ELISA Test

Nunc Maxisorb 96-well microtiter plates are coated at 4° C. overnight with a solution of human vitronectin (0.002 mg/ml, 0.05 ml/well) in PBS (phosphate-buffered sodium chloride solution). The plates are washed twice with PBS/0.05% Tween 20 and blocked by incubating (60 min) with bovine serum albumin (BSA, 0.5%, RIA quality or better) in Tris-HCl (50 mM), NaCl (100 mM), $MgCl_2$ (1 mM), $CaCl_2$ (1 mM), $MnCl_2$ (1 mM), pH 7. Solutions of known inhibitors and of the test substances, in concentrations of from $2 \times 10^{-12}$ to $2 \times 10^{-6}$ mol/l, are prepared in assay buffer [BSA (0.5%, RIA quality or better) in Tris-HCl (50 mM), NaCl (100 mM), $MgCl_2$ (1 mM), $CaCl_2$ (1 mM), $MnCl_2$ (1 mM), pH 7]. The blocked plates are emptied and in each case 0.025 ml of this solution, which contains a defined concentration (from $2 \times 10^{-12}$ to $2 \times 10^{-6}$) of either a known inhibitor or of a test substance, is added to each well. 0.025 ml of a solution of the vitronectin receptor in the test buffer (0.03 mg/ml) is pipetted into each well of the plate and the plate is incubated on a shaker at room temperature for 60–180 min. In the meantime, a solution (6 ml/plate) of a murine monoclonal antibody which is specific for the $\beta_3$ subunit of the vitronectin receptor is prepared in the assay buffer (0.0015 mg/ml). A second rabbit antibody, which is an anti-mouse Fc HRP antibody conjugate, is added to this solution (0.001 ml of stock solution/6 ml of the murine monoclonal anti-$\beta_3$ antibody solution), and this mixture composed of murine anti-$\beta_3$ antibody and rabbit anti-mouse Fc HRP antibody conjugate is left to incubate during the period of the receptor/inhibitor incubation.

The test plates are washed 4 times with PBS solution containing 0.05% Tween-20, and in each case 0.05 ml/well of the antibody mixture is pipetted into each well of the plate and the plate is incubated for 60–180 min. The plate is washed 4 times with PBS/0.05% Tween-20 and then developed with 0.05 ml/well of a PBS solution which contains 0.67 mg/ml o-phenylenediamine and 0.012% $H_2O_2$. As an alternative, o-phenylenediamine can be used in a buffer (pH 5) which contains $Na_3PO_4$ (50 mM) and citric acid. The color development is stopped with 1N $H_2SO_4$ (0.05 ml/well). The absorption of each well is measured at 492–405 nm and the data are evaluated using standard methods.

Test Method 2

Inhibition of the Binding of Kistrin to Human Vitronectin Receptor (VnR)

$\alpha_v\beta_3$: ELISA Test (Test method 2 is designated kistrin/VnR for short)

1. Purification of Kistrin

Kistrin is purified using the methods of Dennis et al., as described in Proc. Natl. Acad. Sci. USA 1989, 87, 2471–2475 and PROTEINS: Structure, Function and Genetics 1993, 15, 312–321.

2. Purification of Human Vitronectin Receptor ($\alpha_v\beta_3$)

see test method 1.

3. Monoclonal Antibodies see test method 1.

4. ELISA Test

The ability of substances to inhibit the binding of kistrin to the vitronectin receptor can be ascertained using an ELISA test. For this purpose, Nunc 96-well microtiter plates are coated with a solution of kistrin (0.002 mg/ml) using the method of Dennis et al., as described in PROTEINS: Structure, Function and Genetics 1993, 15, 312–321. The subsequent experimental implementation of the ELISA test is as described in test method 1, item 4.

Test Method 3

Inhibition of the Binding of $\alpha_v\beta_3$-transfected 293 Cells to Human Vitronectin (Test method 3 is designated Vn/293 cell test for short)

Cell Test 293 cells, a human embryonic kidney cell line, which are cotransfected with DNA sequences for the $\alpha_v$ and $\beta_3$ subunits of the vitronectin receptor $\alpha_v\beta_3$ are selected for a high rate of expression (>500,000 $\alpha_v\beta_3$ receptors/cell) using the FACS method. The selected cells are cultured and re-sorted by FACS in order to obtain a stable cell line (15 D) having expression rates of >1,000,000 copies of $\alpha_v\beta_3$ per cell.

A Limbro 96-well tissue culture plate having a flat bottom is coated at 4° C. overnight with human vitronectin (0.01 mg/ml, 0.05 ml/well) in phosphate-buffered sodium chloride solution (PBS) and then blocked with 0.5% BSA. Solutions of the test substances having concentrations of from $10^{-10}$ to $2 \times 10^{-3}$ mol/l are prepared in glucose-containing DMEM medium, and in each case 0.05 ml/well of the solution is added to the plate. The cells which are expressing high levels of $\alpha_v\beta_3$ (e.g. 15 D) are suspended in glucose-containing DMEM medium and the suspension is adjusted to a content of 25,000 cells/0.05 ml of medium. 0.05 ml of this cell suspension is then added to each well and the plate is incubated at 37° C. for 90 min. The plate is washed 3× with warm PBS in order to remove unbound cells. The bound cells are lysed in citrate buffer (25 mM, pH 5.0) containing 0.25% Triton X-100. The hexose amidase substrate p-nitrophenyl-N-acetyl-$\beta$-D-glucosaminide is then added and the plate is incubated at 37° C. for 90 min. The reaction is stopped with a glycine (50 mM)/EDTA (5 mM) buffer (pH 10.4) and the absorption of each well is measured at 405–650 nm.

The antagonistic effect of the compounds of the present invention on the fibrinogen receptor $\alpha_{IIb}\beta_3$, in particular for determining selectivity, can be ascertained as described in U.S. Pat. No. 5,403,836, p. 237.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application No. 196 53 647.2, for which benefit under 35 USC § 119 is claimed, is expressly incorporated herein in its entirety.

What is claimed is:

1. A compound of formula I

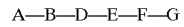
(I)

in which:

A=$A_1$ or $A_2$, where

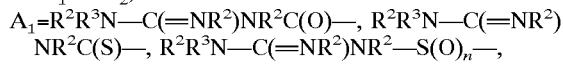

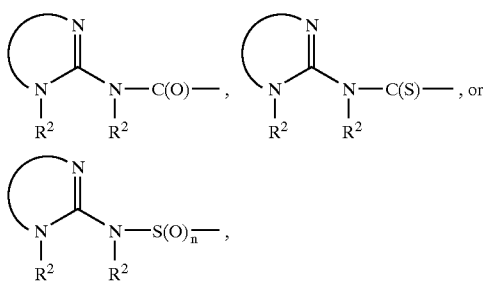

and $A_2$ = 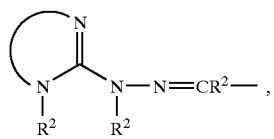

where, in $A_1$ or $A_2$, the radical:

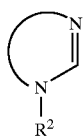

is a 5-membered to 10-membered monocyclic or polycyclic, aromatic or nonaromatic ring system which contains the grouping

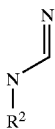

and, in addition, can contain from 1 to 4 heteroatoms selected from the group consisting of N, O, and S, and, optionally, can be substituted at least once by $R^{12}$, $R^{13}$, $R^{14}$ or $R^{15}$;

B is a direct linkage, $(C_1-C_8)$-alkanediyl, —$CR^2$=$CR^3$—, $(C_5-C_{10})$-arylene, $(C_3-C_8)$ cycloalkylene, or —C≡C—, which may in each case be substituted, once or twice, by $(C_1-C_8)$-alkyl, where the valence permits;

D is a direct linkage, $(C_1-C_8)$-alkanediyl, $(C_5-C_{10})$-arylene, —O—, —$NR^2$—, —CO—$NR^2$—, —$NR^2$—CO—, —$NR^2$—C(O)—$NR^2$—, —$NR^2$—C(S)—$NR^2$—, —OC(O)—, —C(O)O—, —CO—, —CS—, —S(O)—, —S(O)$_2$—, —S(O)$_2$—$NR^2$—, —S(O)—$NR^2$—, —$NR^2$—S(O)—, —$NR^2$—S(O)$_2$—, —S—, —$CR^2$=$CR^3$, —C≡C—, —$NR^2$—N=$CR^2$—, —N=$CR^2$, —$R^2$C=N— or —CH(OH)—, which may in each case be substituted, once or twice, by $(C_1-C_8)$-alkyl, —$CR^2$=$CR^2$—, or $(C_5-C_6)$-aryl, where the valence permits, where, if B is a direct linkage, then D can also be a direct linkage or a radical as defined under D, which radical is substituted once or twice, where the valence permits, as described under D, and is linked to B by way of one of these substituents;

E is selected from the group consisting of

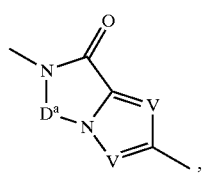
(i)

in which V is $CR^{7a}$ or N, and $D^a$ is $CH_2$, $CH_2$—$CH_2$, $CH_2C(R^{7a})_2CH_2$ or

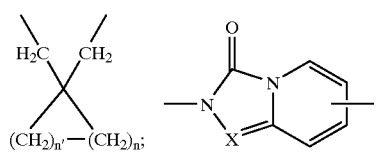
(ii)

in which X is $CR^{3a}$ or N, where $R^{3a}$ is CN, C(O)N($R^{7a}$)$R^{8a}$,

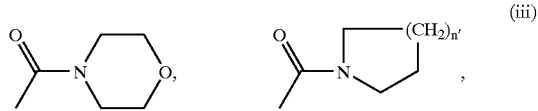
(iii)

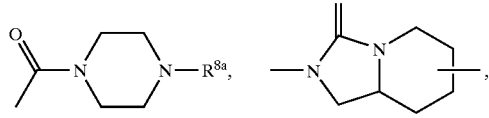

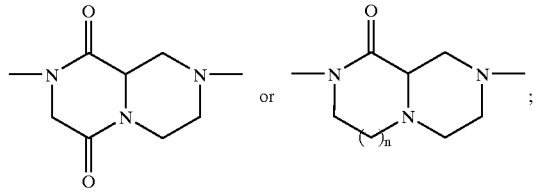

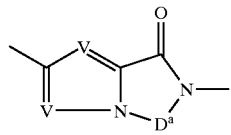

in which

V is $CR^{7a}$ or N, and $D^a$ is $CH_2$, $CH_2$—$CH_2$, $CH_2C(R^{7a})_2CH_2$ or

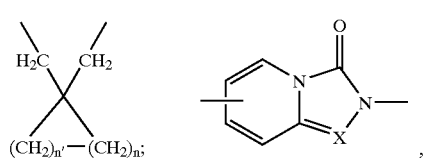
(iv)

in which

X is $CR^{3a}$ or N, in which $R^{3a}$ is CN, C(O)N(R$^{7a}$)R$^{8a}$, (v) [structures shown: acetyl-morpholine; acetyl-pyrrolidine-(CH$_2$)$_n'$]

(vi) [bicyclic piperazine-dione structure]

(vii) [N-methyl piperazine carboxamide structure with (CH$_2$)$_n'$]

[imidazopiperidinone structure with Y$^3$]

where Y$^3$ is O or H$_2$, and

R$^{7a}$ is hydrogen; C$_1$–C$_4$-alkyl which is optionally substituted by OH or (C$_1$–C$_4$)-alkoxy; C$_2$–C$_6$-alkenyl which is optionally substituted by (C$_1$–C$_4$)-alkoxy; or HO—(C$_1$–C$_4$)-alkylaryl; or aryl which is optionally substituted by identical or different radicals selected from the group consisting of halogen, (C$_1$–C$_4$)-alkoxy, hydroxyl and (C$_1$–C$_4$)-alkyl, R$^{8a}$ is halogen or C$_1$–C$_4$-alkyl, n is an integer from 0 to 7, and n' is an integer from 0 to 3

F is defined like D; and

G is

[structure: carbon chain with R$^4$, R$^5$, R$^6$, R$^7$ substituents and (CH$_2$)$_q$—R$^{10}$, with subscript p]

where

R$^2$ and R$^3$ are, independent of each other, hydrogen, (C$_1$–C$_{10}$)-alkyl, which is optionally substituted at least once by fluorine, (C$_3$–C$_{12}$)-cycloalkyl, (C$_3$–C$_{12}$)-cycloalkyl-(C$_1$–C$_8$)-alkyl, (C$_5$–C$_{14}$)-aryl, (C$_5$–C$_{14}$)-aryl-(C$_1$–C$_8$)-alkyl, R$^8$OC(O)R$^9$, R$^8$R$^8$NC(O)R$^9$, or R$^8$C(O)R$^9$;

R$^4$, R$^5$, R$^6$, and R$^7$ are, independent of each other, hydrogen, fluorine, OH, (C$_1$–C$_8$)-alkyl, (C$_3$–C$_{14}$)-cycloalkyl, (C$_3$–C$_{14}$)-cycloalkyl-(C$_1$–C$_8$)-alkyl, R$^8$OR$^9$, R$^8$SR$^9$, R$^8$CO$_2$R$^9$, or R$^8$C(O)R$^9$;

R$^4$, R$^5$, R$^6$, and R$^7$ are, independent of each other, hydrogen, fluorine, OH, (C$_1$–C$_8$)-alkyl, (C$_3$–C$_{14}$)-cycloalkyl, (C$_3$–C$_{14}$)-cycloalkyl-(C$_1$–C$_8$)-alkyl, R$^8$OR$^9$, R$^8$SR$^9$, R$^8$CO$_2$R$^9$, R$^8$OC(O)R$^9$, R$^8$—(C$_5$–C$_{14}$)-aryl-R$^9$, R$^8$N(R$^2$)R$^9$, R$^8$R$^8$NR$^9$, R$^8$N(R$^2$)C(O)OR$^9$, R$^8$S(O)$_n$N(R$^2$)R$^9$, R$^8$OC(O)N(R$^2$)R$^9$, R$^8$C(O)N(R$^2$)R$^9$, R$^8$N(R$^2$)C(O)N(R$^2$)R$^9$, R$^8$N(R$^2$)S(O)$_n$N(R$^2$)R$^9$, R$^8$S(O)$_n$R$^9$, R$^8$SC(O)N(R$^2$)R$^9$, R$^8$C(O)R$^9$, R$^8$N(R$^2$)C(O)R$^9$ or R$^8$N(R$^2$)S(O)$_n$R$^9$;

R$^8$ is hydrogen, (C$_1$–C$_8$)-alkyl, (C$_3$–C$_{14}$)-cycloalkyl, (C$_3$–C$_{14}$)-cycloalkyl-(C$_1$–C$_8$)-alkyl, (C$_3$–C$_{14}$)-aryl or (C$_3$–C$_{14}$)-aryl-(C$_1$–C$_8$)-alkyl, where the alkyl radicals can be substituted at least once by fluorine;

R$^9$ is a direct linkage or (C$_1$–C$_8$)-alkanediyl;

R$^{10}$ is C(O)R$^{11}$, C(S)R$^{11}$, S(O)$_n$R$^{11}$, P(O)(R$^{11}$)$_2$, or a four-membered to eight-membered, saturated or unsaturated heterocycle which contains 1, 2, 3, or 4 heteroatoms selected from the group consisting of N, O, and S;

R$^{11}$ is OH, (C$_1$–C$_8$)-alkoxy, (C$_5$–C$_{14}$)-aryl-(C$_1$–C$_8$)-alkoxy, (C$_5$–C$_{14}$)-aryloxy, (C$_1$–C$_8$)-alkylcarbonyloxy-(C$_1$–C$_4$)-alkoxy, (C$_5$–C$_{14}$)-aryl-(C$_1$–C$_8$)-alkylcarbonyloxy-(C$_1$–C$_6$)-alkoxy, NH$_2$, mono- or di-((C$_1$–C$_4$)-alkyl)-amino, (C$_5$–C$_{14}$)-aryl-(C$_1$–C$_{18}$)-alkylamino, (C$_1$–C$_8$)-dialkylaminocarbonylmethyloxy, (C$_5$–C$_{14}$)-aryl-(C$_1$–C$_8$)-dialkylaminocarbonylmethyloxy, (C$_5$–C$_{14}$)-arylamino, or a radical of an L-amino acid or D-amino acid;

R$^{12}$, R$^{13}$, R$^{14}$, and R$^{15}$ are, independent of each other, hydrogen, (C$_1$–C$_{10}$)-alkyl which is optionally substituted once or more than once by fluorine, (C$_3$–C$_{12}$)-cycloalkyl, (C$_3$–C$_{12}$)-cycloalkyl-(C$_1$–C$_8$)-alkyl, (C$_5$–C$_{14}$)-aryl, (C$_5$–C$_{14}$)-aryl-(C$_1$–C$_8$)-alkyl, H$_2$N, R$^8$ONR$^9$, R$^8$OR$^9$, R$^8$OC(O)R$^9$, R$^8$R$^8$NR$^9$, R$^8$—(C$_5$–C$_{14}$)-aryl-R$^9$, HO—(C$_1$–C$_8$)-alkyl-N(R$^2$)R$^9$, R$^8$N(R$^2$)C(O)R$^9$, R$^8$C(O)N(R$^2$)R$^9$, R$^8$C(O)R$^9$, R$^2$R$^3$N—C(=NR$^2$)—NR$^2$, R$^2$R$^3$N—C(=NR$^2$), =O, or =S;

where two adjacent substituents from R$^{12}$, R$^{13}$, R$^{14}$, and R$^{15}$ can also together be —OCH$_2$O—, —OCH$_2$CH$_2$O—, or —OC(CH$_3$)O—;

n is 1 or 2;

p and q are, independently of each other, 0 or 1;

in all its stereoisomeric forms and mixtures thereof in all proportions, and its physiologically tolerated salts.

2. A compound of formula I as claimed in claim 1, wherein:

A=A$_1$ or A$_2$, where

A$_1$ = R$^2$R$^3$N—C(=NR$^2$)NR$^2$C(O)—   or

[cyclic structure with N, N—C(O)—, R$^2$ substituents]   and

A$_2$ = [cyclic structure with N, N—N=CR$^2$—, R$^2$ substituents]

where, in A$_1$ or A$_2$, the radical

[cyclic N structure with R$^2$]

is a 5-membered to 10-membered monocyclic or polycyclic, aromatic or nonaromatic ring system which contains the grouping

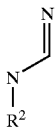

and, in addition, can contain from 1 to 4 heteroatoms selected from the group consisting of N, O, and S and, optionally can be substituted once or more than once by $R^{12}$, $R^{13}$, $R^{14}$ and $R^{15}$;

B is a direct linkage, —NH—, —O—, $(C_1-C_6)$-alkanediyl, $(C_5-C_8)$-arylene, $(C_5-C_6)$ cycloalkylene, —$CR^2$=$CR^3$— or —C≡C—, which may in each case be substituted, once or twice, by $(C_1-C_3)$-alkyl, where the valence permits;

D is a direct linkage, $(C_1-C_8)$-alkanediyl, $(C_5-C_{10})$-arylene, —O—, —$NR^2$—, —CO—$NR^2$—, —$NR^2$—CO—, —$NR^2$—C(O)—$NR^2$—, —$NR^2$—C(S)—$NR^2$—, —OC(O)—, —C(O)O—, —CO—, —S(O)$_2$—, —S(O)$_2$—$NR^2$—, —$NR^2$—S(O)$_2$—, —S—, —$CR^2$=$CR^3$, —C≡C—, —N=$CR^2$ or —$R^2$C=N—, which may in each case be substituted, once or twice, by $(C_1-C_8)$-alkyl, —$CR^2$=$CR^2$— or $(C_5-C_6)$-aryl, where the valence permits, where, if B is a direct linkage, then D can also be a direct linkage or a radical as defined under D, which radical is substituted once or twice, where the valence permits, as described under D, and is linked to B by way of one of these substituents;

F is defined like D; and

G is

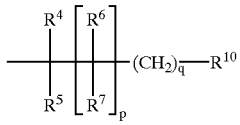

wherein $R^2$ and $R^3$ are, independent of each other, hydrogen, $(C_1-C_{10})$-alkyl, which is optionally substituted at least once by fluorine, $(C_3-C_8)$-cycloalkyl, $(C_3-C_8)$-cycloalkyl-$(C_1-C_6)$-alkyl, $(C_5-C_{12})$-aryl, $(C_5-C_{12})$-aryl-$(C_1-C_6)$-alkyl, $R^8OC(O)R^9$, $R^8R^8NC(O)R^9$, or $R^8C(O)R^9$;

$R^4$, $R^5$, $R^6$, and $R^7$ are, independent of each other, hydrogen, fluorine, OH, $(C_1-C_8)$-alkyl, $(C_5-C_{14})$-cycloalkyl, $(C_3-C_{14})$-cycloalkyl-$(C_1-C_8)$-alkyl, $R^8OR^9$, $R^8SR^9$, $R^8CO_2R^9$, $R^8OC(O)R^9$, $R^8$—$(C_3-C_{14})$-aryl-$R^9$, $R^8N(R^2)R^9$, $R^8R^8NR^9$, $R^8N(R^2)C(O)OR^9$, $R^8S(O)_nN(R^2)R^9$, $R^8OC(O)N(R^2)R^9$, $R^8C(O)N(R^2)R^9$, $R^8N(R^2)C(O)N(R^2)R^9$, $R^8N(R^2)S(O)_nN(R^2)R^9$, $R^8S(O)_nR^9$, $R^8SC(O)N(R^2)R^9$, $R^8C(O)R^9$, $R^8N(R^2)C(O)R^9$, or $R^8N(R^2)S(O)_nR^9$;

$R^8$ is hydrogen, $(C_1-C_6)$-alkyl, $(C_5-C_{14})$-cycloalkyl, $(C_5-C_{14})$-cycloalkyl-$(C_1-C_6)$-alkyl, $(C_5-C_{12})$-aryl or $(C_5-C_{12})$-aryl-$(C_1-C_6)$-alkyl, where the alkyl radicals may be substituted at least once by fluorine;

$R_9$ is a direct linkage or $(C_1-C_6)$-alkanediyl;

$R^{10}$ is $C(O)R^{11}$, $C(S)R^{11}$, $S(O)_nR^{11}$, $P(O)(R^{11})_2$, or a four-membered to eight-membered, saturated or unsaturated heterocycle which contains 1, 2, 3, or 4 heteroatoms selected from the group consisting of N, O, and S;

$R^{11}$ is OH, $(C_1-C_6)$-alkoxy, $(C_5-C_{12})$-aryl-$(C_1-C_6)$-alkoxy, $(C_5-C_{12})$-aryloxy, $(C_1-C_6)$-alkylcarbonyloxy-$(C_1-C_4)$-alkoxy, $(C_3-C_{12})$-aryl-$(C_1-C_6)$-alkylcarbonyloxy-$(C_1-C_6)$-alkoxy, $NH_2$, mono- or di-$((C_1-C_6)$-alkyl)-amino, $(C_5-C_{12})$-aryl-$(C_1-C_6)$-alkylamino or $(C_1-C_6)$-dialkylaminocarbonylmethyloxy;

$R^{12}$, $R^{13}$, $R^{14}$, and $R_{15}$ are, independent of each other, hydrogen, $(C_1-C_8)$-alkyl which is optionally substituted once or more than once by fluorine, $(C_3-C_8)$-cycloalkyl, $(C_3-C8)$-cycloalkyl-$(C_1-C_6)$-alkyl, $(C_5-C_{12})$-aryl, $(C_5-C_{12})$-aryl-$(C_1-C_6)$-alkyl, $H_2N$, $R^8ONR^9$, $R^8OR^9$, $R^8OC(O)R^9$, $R^8R^8NR^9$, $R^8$—$(C_5-C_{12})$-aryl-$R^9$, HO—$(C_1-C_8)$-alkyl-$N(R^2)R^9$, $R^8N(R^2)C(O)R^9$, $R^8C(O)N(R^2)R^9$, $R^8C(O)R^9$, $R^2R^3N$—C(=$NR^2$)—$NR^2$, $R^2R^3N$—C(=$NR^2$), =O or =S;

where two adjacent substituents from $R^{12}$, $R^{13}$, $R^{14}$, and $R^{15}$ can also together be —$OCH_2O$—, —$OCH_2CH_2O$—, or —$OC(CH_3)O$—;

n is 1 or 2;

p and q are, independently of each other, 0 or 1;

and E is as defined in claim 1;

in all its stereoisomeric forms and mixtures thereof in all proportions, and its physiologically tolerated salts.

3. A compound of the formula I as claimed in claim 1, in which:

$A=A_1$ or $A_2$, wherein

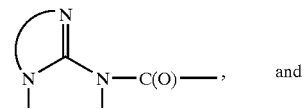

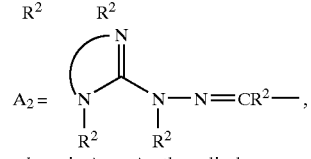

where, in $A_1$ or $A_2$, the radical

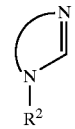

is a radical selected from the group consisting of

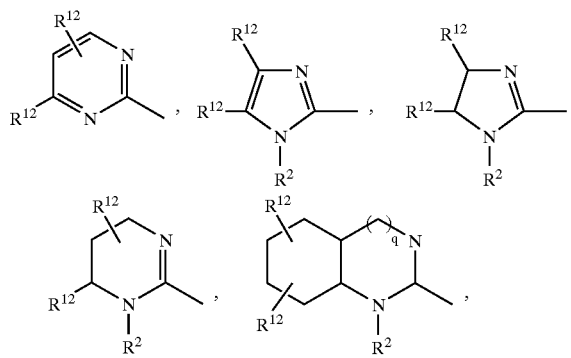

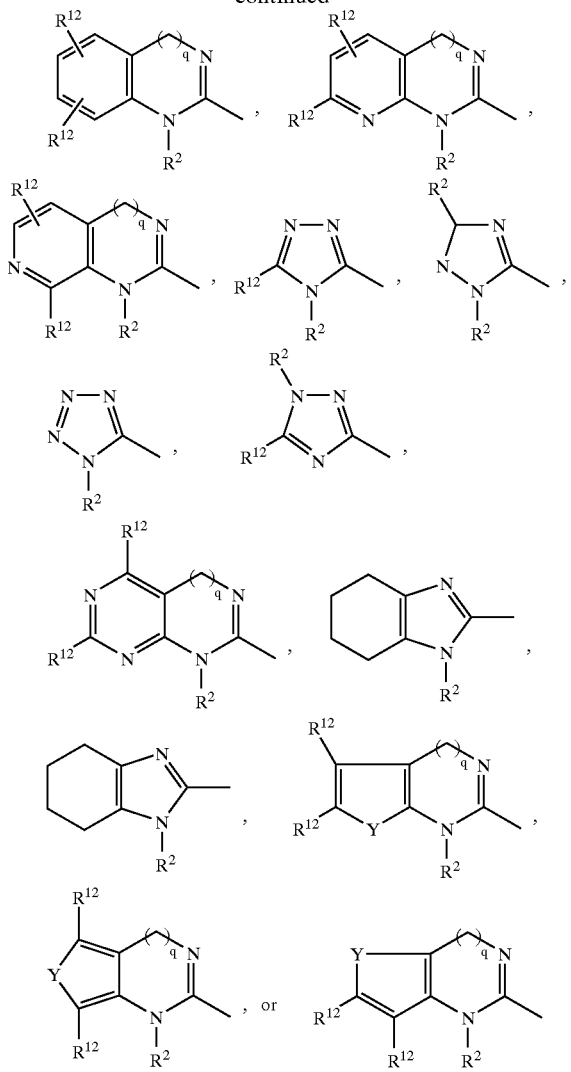

where Y=NR², O, or S;

B is a direct linkage, (C₁–C₆)-alkanediyl, (C₅ C₆) arylene or —CR²=CR³—, which may in each case be substituted, once or twice, by (C₁–C₆)-alkyl, D is a direct linkage, (C₁–C₆)-alkanediyl, (C₅–C₆)-arylene, —O—, —NR²—, —NR²—CO—, —NR²—C(O)—NR²—, —NR²—C(S)—NR²—, —OC(O)—, —CO—, —S(O)₂—NR²—, —NR²—S(O)—, —NR²—S(O)₂— or —CR²=CR³—, which may in case be substituted, once or twice, by (C₁–C₆)-alkyl, —CH=CH— or phenyl; where, if B is a direct linkage, then D may also be a direct linkage or a radical as defined under D, which radical is substituted once or twice, as described under D, and is linked to B by way of one of these substituents;

E is as defined in claim 1;

F is a direct linkage, (C₁–C₆)-alkanediyl, —O—, —CO—NR²—, —NR²—CO—, —NR²—C(O)—NR²—, —OC(O)—, —C(O)O—, —CO—, —S(O)₂—, —S(O)₂—NR²—, —NR²—S(O)₂—, —CR²=CR³— or —C≡C— which may in each case be substituted, once or twice, by (C₁–C₆)-alkyl, where the valence permits; and G is

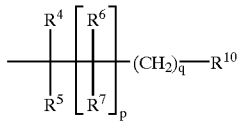

wherein

R² and R³ are, independent of each other, hydrogen, (C₁–C₆)-alkyl which is optionally substituted, once or more than once, by fluorine, (C₅–C₆)-cycloalkyl, (C₅–C₆)-cycloalkyl-(C₁–C₄)-alkyl, (C₅–C₁₀)-aryl, (C₅–C₁₀)-aryl-(C₁–C₄)-alkyl, R⁸OC(O)R⁹, R⁸R⁸NC(O)R⁹ or R⁸C(O)R⁹;

R⁴, R⁵, R⁶ and R⁷ are, independently of each other, hydrogen, fluorine, OH, (C₁–C₆)-alkyl, (C₅–C₁₄)-cycloalkyl, (C₅–C₁₄)-cycloalkyl-(C₁–C₆)-alkyl, R⁸OR⁹, R⁸CO₂R⁹, R⁸OC(O)R⁹, R⁸—(C₅–C₁₀)-aryl-R⁹, R⁸NHR⁹, R⁸R⁸NR⁹, R⁸NHC(O)OR⁹, R⁸S(O)ₙNHR⁹, R⁸OC(O)NHR⁹, R⁸C(O)NHR⁹, R⁸C(O)R⁹, R⁸NHC(O)NHR⁹, R⁸NHS(O)ₙNHR⁹, R⁸NHC(O)R⁹ or R⁸NHS(O)ₙR⁹, where at least one radical selected from the group consisting of R⁴, R⁵, R⁶ and R⁷ is a lipophilic radical;

R⁸ is hydrogen, (C₁–C₆)-alkyl, (C₅–C₁₄)-cycloalkyl, (C₅–C₁₄)-cycloalkyl-(C₁–C₄)-alkyl, (C₅–C₁₀)-aryl or (C₅–C₁₀)-aryl-(C₁–C₄)-alkyl, where the alkyl radicals can be substituted by 1 to 6 fluorine atoms;

R⁹ is a direct linkage or (C₁–C₆)-alkanediyl;

R¹⁰ is C(O)R¹¹;

R¹¹ is OH, (C₁–C₆)-alkoxy, (C₅–C₁₀)-aryl-(C₁–C₆)-alkoxy, (C₅–C₁₀)-aryloxy, (C₁–C₆)-alkylcarbonyloxy-(C₁–C₄)-alkoxy, (C₅–C₁₀)-aryl-(C₁–C₄)-alkylcarbonyloxy-(C₁–C₄)-alkoxy, NH₂ or mono- or di-(C₁–C₆-alkyl)-amino;

R¹² is hydrogen, (C₁–C₆)-alkyl which is optionally substituted, once or more than once, by fluorine, (C₃–C₆)-cycloalkyl, (C₃–C₆)-cycloalkyl-(C₁–C₄)-alkyl, (C₅–C₁₀)-aryl, (C₅–C₁₀)-aryl-(C₁–C₄)-alkyl, H₂N, R⁸OR⁹, R⁶OC(O)R⁹, R⁸—(C₅–C₁₀)-aryl-R⁹, R⁸R⁸NR⁹, R⁸NHC(O)R⁹, R⁸C(O)NHR⁹, H₂N—C(=NH)—, H₂N—C(=NH)—NH— or =O;

where two adjacent substituents R¹² may also be —OCH₂O— or —OCH₂CH₂O—;

n is 1 or 2; and p and q are, independent of each other, 0 or 1;

in all its stereoisomeric forms and mixtures thereof in all proportions, and its physiologically tolerated salts.

4. A compound of the formula I as claimed in claim 1, in which:

A=A₁ or A₂, wherein

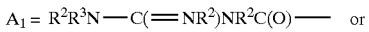

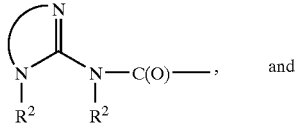

-continued $$A_2 = \begin{array}{c} N \\ | \\ N-N=CR^2- \\ | \quad | \\ R^2 \quad R^2 \end{array},$$

where in $A_1$ or $A_2$, the radical

[structure: 5-membered ring with N-R² and N]

is a radical selected from the group consisting of

[six heterocyclic structures with R¹² substituents]

B is $(C_1-C_4)$-alkanediyl, phenylene, pyridinediyl, thiophenediyl, furandiyl or $—CR^2=CR^3—$, which may in each case be substituted, once or twice, by $(C_1-C_4)$-alkyl, D is a direct linkage, $(C_1-C_4)$-alkanediyl, $—O—$, $—NR^2—$, $—NR^2CO—$, $—C(O)—NR^2—$, $—NR^2—C(O)—NR^2—$, $—C(O)—$ or $—CR^2=CR^3—$, which may in each case be substituted, once or twice, by $(C_1-C_4)$-alkyl, E is as defined in claim 1;

F is a direct linkage, $(C_1-C_6)$-alkanediyl, $—O—$, $—CO—NR^2—$, $—NR^2—CO—$, $—NR^2—C(O)—NR^2—$, $—S(O)_2—NR^2$, $—NR^2—S(O)_2—$, $—CR^2=CR^3—$, or $—C\equiv C—$, which may in each case be substituted, once or twice, where the valence permits, by $(C_1-C_6)$-alkyl; and G is $$\begin{array}{c} R^4 \\ | \\ —\!\!\!\!\!—\!\!\!\!\!—\!\!\!\!\!—\!\!\!\!\!—\!\!\!\!\!-(CH_2)_q\!-\!R^{10} \\ | \\ R^5 \end{array} \left[\begin{array}{c} R^6 \\ | \\ | \\ R^7 \end{array}\right]_p$$

wherein $R^2$ and $R^3$ are, independent of each other, hydrogen, $(C_1-C_4)$-alkyl, trifluoromethyl, pentafluoroethyl, $(C_5-C_6)$-cycloalkyl, $(C_5-C_6)$-cycloalkyl-$(C_1-C_4)$-alkyl, phenyl or benzyl; pentafluoroethyl, $(C_5-C_6)$-cycloalkyl, $(C_5-C_6)$-cycloalkyl-$(C_1-C_4)$-alkyl, phenyl or benzyl;

$R^4$ is $(C_{10}-C_{14})$-cycloalkyl, $(C_{10}-C_{14})$-cycloalkyl-$(C_1-C_4)$-alkyl, $R^{16}OR^9$, $R^{16}HNR^9$, $R^{16}NHC(O)OR^9$, $R^{16}S(O)_nNHR^9$, $R^{16}OC(O)NHR^9$, $R^{16}C(O)NHR^9$, $R^{16}C(O)R^9$, $R^{16}NHC(O)R^9$ or $R^{16}NHS(O)_nR^9$;

$R^5$ is hydrogen, $(C_1-C_6)$-alkyl, $(C_5-C_6)$-cycloalkyl, $(C_5-C_6)$-cycloalkyl-$(C_1-C_4)$-alkyl, trifluoromethyl, pentafluoroethyl, phenyl or benzyl;

$R^8$ is hydrogen, $(C_1-C_4)$-alkyl, $(C_5-C_6)$-cycloalkyl, $(C_5-C_6)$-cycloalkyl-$(C_1-C_2)$-alkyl, phenyl, benzyl, trifluoromethyl or pentafluoroethyl;

$R^9$ is a direct linkage or $(C_1-C_4)$-alkanediyl;

$R^{10}$ is $C(O)R^{11}$, $R^{11}$ is OH, $(C_1-C_6)$-alkoxy, phenoxy, benzyloxy, $(C_1-C_4)$-alkylcarbonyloxy-$(C_1-C_4)$-alkoxy, $NH_2$ or mono- or di-$(C_1-C_6$-alkyl)amino;

$R^{12}$ is hydrogen, $(C_1-C_4)$-alkyl, trifluoromethyl, pentafluoroethyl, $(C_5-C_6)$-cycloalkyl, $(C_5-C_6)$-cycloalkyl-$(C_1-C_2)$-alkyl, $(C_5-C_6)$-aryl, $(C_5-C_6)$-aryl-$(C_1-C_2)$-alkyl, $H_2N$, $R^8R^8NR^9$, $R^8NHC(O)R^9$, $H_2N—C(=NR)$ or $H_2N—C(=NH)—NH—$; where two adjacent substituents $R^{12}$ can also be $—OCH_2O—$ or $—OCH_2CH_2O—$;

$R^{16}$ is $(C_{10}-C_{14})$-cycloalkyl or $(C_{10}-C_{14})$-cycloalkyl-$(C_1-C_4)$-alkyl which may optionally be substituted, once or twice, by $(C_1-C_4)$-alkyl, trifluoromethyl, phenyl, benzyl, $(C_1-C_4)$-alkoxy, phenoxy, benzyloxy, $=O$ or mono- or di-$((C_1-C_4)$-alkyl)-amino;

n is 1 or 2; and q is 0 or 1;

in all its stereoisomeric forms and mixtures thereof in all proportions, and its physiologically tolerated salts.

5. A compound of formula I as claimed in claim 1, in which the distance between $R^{10}$ and the first N atom in A1 is from 12 to 13 covalent bonds, and in A2 from 11 to 12 covalent bonds along the shortest route between these atoms, in all its stereoisomeric forms and mixtures thereof in all proportions, and its physiologically tolerated salts.

6. A process for preparing a compound of formula I as claimed in claim 1, comprising linking, by means of fragment condensation, two or more fragments which can be derived retrosynthetically from formula I.

7. A pharmaceutical composition comprising at least one compound of formula I as claimed in claim 1, and/or its physiologically tolerated slats, in addition to at least one pharmaceutically tolerable carrier, excipient and/or additive.

8. A method of treating cardiovascular diseases, comprising administering to a patient in need thereof an effective amount of a compound of formula I as claimed in claim 1 and/or a physiologically tolerated salt thereof.

9. A method of treating nephropathies or retinopathies comprising administering to a patient in need thereof an effective amount of a compound of formula I as claimed in claim 1 and/or a physiologically tolerated salt thereof.

10. A method of treating diseases having as a causative agent the interaction between vitronectin receptors and their ligands in cell-cell or cell-matrix interaction processes comprising administering to a patient in need thereof an effective amount of a compound of formula I as claimed in claim 1 and/or a physiologically tolerated salt thereof.

11. A method for inhibiting bone resorption by osteoclasts, tumor growth, tumor metastasis, or inflammation comprising administering to a subject in need thereof an effective amount of at least one compound of claim 1, and/or physiologically tolerated salt thereof.

12. A method for the treatment or prophylaxis of osteoporosis comprising administering to a subject in need thereof an effective amount of at least one compound as claimed in claim 1.

13. A method for the treatment or prophylaxis of cancer comprising administering to a subject in need thereof an effective amount of at least one compound as claimed in claim 1.

* * * * *